(12) United States Patent
Middleton et al.

(10) Patent No.: US 7,060,836 B2
(45) Date of Patent: Jun. 13, 2006

(54) LACTAMS AS TACHYKININ ANTAGONISTS

(75) Inventors: Donald Stuart Middleton, Sandwich (GB); Alan Stobie, Sandwich (GB)

(73) Assignee: Pfizer, Inc, New York, NY (US)

( * ) Notice: Subject to any disclaimer, the term of this patent is extended or adjusted under 35 U.S.C. 154(b) by 595 days.

(21) Appl. No.: 10/322,068

(22) Filed: Dec. 17, 2002

(65) Prior Publication Data

US 2004/0132710 A1   Jul. 8, 2004

Related U.S. Application Data

(60) Provisional application No. 60/350,811, filed on Jan. 22, 2002.

(30) Foreign Application Priority Data

Dec. 18, 2001   (GB) .................. 0130261.1

(51) Int. Cl.
| | |
|---|---|
| C07D 211/60 | (2006.01) |
| C07D 211/08 | (2006.01) |
| A01N 57/00 | (2006.01) |
| A01N 43/40 | (2006.01) |
| A61K 31/435 | (2006.01) |

(52) U.S. Cl. ............... 546/184; 546/192; 546/245; 546/256; 514/89; 514/277; 514/315

(58) Field of Classification Search ............... 546/184, 546/192, 245, 256; 514/89, 277, 315
See application file for complete search history.

(56) References Cited

U.S. PATENT DOCUMENTS

| 5,968,923 A | 10/1999 | MacKenzie et al. ........ 514/210 |
| 6,242,438 B1 | 6/2001 | MacKenzie et al. ........ 514/210 |

*Primary Examiner*—Richard Raymond
*Assistant Examiner*—Paul V. Ward
(74) *Attorney, Agent, or Firm*—Gregg C. Benson; Carl J. Goddard

(57) ABSTRACT

Compounds of the formula (I):

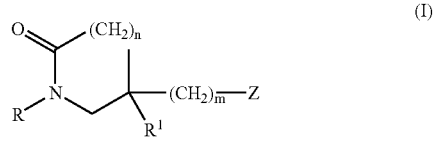

or a pharmaceutically acceptable salt, prodrug, solvate or polymorph thereof, wherein R, $R^1$, and Z are as defined herein, are useful in treating or preventing a condition for which an $NK_2$ antagonist is efficacious.

22 Claims, No Drawings

LACTAMS AS TACHYKININ ANTAGONISTS

This application is filed claiming priority to U.S. Provisional Application No. 60/350,811, filed Jan. 22, 2002, and GB Provisional Application No. 0130261.1, filed Dec. 18, 2001.

This invention relates to therapeutic agents of the lactam family and to processes for the preparation of, intermediates used in the preparation of, compositions containing and uses of, such derivatives.

International Patent Application Publication Number WO 96/05193 discloses various (azetidin-1-ylalkyl)lactams as tachykinin antagonists.

International Patent Application Publication Number WO97/25322 discloses various azetidinylalkyl derivatives of N-substituted nitrogen heterocycles as tachykinin antagonists.

The therapeutic agents of the present invention are antagonists of tachykinins, including neurokinin A (NKA), neurokinin B (NKB) and Substance P, acting at the human neurokinin-1 ($NK_1$), neurokinin-2 ($NK_2$) or neurokinin-3 ($NK_3$) receptor, or a combination of two or more thereof. They are therefore useful for preventing or treating inflammatory disease, a central nervous system (CNS) disorder, a gastro-intestinal (GI) disorder, a disease caused by *Helicobacter pylori* or other urease positive Gram negative bacteria, urological conditions, a pulmonary disorder, an allergy, a hypersensitivity disorder, a vasospastic disease, a proliferative disorder, a fibrosing or collagen disease, reflux sympathetic dystrophy, an addiction disorder, a stress-related somatic disorder, a peripheral neuropathy, a neuropathological disorder, a disorder related to immune enhancement or suppression, a rheumatic disease, an opthalmic disease, acute and chronic pain or a viral disease.

The present invention provides a compound of formula (I):

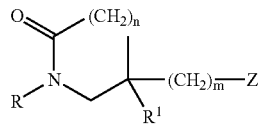

or a pharmaceutically acceptable salt, prodrug, solvate or polymorph thereof, wherein:

R is $het^a$;

$R^1$ is phenyl optionally substituted by one or more substituents independently selected from halogen, $C_{1-6}$ alkoxy optionally substituted by one or more halogen, and $C_{1-6}$ alkyl optionally substituted by one or more halogen;

m is 1–4;

Z is selected from:
a) $N(R^3)(R^4X)$ wherein X is $NR^3R^5$, $OR^3$, $Oaryl^1$, $Ohet^b$, $Ohet^c$, $aryl^1$, $het^b$ or $het^c$;
b) $N(R^3)Y$ wherein Y is $aryl^1$, $het^b$ or $het^c$; and
c) a 4–7 membered N containing saturated or partially saturated heterocycle said heterocycle attached to the alkylene link via said nitrogen atom, said heterocycle optionally containing an additional 1–3 groups, each independently selected from C=O, NH, $S(O)_p$ and O; optionally, said heterocycle is:
i) spirofused with $het^b$, such that both rings share 1 atom; or
ii) substituted by 1–3 groups each independently selected from $het^b$, $het^c$, $aryl^1$, $R^3$, $R^4OR^3$, $R^4C(O)R^3$, $OR^3$, $OR^7OR^3$, $OR^4OC(O)R^3$, $OR^4OC(O)NR^3R^6$, $S(O)_pR^4$, $C(O)R^3$, $C(O)NR^3R^6$, $C(O)OR^3$, $R^7C(O)OR^3$, $C(O)R^7OR^3$, $C(O)OR^7OR^3$, $CF_3$, $NR^3R^6$, $R^4NR^3R^5$, $OC(O)NR^3R^4$ and $NR^3R^5$;

wherein $R^3$ and $R^6$ are both independently selected from H and $C_{1-6}$ alkyl;

wherein $R^4$ and $R^7$ are both independently selected from $C_{1-6}$ alkylene;

wherein $R^5$ is selected from $C(O)OR^3$, $S(O)_pR^3$, $S(O)_paryl^1$, $C(O)R^3$, and $C(O)NR^3R^6$;

$het^b$ is a 4–7 membered heterocycle containing 1–3 heteroatoms, each independently selected from N, O and S, said N being optionally substituted with O, said ring optionally containing 1–2 C=O groups, said ring being saturated or partially saturated, said ring being optionally benzofused, said ring being optionally substituted by 1–3 substituents selected from halo, $R^3$, $OR^3$, $C(O)NR^3R^6$, $R^7NR^3R^6$, $NR^3R^5$, $NHS(O)_pR^4$, $S(O)_pNR^3R^6$, $S(O)_pR^4$, $NR^3R^6$ and $aryl^1$;

$het^a$ and $het^c$ independently represent a 5–7 membered aromatic heterocycle containing 1–3 heteroatoms each independently selected from N, O and S, said ring being optionally benzofused, said ring system as a whole being optionally substituted by 1–3 substituents, each independently selected from: halo, $R^3$, $OR^3$, $C(O)NR^3R^6$, $R^4NR^3R^6$, $NR^3R^5$, $NHS(O)_pR^4$, $S(O)_pNR^3R^6$, $S(O)_pR^4$, CN, $NR^3R^6$, and $R^4NR^3S(O)_pR^3$;

$aryl^1$ is phenyl or naphthyl, each optionally substituted by 1–3 substituents, each independently selected from: halo, $R^3$, $OR^3$, $C(O)NR^3R^6$, $R^7NR^3R^6$, $NR^3R^5$, $NHS(O)_pR^4$, $S(O)_pNR^3R^6$, $S(O)_pR^4$, CN;

p is 0, 1 or 2; and n is 0–4.

Halo includes fluoro, chloro, bromo and iodo groups.

Alkyl and alkylene include both straight chain and branched chain.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of the formula (I) include the hydrates thereof.

Also included within the present scope of the compounds of the formula (I) are polymorphs thereof.

It will also be appreciated that the compounds of the invention will include prodrugs of (I) and pharmaceutically acceptable derivatives of (I) in which the functional groups explicitly recited above have been derivatised to provide prodrugs which can be converted to the parent compound in vivo. Such prodrugs are discussed in Drugs of Today, 1983, 19, 499–538 and Annual Reports in Medicinal Chemistry, 1975, Vol. 10, Ch 31, 306–326.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof.

Those compounds of formula (I), which have the stereochemistry shown below are particularly preferred.

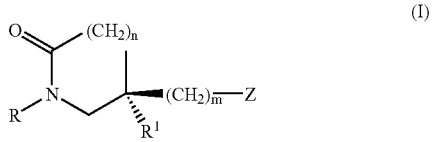

(I)

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferred embodiments of the present invention include compounds of formula (I) wherein:

Preferably R is pyridyl, optionally substituted by $NR^3R^6$, $R^3$ or $OR^3$.

More preferably R is pyridyl, optionally substituted by $NMe_2$, $C_{1-2}$ alkyl or $OC_{1-2}$ alkyl.

Yet more preferably R is pyridyl optionally substituted by methyl or ethyl.

Most preferably R is pyridyl optionally substituted by methyl.

Preferably the pyridyl moiety is substituted at the 2 position.

Preferably the lactam is attached to the pyridyl moiety at the 6 position of the pyridyl group.

Preferably $R^1$ is phenyl optionally substituted by 1 or 2 halo substituents.

More preferably $R^1$ is phenyl, optionally substituted by 1 or 2 substituents selected from fluoro and chloro.

Yet more preferably $R^1$ is phenyl, 3,4-difluorophenyl, 3-chlorophenyl, 4-chlorophenyl or 3,4-dichlorophenyl.

Most preferably $R^1$ is 3,4-difluorophenyl, 4-chlorophenyl or 3,4-dichlorophenyl.

Most preferably $R^1$ is 3,4-dichlorophenyl.

Preferably m is 2–3

Most preferably m is 2.

Preferably n is 1–4.

More preferably n is 1–3.

Yet more preferably n is 1–2.

Most preferably n is 2.

Preferably $R^3$ is H or $C_{1-4}$ alkyl; or

More preferably $R^3$ is H or $C_{1-2}$ alkyl

Preferably $R^4$ is C1-4 alkylene

More preferably $R^4$ is C1-2 alkylene

Preferably $R^5$ is $C(O)OR^3$, $C(O)R^3$, $C(O)NR^3R^6$

Preferably $R^6$ is H, $C_{1-4}$ alkyl; or

More preferably $R^6$ is H, $C_{1-2}$alkyl

Most preferably $R^6$ is H

Preferably $R^7$ is $C_{2-6}$ alkylene

More preferably $R^7$ is $C_{2-4}$ alkylene

Preferably Z is a piperidine or azetidine group optionally substituted by one or more of $het^b$ $het^c$, $aryl^1$, $OR^3$, $R^3$ and $NR^3R^5$, wherein;

$Het^b$ is a 5–6 membered saturated or partially saturated nitrogen containing heterocycle, said heterocycle optionally incorporating 1–2 groups each independently selected from O, C=O and N, said heterocycle being optionally benzofused, said heterocycle being optionally substituted by 1–2 substituents, each independently selected from $OR^3$, $R^3$, $NR^3R^6$, $NR^3R^5$, $aryl^1$, $SO_2R^4$ and $SO_2NR^3R^6$;

$Het^c$ is pyridyl, optionally substituted by 1 or 2 substituents each independently selected from halo and $OR^3$;

$aryl^1$ is phenyl, optionally substituted by 1 or 2 substituents each independently selected from halo and $OR^3$; and $R^3$, $R^4$, $R^5$ and $R^6$ are as herein defined.

Preferably, the piperidine or aziridine group is substituted at the 4 or 3 position respectively.

Most preferably Z is a piperidine or azetidine group, optionally substituted by $het^b$, $aryl^1$ and $NR^3R^5$; wherein $het^b$ is a morpholine or piperidine, optionally substituted at the 4 position by OH and or methyl; wherein;

$aryl^1$ is phenyl optionally substituted by OH; and $R^3$ is H or methyl and $R^5$ is $C(O)CH_3$.

Particularly preferred compounds include:

(5S)-5-(3,4-Dichlorophenyl)-1-(6-methyl-2-pyridinyl)-5-{2-[3-(4-morpholinyl)-1-azetidinyl]ethyl}-2-piperidinone (Example 131)

(5S)-5-(3,4-Dichlorophenyl)-1-(6-methyl-2-pyridinyl)-5-{2-[3-(4-hydroxypiperidinyl)-1-azetidinyl]ethyl}-2-piperidinone (Example 135a)

(5S)-5-(3,4-Dichlorophenyl)-5-[2-(4-methoxy-1-piperidinyl)ethyl]-1-(2-pyridinyl)-2-piperidinone (Example 61)

(5S)-5-(3,4-Dichlorophenyl)-1-(6-methyl-2-pyridinyl)-5-{{2-[4-hydroxy-4-phenyl]-1-piperidinyl}ethyl}-2-piperidinone (Example 134)

(5S)-5-(3,4-Dichlorophenyl)-5-{2-[4-hydroxy-4-(2-pyridyl)-1-piperidinyl]ethyl}-1-(2-pyridinyl)-2-piperidinone (Example 92)

N-(1-{2-[(3S)-3-(3,4-Dichlorophenyl)-6-oxo-1-(2-pyridinyl)piperidinyl]ethyl}-4-phenyl-4-piperidinyl)-acetamide (Example 90)

(5S)-5-(3,4-Dichlorophenyl)-1-(6-methoxy-2-pyridinyl)-5-{2-[3-(4-morpholinyl)-1-azetidinyl]ethyl}-2-piperidinone (Example 119)

5-(3,4-Dichlorophenyl)-1-(6-methyl-2-pyridinyl)-5-{2-[3-(4-oxo-1-piperidin)-1-azetidinyl]ethyl}-2-piperidinone (Example 168)

(5S)-5-(3,4-Dichlorophenyl)-5-{2-[3-(4-hydroxy-1-piperidinyl)-1-azetidinyl]ethyl}-1-(2-pyridinyl)-2-piperidinone (Example 73)

N-(1-{2-[(3S)-3-(3,4-Dichlorophenyl)-6-oxo-1-(2-pyridinyl)piperidinyl]ethyl}-4-piperidinyl)-N-methylacetamide (Example 158)

The invention further provides methods for the preparation of the compounds of the invention, which are described below and in the examples and Preparations section. The skilled man will appreciate that the compounds of the invention could be made by methods other than those herein described and or adaption of a plethora of methods known in the art. It is to be understood that the synthetic transformation methods specifically mentioned herein may be carried out in various different sequences in order that the desired substances can be efficiently assembled. The skilled chemist will exercise his judgement and skill as to the most efficient series of reactions for synthesis of a given target substance.

It will be apparent to those skilled in the art that sensitive functional groups may need to be protected and deprotected during synthesis of a substance of the invention. This may be achieved by conventional techniques, for example as described in "Protective Groups in Organic Synthesis" by T. W. Greene and P. G. M. Wuts, John Wiley and Sons Inc, 1991.

The compounds of formula (I) may be prepared in accordance with the following scheme:

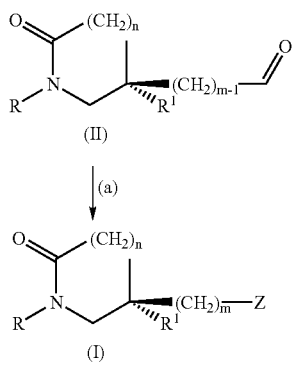

Compounds of formula (I) may be prepared from the compounds of formula (II) under the conditions of process step (a) a reductive amination. This involves the reaction of amine Z-H with aldehyde (II), with a suitable metal hydride reducing agent (to reduce intermediate imine), optionally in the presence of a suitable base and/or acid, optionally in the presence of a Lewis acid catalyst, in a suitable solvent at room temperature.

Suitable conditions include:
1 eq aldehyde (or HCl salt of), 1–2 eq of amine, 1–3 eq suitable reducing agent (e.g. $NaCNBH_3$, $NaBH(OAc)_3$), optionally in the presence of a base (eg Hünigs, $Et_3N$), and/or an acid (eg AcOH), in a suitable solvent (eg dichloromethane (DCM), or tetrahydrofuran (THF)) at from between 15 minutes and 72 hours.

Or (under Lewis acid catalysis)-1 eq aldehyde, excess of amine, an excess of reducing agent, in the presence of a base (eg $Et_3N$), in a suitable solvent (e.g. EtOH), using 10 eq of Lewis acid (eg $Ti(OiPr)_4$).

Particularly suitable are:
1 eq aldehyde, 1 to 1.5 eq amine, 1 to 3 eq $NaBH(OAc)_3$, optionally in the presence of 1 to 12 eq $Et_3N$, and optionally in the presence of 2 to 30 eq of AcOH, in DCM or THF for between 15 minutes and 72 hours at rt.

Or (under Lewis acid catalysis)-1 eq aldehyde, 1.1 eq amine, 1.5 eq $NaBH(OAc)_3$, in the presence of 2.5 eq $Et_3N$, in EtOH using 10 eq of $Ti(OiPr)_4$.

The compounds of formula (II) may be prepared in accordance with the following scheme.

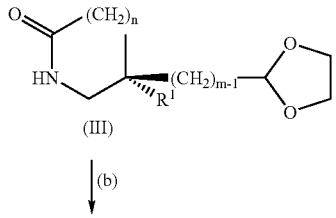

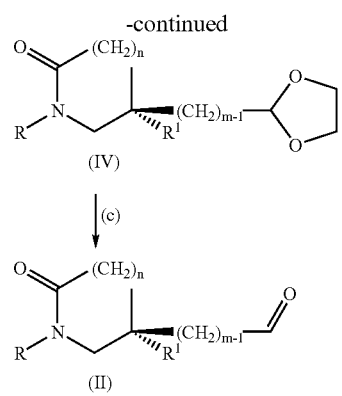

Compounds of formula (IV) may be prepared from the compounds of formula (III) under the conditions of process step (b), an alkylation reaction. Suitable conditions include using an excess of alkylating agent; in a preferred embodiment the conditions include an excess of a compound of formula (V)

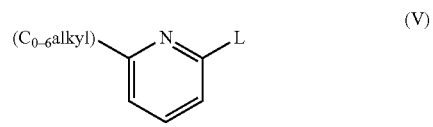

where L is halo, with an excess of suitable base (typically an alkali metal salt), in a suitable solvent (eg ethylene glycol dimethyl ether (DME), 1-methyl-2-pyrrolidinone (NMP)), optionally in the presence of a catalyst (e.g. CuI), at the reflux temp of the reaction for 1 to 24 hours.

Preferably a class of alkylation reaction known as the Goldberg reaction is used. This comprises 1.5 to 3 eq alkylating agent, V, where L is F, Cl or Br, 1.1 to 1.5 eq of $K_2CO_3$, or $KO^tBu$ in NMP or DME at reflux for 1 to 24 hours.

Compounds of formula (II) may be prepared from the compounds of formula (IV) under the conditions of process step (c), a dioxalan hydrolysis reaction. Suitable conditions include hydrolysis under acidic conditions, such as 2.5N HCl in THF at rt for 24 hours.

Process steps (b) and (c) may be carried out using "one pot" methodology without the isolation of compounds of formula (IV)

The compounds of formula (II) may also be prepared in accordance with the following scheme:

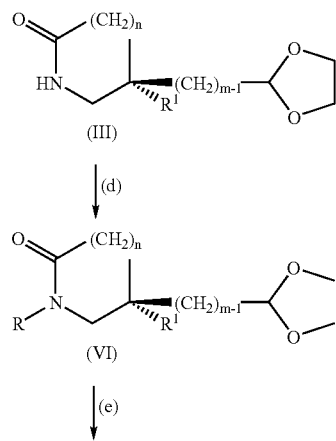

-continued

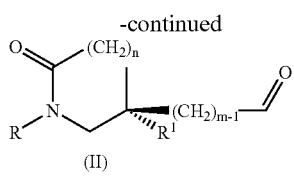

(II)

Compounds of formula (VI) may be prepared from the compounds of formula (III) under the conditions of process step (d), a dioxalan cleavage reaction. This is conducted under non-aqueous strongly acidic conditions, for example, Amberlyst® 15 resin in MeOH at rt for 18 hours.

Compounds of formula (II) may be prepared from the compounds of formula (VI) under the conditions of process step (e), an acetal hydrolysis reaction. Suitable conditions include hydrolysis under acidic conditions to give the aldehyde, for example 1.1–2.5N HCl in THF at rt for 18–24 hours.

The compounds of formula (I) may also be prepared in accordance with the following scheme:

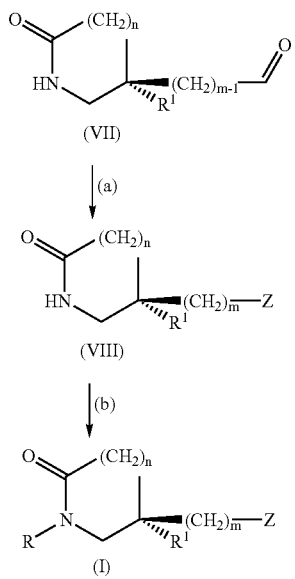

Compounds of formula (VIII) may be prepared from the compounds of formula (VII) under the conditions of process step (a), a reductive amination reaction as discussed earlier.

Compounds of formula (I) may be prepared from the compounds of formula (VIII) under the conditions of process step (b), an alkylation reaction as discussed earlier.

In addition to the process routes already described, compounds of formula (I) where Z is $N(R^3)(R^4X)$, where $R^3$ is $C_{1-6}$ alkyl, $R^4$ is $C_{1-6}$ alkylene and X is $het^b$ or $het^c$, may be prepared from the corresponding compounds of formula (I) where $R^2$ is hydrogen, by process step (a) a reductive amination reaction as discussed earlier.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the Examples and Preparations hereto.

The affinity of the compounds of formula (I), and their salts, for the human $NK_2$ receptor can be assessed in vitro by testing their ability to compete with [$^3H$] or [$^{125}I$] NKA (neurokinin A) for binding to membranes prepared from Chinese hamster ovary cells expressing the cloned human $NK_2$ receptor using a modification of the method described in McLean, S. et al., J. Pharm. Exp. Ther., 267, 472–9 (1993). The membranes are incubated (90 min, 25° C.) with [$^3H$] or [$^{125}I$] NKA and a range of concentrations of the test compound. Non specific binding was determined in the presence of 1 μM SR-48968 (N-[(2S)-4-[4-(acetylamino)-4-phenyl-1-piperidinyl]-2-(3,4-dichlorophenyl)butyl]-N-methyl benzamide).

All the compounds of the present invention (as exemplified herein) had a binding affinity for $NK_2$ receptors with Ki<1000 nM.

The binding Ki expressed in nM for selected compounds of the present invention are expressed below:
(5S)-5-(3,4-Dichlorophenyl)-1-(6-methyl-2-pyridinyl)-5-{2-[3-(4-morpholinyl)-1-azetidinyl]ethyl}-2-piperidinone (Example 131) Ki=3.8
(5S)-5-(3,4-Dichlorophenyl)-1-(6-methyl-2-pyridinyl)-5-{2-[3-(4-hydroxypiperidinyl)-1-azetidinyl]ethyl}-2-piperidinone (Example 135a) Ki=3.7
(5S)-5-(3,4-Dichlorophenyl)-5-[2-(4-methoxy-1-piperidinyl)ethyl]-1-(2-pyridinyl)-2-piperidinone (Example 61) Ki=12
(5S)-5-(3,4-Dichlorophenyl)-1-(6-methyl-2-pyridinyl)-5-{2-[4-hydroxy-4-phenyl]-1-piperidinyl}ethyl}-2-piperidinone (Example 134) Ki=1.9
(5S)-5-(3,4-Dichlorophenyl)-5-{2-[4-hydroxy-4-(2-pyridyl)-1-piperidinyl]ethyl}-1-(2-pyridinyl)-2-piperidinone (Example 92) Ki=7
N-(1-{2-[(3S)-3-(3,4-Dichlorophenyl)-6-oxo-1-(2-pyridinyl)piperidinyl]ethyl}-4-phenyl-4-piperidinyl)-acetamide (Example 90) Ki=2.4
(5S)-5-(3,4-Dichlorophenyl)-1-(6-methoxy-2-pyridinyl)-5-{2-[3-(4-morpholinyl)-1-azetidinyl]ethyl}-2-piperidinone (Example 119) Ki=5.4
5-(3,4-Dichlorophenyl)-1-(6-methyl-2-pyridinyl)-5-{2-[3-(4-oxo-1-piperidinyl)-1-azetidinyl]ethyl}-2-piperidinone (Example 168) Ki=2.6
(5S)-5-(3,4-Dichlorophenyl)-5-{2-[3-(4-hydroxy-1-piperidinyl)-1-azetidinyl]ethyl}-1-(2-pyridinyl)-2-piperidinone (Example 73) Ki=2.2
N-(1-{2-[(3S)-3-(3,4-Dichlorophenyl)-6-oxo-1-(2-pyridinyl)piperidinyl]ethyl}-4-piperidinyl)-N-methylacetamide (Example 158) Ki=8

The $NK_2$ receptor antagonist activity of the compounds of formula (I), and their salts, can be assessed in vitro by testing their ability to antagonise the contractile effects of the selective $NK_2$ receptor agonist [β Ala$^8$] NKA$_{(4-10)}$ in human bladder tissue or in rabbit pulmonary artery using the method of Patacchini and Maggi, Eur. J. Pharm., 236, 31–37 (1993).

Those compounds of the present invention, with binding affinity Ki<10 nM (using the modified method described in McLean, S. et al, J. Pharm. Exp. Ther., 267, 472–9 (1993)) were profiled using the method of Patacchini. These especially preferred compounds had $K_b$<10 nM or $pA_2$>8.

The compounds of formula (I), and their salts, can be tested for $NK_2$ receptor antagonist activity, in vivo, by testing their ability to inhibit bronchoconstriction induced by [β Ala$^8$] NKA$_{(4-10)}$ in the aneasthetised guinea pig using the method described by Murai et al, J. Pharm. Exp. Ther., 262, 403–8 (1992) or Metcalfe et al, Br. J. Pharmacol., 112, 563P (1994).

The compounds of formula (I), and their salts, can be tested for $NK_3$ receptor antagonist activity, in vitro, by testing their ability to compete with [$^3$H] senktide (a selective NK$_3$ receptor agonist) on membranes prepared from guinea pig cortex, using the method described in Chretein, et al, Eur. J. Pharmacol, 256, 73–78 (1994).

The compounds of the present invention have been found to be potent NK$_2$ antagonists.

The present invention provides for the use of a compound of formula (I) or a pharmaceutically acceptable salt, solvate or prodrug thereof as a medicament.

It further provides the use of compounds of formula (I) or a pharmaceutically acceptable salt, solvate or prodrug thereof in the preparation of a medicament for the treatment of a condition for which an NK$_2$ antagonist is efficacious.

As NK$_2$ antagonists, the therapeutic agents of the present invention are therefore useful for preventing or treating an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, dyspepsia, irritable bowel syndrome, gastro-oesophageal reflux, faecal incontinence, colitis, ulcerative colitis or Crohn's disease, a disease caused by *Helicobacter pylori* or other urease positive Gram negative bacteria, urological conditions, ie a bladder disorder or a urogenital tract disorder (such as incontinence, hyperreflexia, impotence or cystitis) or associated conditions such as benign prostatic hyperplasia, over active bladder and lower uterine tract symptoms, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a vasospastic disease such as angina or Reynaud's disease, a proliferative disorder such as cancer or a disorder involving fibroblast proliferation, a fibrosing or collagen disease such as scieroderma or eosinophillic fascioliasis, reflux sympathetic dystrophy such as shoulder/hand syndrome, an addiction disorder such as alcoholism, a stress-related somatic disorder, a neuropathological disorder such as Parkinson's disease, Alzheimer's disease or multiple sclerosis, a disorder related to immune enhancement or suppression such as systemic lupus erythematosis, a rheumatic disease such as fibrositis, emesis, cough, migraine, an opthalmic disease such as proliferative retinopathy, occular inflammation, conjunctivitis, or a viral disease such as influenza or a cold.

The compounds of the present invention are also useful in the prevention and treatment of pain; both acute and chronic.

Acute pain is short-lived (e.g. post-operative pain). Chronic pain is usually defined as pain persisting from 3 to 6 months and includes somatogenic pains and psychogenic pains. Psychogenic pain is that which occurs without an organic origin such as low back pain, a typical facial pain and chronic headache.

Other types of pain are caused by injury or infection of peripheral sensory nerves. It includes, but is not limited to pain from peripheral nerve trauma, herpes virus infection, diabetes mellitus, causalgia, plexus avulsion, neuroma, limb amputation and vasculitis. Neuropathic pain is also caused by nerve damage from chronic alcoholism, human immunodeficiency virus infection, hypothyroidism, uremia or vitamin deficiencies.

Further types of pain are: neuropathic pain for example, AIDS neuropathy, post herpetic neuralgia, diabetic neuropathy and trigeminal neuralgia, fibromyalgia, pain associated with somatoform disorders, arthritic pain, cancer pain, neck pain, shoulder pain, back pain, cluster headaches, tension-type headache, migraine, herpes neuralgia, phantom limb pain, central pain, dental pain, NSAID-resistant pain, visceral pain, surgical pain, post-operative pain, bone injury pain, pain during labor and delivery, pain resulting from burns, including sunburn, post-partum pain, angina pain, and genitourinary tract-related pain including cystitis. The term pain shall also preferably refer to nociceptive pain or nociception. Examples of acute pain include, in particular, post-operative pain such as pain following a dental extraction, migraine, headache and trigeminal neuralgia.

Examples of chronic pain include, in particular, musculoskeletal pain or pain associated with musculo-skeletal disorders such as rheumatoid arthritis, osteoarthritis, ankylosing spondylitis, sero-negative (non-rheumatoid) arthropathies, non-articular rheumatism and peri-articular disorders, and pain associated with cancer; pain with an inflammatory component such as rheumatic pain, secondary inflammatory osteoarthrosis, dental pain and dysmenorrhoea; back pain such as low back pain e.g. spinal stenosis, prolapsed disc or sciatica; trauma; herpes zoster; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; gastrointestinal pain such as functional bowel disorders, which include non-ulcer dyspepsia, non-cardiac chest pain and irritable bowel syndrome. (Irritable bowel syndrome is a gastrointestinal disorder characterised by the presence of abdominal pain and altered bowel habits without any evidence of organic disease); traumatic pain such as postoperative pain; traumatic avulsion pain such as brachial plexus; chronic pain such as arthritic pain such as occurring in osteo-, rheumatoid or psoriatic arthritis; various forms of headache such as migraine, acute or chronic tension headache, temporomandibular pain, maxillary sinus pain, cluster headache; odontalgia; pain of visceral origin; nerve entrapment pain; sport's injury pain; menstrual pain; meningitis; arachnoiditis: angina; gout; burns; scar pain; itch; and thalamic pain such as post stroke thalamic pain.

Accordingly the present invention provides the use of compounds of formula (I) or a pharmaceutically acceptable salt, solvate or prodrug thereof in the preparation of a medicament for the treatment of a condition selected from: inflammatory disease, a central nervous system (CNS) disorder, a gastro-intestinal (GI) disorder, a disease caused by *Helicobacter pylori* or other urease positive Gram negative bacteria, urological conditions, a pulmonary disorder, an allergy, a hypersensitivity disorder, a vasospastic disease, a proliferative disorder, a fibrosing or collagen disease, reflux sympathetic dystrophy, an addiction disorder, a stress-related somatic disorder, a peripheral neuropathy, a neuropathological disorder, a disorder related to immune enhancement or suppression, a rheumatic disease, an opthalmic disease, acute and chronic pain or a viral disease.

A preferred embodiment of the present invention provides the use of compounds of formula (I) or a pharmaceutically acceptable salt, solvate or prodrug thereof in the preparation of a medicament for the treatment of a condition selected from: urological conditions or acute and chronic pain.

Particularly suitable urological conditions include incontinence, hyperreflexia, benign prostatic hyperplasia, over active bladder and lower uterine tract symptoms.

A particularly preferred urological condition is over active bladder.

A particularly preferred pain condition is neuropathic pain.

The invention also provides for a method of treating or preventing a condition for which an NK$_2$ antagonist is efficacious which comprises administering a therapeutically effective amount of a compound of formula (I) and pharmaceutically acceptable salts and prodrugs thereof to a patient in need of treatment.

The compounds of the formula (I) can also be administered in combination with other active agents. Preferred agents include: compounds which modulate the action of atrial natriuretic factor (also known as atrial natriuretic peptide), such as inhibitors of neutral endopeptidase; compounds which inhibit angiotensin-converting enzyme such as enalapril, and combined inhibitors of angiotensin-converting enzyme and neutral endopeptidase such as omapatrilat; angiotensin receptor antagonists such as losartan; substrates for NO-synthase, i.e. L-arginine; calcium-channel blockers such as amlodipine; antagonists of endothelin receptors and inhibitors of endothelin-converting enzyme; cholesterol lowering agents e.g. statins and fibrates; anti-platelet and antithrombotic agents, e.g. tPA, uPA, warfarin, hirudin and other thrombin inhibitors, heparin, thromboplastin activating factor inhibitors; insulin sensitising agents such as rezulin and hypoglycaemic agents such as glipizide; L-DOPA and carbidopa; acetylcholinesterase inhibitors such as donezipil or steroidal; non-steroidal anti-inflammatory agents (NSAIDS) such as aspirin and ibuprofen; cGMP PDE$_5$ inhibitors such as sildenafil (Viagra™), vardenafil and cialis; muscarinic antagonists such as oxybutynin, tolterodine, propiverine, trospium chloride and darifenacin; alpha-adrenoceptor antagonists such as doxazosin (Cardura™), tamsulosin, 4-Amino-6,7-dimethoxy-2-(5-methanesulfonamido-1,2,3,4-tetrahydroisoquinol-2-yl)-5-(2-pyridyl) quinazoline and 5-cyclopropyl-7-methoxy-2-(2-(4-morpholinylmethyl)-7,8-dihydro[1,6]naphthryridin-6(5H)-yl)-4(3H)-quinazolinone; serotonin/noradrenalin reuptake inhibitors (SNRI) such a duloxetine, venlafaxine and milnacipran; noradrenalin reuptake inhibitors such as reboxetine; NK$_1$ antagonists such as (αR, 9R)-7-[3,5-Bis(trifluoromethyl)benzyl]-8,9,10,11-tetrahydro-9-methyl-5-(4-methylphenyl)-7H-[1,4]diazocino[2,1-g][1,7]naphthyridine-6,13-dione (TAK-637), 5-[[(2R, 3S)-2-[(1R)-1-[3,5-Bis(trifluoromethyl)phenyl]ethoxy]-3-(4-fluorophenyl)-4-morpholinyl]methyl]-1,2-dihydro-3H-1,2,4-Triazol-3-one (MK-869), lanepitant, dapitant and 3-[[2-Methoxy-5-(trifluoromethoxy)phenyl]methylamino]-2-phenyl-piperidine, (2S, 3S); 5-HT$_{1A}$ agonists/antagonists such as buspirone and robalzotan; COX$_2$ inhibitors such as celecoxib (Celebrix™), rofecoxib (Vioxx™) and valdecoxib; non-selective COX inhibitors (preferably with 'GI protection') such as HCT-1026 (nitroflurbiprofen); opioids such as morphine, codeine; tricyclic antidepressants such as desipramine and amytriptiline; anticonvulsants such as gabapentin, serotonin reuptake inhibitors such as fluoxetine and sertraline; serotonin receptor agonists and antagonists, cholinergic (muscarinic and nicotinic) analgesics, sedatives such as amobarbital and temazepam, skeletal muscle relaxants such as baclofen; NMDA receptor antagonists such as dextromorphan and ketamine; vanilloid receptor agonists such as resinferatoxin; HMG-CoA reductase inhibitors such as atorvastatin (Lipitor™), simvastatin (Zocor™), pravastatin (Pravacol™) and rosuvastatin (Crestor™); and estrogenic modulators such as hormone replacement therapy and selective estrogen receptor modulators, such as lasofoxifene, tamoxifene and raloxifene.

The NK$_2$ antagonists of this invention can also be administered in combination with other active agents in the treatment of urological conditions, particularly incontinence, hyperreflexia, benign prostatic hyperplasia, over active bladder and lower uterine tract symptoms.

Accordingly the present invention provides for the use of a compound of formula (I) in the preparation of a medicament in combination with an agent selected from: Muscarinic antagonists; alpha-adrenoceptor antagonists; serotonin/noradrenalin reuptake inhibitors (SNRI); noradrenalin reuptake inhibitors; NK$_1$ antagonists; 5-HT$_{1A}$ agonists/antagonists; PDE$_5$ inhibitors; COX$_2$ inhibitors; non-selective COX inhibitors; vanilloid receptor agonists; HMG-COA reductase inhibitors; and estrogenic modulators and selective estrogen receptor modulators for the treatment of urological conditions.

The NK$_2$ antagonists of this invention can also be administered in combination with other active agents in the treatment of pain.

Accordingly the present invention provides for the use of a compound of formula (I) in the preparation of a medicament in combination with an agent selected from: NSAIDs, opioids, muscarinic antagonists; cholinergic analgesics; alpha-adrenoceptor antagonists; serotonin/noradrenalin reuptake inhibitors (SNRI); COX$_2$ inhibitors; non-selective COX inhibitors; tricyclic antidepressants, anticonvulsants, serotonin reuptake inhibitors, serotonin receptor agonists and antagonists, sedatives, skeletal muscle relaxant and NMDA receptor antagonists for the treatment of pain.

It is to be appreciated that all references herein to treatment include curative, palliative and prophylactic treatment.

The compounds of the formula (I) can be administered alone but will generally be administered in admixture with a suitable pharmaceutical excipient, diluent or carrier selected with regard to the intended route of administration and standard pharmaceutical practice.

The present invention provides for a composition comprising a compound of formula (I) or a pharmaceutically acceptable salt, solvate or prodrug thereof and a pharmaceutically acceptable diluent or carrier.

The compounds of formula (I) may also be administered in combination with other suitable therapeutic agents. Accordingly the present invention provides for a composition comprising a compound of formula (I) or a pharmaceutically acceptable salt, solvate or prodrug thereof and an agent selected from: compounds which modulate the action of atrial natriuretic factor (also known as atrial natriuretic peptide), such as inhibitors of neutral endopeptidase; compounds which inhibit angiotensin-converting enzyme, and combined inhibitors of angiotensin-converting enzyme and neutral endopeptidase; angiotensin receptor antagonists; substrates for NO-synthase; calcium-channel blockers; antagonists of endothelin receptors and inhibitors of endothelin-converting enzyme-cholesterol lowering agents; anti-platelet and antithrombotic agents, thromboplastin activating factor inhibitors; insulin sensitising agents and hypoglycaemic agents; acetylcholinesterase inhibitors; non-steroidal anti-inflammatory agents (NSAIDs); cGMP PDE$_5$ inhibitors; muscarinic antagonists; alpha-adrenoceptor antagonists; serotonin/noradrenalin reuptake inhibitors (SNRI); noradrenalin reuptake inhibitors; NK$_1$ antagonists; 5-HT$_{1A}$ agonists/antagonists; COX$_2$ inhibitors; non-selective COX inhibitors (preferably with 'GI protection'); opioids; tricyclic antidepressants; anticonvulsants, serotonin reuptake inhibitors; serotonin receptor agonists and antagonists, cholinergic (muscarinic and nicotinic) analgesics, sedatives, skeletal muscle relaxants; NMDA receptor antagonists; vanilloid receptor agonists; HMG-CoA reductase inhibitors; estrogenic modulators and selective estrogen receptor modulators, and a pharmaceutically acceptable diluent or carrier.

In preferred embodiments the invention provides a composition comprising a compound of formula (I) or a pharmaceutically acceptable salt, solvate or prodrug thereof and an agent selected from: Muscarinic antagonists; alpha-adrenoceptor antagonists; serotonin/noradrenalin reuptake inhibitors (SNRI); reuptake inhibitors; $NK_1$ antagonists; $5-HT_{1A}$ agonists/antagonists; $PDE_5$ inhibitors; $COX_2$ inhibitors; non-selective COX inhibitors (preferably with 'GI protection'); vanilloid receptor agonists; HMG-CoA reductase inhibitors; estrogenic modulators and selective estrogen receptor modulators, and a pharmaceutically acceptable diluent or carrier.

Another preferred embodiment provides a composition comprising a compound of formula (I) or a pharmaceutically acceptable salt, solvate or prodrug thereof and an agent selected from: NSAIDs, opioids, muscarinic antagonists; cholinergic analgesics; alpha-adrenoceptor antagonists; serotonin/noradrenalin reuptake inhibitors (SNRI); $COX_2$ inhibitors; non-selective COX inhibitors; tricyclic antidepressants, anticonvulsants, serotonin reuptake inhibitors, serotonin receptor agonists and antagonists, sedatives, skeletal muscle relaxant and NMDA receptor antagonists, and a pharmaceutically acceptable diluent or carrier.

Where other therapeutic agents are given in combination with the compounds of formula (I) they may be administered separately, simultaneously or sequentially.

The present invention provides for:
a) a composition comprising a compound of formula (I) or a pharmaceutically acceptable salt, solvate or prodrug thereof and a pharmaceutically acceptable diluent or carrier;
b) a composition comprising an agent selected from: compounds which modulate the action of atrial natriuretic factor (also known as atrial natriuretic peptide), such as inhibitors of neutral endopeptidase; compounds which inhibit angiotensin-converting enzyme, and combined inhibitors of angiotensin-converting enzyme and neutral endopeptidase; angiotensin receptor antagonists; substrates for NO-synthase; calcium-channel blockers; antagonists of endothelin receptors and inhibitors of endothelin-converting enzyme; cholesterol lowering agents; antiplatelet and antithrombotic agents, thromboplastin activating factor inhibitors; insulin sensitising agents and hypoglycaemic agents; acetylcholinesterase inhibitors; non-steroidal anti-inflammatory agents (NSAIDs); cGMP $PDE_5$ inhibitors; muscarinic antagonists; alpha-adrenoceptor antagonists; serotonin/noradrenalin reuptake inhibitors (SNRI); noradrenaline reuptake inhibitors; $NK_1$ antagonists; $5-HT_{1A}$ agonists/antagonists; $COX_2$ inhibitors; non-selective COX inhibitors (preferably with 'GI protection'); opioids; tricyclic antidepressants; anticonvulsants, serotonin reuptake inhibitors; serotonin receptor agonists and antagonists, cholinergic (muscarinic and nicotinic) analgesics, sedatives, skeletal muscle relaxants; NMDA receptor antagonists; vanilloid receptor agonists; HMG-CoA reductase inhibitors; estrogenic modulators and selective estrogen receptor modulators, and a pharmaceutically acceptable diluent or carrier; and
c) a container.

The invention further provides in a preferred embodiment for:
a) a composition comprising a compound of formula (I) or a pharmaceutically acceptable salt, solvate or prodrug thereof and a pharmaceutically acceptable diluent or carrier; and
b) a composition comprising a compound of formula (I) or a pharmaceutically acceptable salt, solvate or prodrug thereof and an agent selected from: muscarinic antagonists; alpha-adrenoceptor antagonists; serotonin/noradrenalin reuptake inhibitors (SNRI); reuptake inhibitors; $NK_1$ antagonists; $5-HT_{1A}$ agonists/antagonists; $PDE_5$ inhibitors; $COX_2$ inhibitors; non-selective COX inhibitors (preferably with 'GI protection'); vanilloid receptor agonists; HMG-COA reductase inhibitors; estrogenic modulators and selective estrogen receptor modulators, and a pharmaceutically acceptable diluent or carrier; and
c) a container.

In a further preferred embodiment, the invention provides for:
a) a composition comprising a compound of formula (I) or a pharmaceutically acceptable salt, solvate or prodrug thereof and a pharmaceutically acceptable diluent or carrier; and
b) a composition comprising a compound of formula (I) or a pharmaceutically acceptable salt, solvate or prodrug thereof and an agent selected from: NSAIDs, opioids, muscarinic antagonists; cholinergic analgesics; alpha-adrenoceptor antagonists; serotonin/noradrenalin reuptake inhibitors (SNRI); $COX_2$ inhibitors; non-selective COX inhibitors; tricyclic antidepressants, anticonvulsants, serotonin reuptake inhibitors, serotonin receptor agonists and antagonists, sedatives, skeletal muscle relaxant and NMDA receptor antagonists, and a pharmaceutically acceptable diluent or carrier; and
c) a container.

For example, the compounds of the formula (I) can be administered orally, buccally or sublingually in the form of tablets, capsules, ovules, elixirs, solutions or suspensions, which may contain flavouring or colouring agents, for immediate-, delayed-, modified-, sustained-, pulsed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

Alternatively, the compounds of the formula (I) can be administered in the form of a suppository or pessary, or they may be applied topically in the form of a gel, hydrogel, lotion, solution, cream, ointment or dusting powder. The compounds of the formula (I) may also be dermally or transdermally administered, for example, by the use of a skin patch. They may also be administered by the pulmonary or rectal routes.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyidodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The compounds of the invention may have the advantage that they are more potent, have a longer duration of action, are more stable, have fewer side effects, are more selective (in particular for the $NK_2$ receptor) and have improved cardiac safety, or have other more useful properties than the compounds of the prior art.

The following examples illustrate the preparation of the compounds of the formula (I):

EXAMPLE 1

(5S)-5-(3,4-Dichlorophenyl)-5-[2-(4-hydroxy-1-piperidinyl)ethyl]-1-(2-pyridinyl)-2-piperidinone

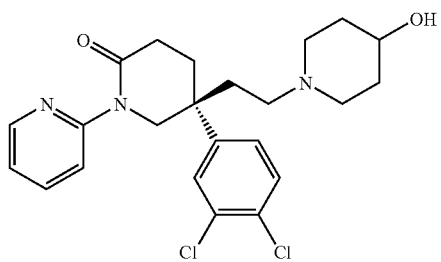

Sodium triacetoxyborohydride (262 mg, 1.24 mmol) was added to a solution of the aldehyde from preparation 11a (250 mg, 0.62 mmol) and 4-hydroxypiperidine (90 mg, 0.9 mmol) in dichloromethane (100 ml), and the reaction stirred at room temperature for 90 minutes. The mixture was washed with water, dried ($MgSO_4$) and concentrated under reduced pressure. The crude product was purified by column chromatography on silica gel using an elution gradient of dichloromethane:methanol (100:0 to 95:5) to afford the title compound as a white solid, 156 mg.

$^1$Hnmr ($CDCl_3$, 400 MHz) δ: 1.58 (m, 2H), 1.90–2.30 (m, 11H), 2.60 (m, 2H), 2.75 (m, 2H), 3.75 (m, 1H), 3.96 (d, 1H), 4.60 (d, 1H), 7.14 (m, 1H), 7.25 (m, 1H), 7.40 (d, 1H), 7.50 (s, 1H), 7.72 (s, 2H), 8.50 (d, 1H).

LRMS: m/z ($TSP^+$) 448.1, 450.1 [$MH^+$]

Microanalysis found: C, 58.34; H, 6.15; N, 8.57. $C_{23}H_{27}Cl_2N_3O_2 \cdot 0.10CH_2Cl_2 \cdot 1H_2O$ requires C, 58.42; H, 6.20; N, 8.85%.

EXAMPLES 2 TO 10

The following examples of general structure:

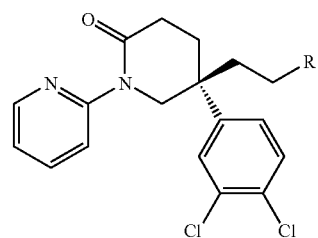

were prepared from the aldehyde hydrochloride from preparation 11b and the appropriate amines, following a similar procedure to that described in example 1.

| Ex No. | R | Yield (%) | Data |
|---|---|---|---|
| 2[1a] | —NH—CH₂CH₂—NH-boc | 58 yellow gum | ¹Hnmr (CDCl₃, 400MHz) δ: 1.40(s, 9H), 1.80–2.60(m, 9H), 3.16(m, 3H), 3.90(d, 1H), 4.58(d, 1H), 4.88(s, 1H), 7.14(m, 1H), 7.22(d, 1H), 7.41(d, 1H), 7.48(d, 1H), 7.72(d, 2H), 8.50(d, 1H). LRMS: m/z (TSP⁺) 507.2, 509.2 [MH⁺] Microanalysis found: C, 57.11; H, 6.96; N, 10.42. $C_{28}H_{32}Cl_2N_4O_3$; $0.05CH_2Cl_2$; $1H_2O$ requires C, 56.91; H, 6.31; N,10.60%. |
| 3[2b] | azetidinyl-piperazinyl-SO₂NH₂ | 29 white solid | ¹Hnmr (CDCl₃, 300MHz) δ: 1.64–1.96(m, 2H), 2.16(m, 2H), 2.23–2.43(m, 7H), 2.60(m, 1H), 2.78(m, 2H), 2.97(m, 1H), 3.20(m, 4H), 3.43(m, 2H), 3.92(d, 1H), 4.52(m, 3H), 7.19(m, 2H), 7.43(d, 1H), 7.47(s, 1H), 7.74(m, 2H), 8.52(d, 1H). LRMS: m/z (TSP⁺) 488.8, 490.7 [M—SO₂NH₂]⁺ Microanalysis Found: C, 40.29; H, 5.77; N, 11.18. $C_{25}H_{32}Cl_2N_6O_3S;3HCl;4H_2O$ requires C, 40.09; H, 5.79; N, 11.22% |
| 4[1c] | morpholinyl | 66 | ¹Hnmr (CDCl₃, 400MHz) δ: 1.50(bs, 3H), 1.80–2.35(m, 8H), 2.56(m, 1H), 3.60(bs, 4H), 3.95(d, 1H), 4.60(d, 1H), 7.08(dd, 1H), 7.24(m, 1H), 7.38(d, 1H), 7.44(d, 1H), 7.66(d, 2H), 8.45(d, 1H). Microanalysis, Found: C, 59.72; H, 5.71; N, 9.56. $C_{22}H_{25}Cl_2N_3O_2$; $0.1CH_2Cl_2$; $1H_2O$ Calc. C, 59.70; H, 5.76; N, 9.45%. |
| 5[d] | 4-methyl-4-hydroxypiperidinyl | 38 yellow solid | ¹Hnmr (CDCl₃, 400MHz) δ: 1.28(s, 3H), 1.60(m, 2H), 2.24(m, 10H), 2.55–2.82(m, 4H), 3.80(m, 1H), 3.94(d, 1H), 4.60(d, 1H), 7.15(dd, 1H), 7.34(d, 1H), 7.44(d, 1H), 7.52(s, 1H), 7.74(d, 2H), 8.48(d, 1H). LRMS: m/z (TSP⁺) 462.2, 464.2 [MH⁺] Microanalysis found: C, 56.46; H, 6.51; N, 8.07. $C_{24}H_{29}Cl_2N_3O_2$; $0.5CH_2Cl_2$; $H_2O$ requires C,56.28; H, 6.17; N, 8.04%. |
| 6[e] | 4-(4-sulfamoylphenyl)piperidinyl | 57 white foam | ¹Hnmr (CDCl₃, 400MHz) δ: 1.62(m, 2H), 1.74(m, 2H), 1.90(m, 4H), 2.01(m, 1H), 2.15(m, 2H), 2.30(m, 2H), 2.44(m, 1H), 2.54(m, 1H), 2.62(d, 3H), 2.83(m, 2H), 4.00(d, 1H), 4.20(m, 1H), 4.65(d, 1H), 7.10(m, 1H), 7.20(m, 1H), 7.30(d, 2H), 7.39(d, 1H), 7.46(s, 1H), 7.66(m, 2H), 7.74(d, 2H), 8.45(d, 1H). LRMS: m/z (TSP⁺) 601.4 [M⁺] |
| 7[f] | 4-(ethoxycarbonyl)piperazinyl | 39 white foam | ¹Hnmr (CDCl₃, 400MHz) δ: 1.18(t, 3H), 1.82–2.02(m, 4H), 2.07–2.37(m, 7H), 2.58(m, 1H), 3.36(m, 4H), 3.90(d, 1H), 4.07(q, 2H), 4.61(d, 1H), 7.10(dd, 1H), 7.19(d, 1H), 7.38(d, 1H), 7.43(s, 1H), 7.67(m, 2H), 8.44(d, 1H). LRMS: m/z (TSP⁺) 505.3, 507.2 [MH⁺] Microanalysis found: C, 58.64; H, 6.16; N, 10.52. $C_{25}H_{30}Cl_2N_4O_3$; $0.45H_2O$ |
| 8[g] | 4-methyl-1,4-diazepanyl | 4 white solid | ¹Hnmr (CDCl₃, 300MHz) δ: 1.92(m, 4H), 2.10–2.40(m, 6H), 2.50(s, 3H), 2.54–2.88(m, 8H), 3.92(d, 1H), 4.64(d, 1H), 7.16(m, 1H), 7.20(d, 1H), 7.40(d, 1H), 7.46(s, 1H), 7.72(d, 2H), 8.48(d, 1H). LRMS: m/z (TSP⁺) 461.2, 463.2 [MH⁺] |

⊘ indicates text missing or illegible when filed

-continued

| Ex No. | R | Yield (%) | Data |
|---|---|---|---|
| 9[h] | (piperazine with N-SO2CH3 group) | 19 | ¹Hnmr (CDCl₃, 400MHz) δ: 1.78(m, 2H), 1.85(m, 2H), 2.18(m, 2H), 2.24(m, 3H), 2.54(m, 5H), 2.77(s, 3H), 3.28(m, 2H), 3.35(m, 2H), 3.88(d, 1H), 4.64(d, 1H), 7.12(m, 1H), 7.18(d, 1H), 7.38(d, 1H), 7.44(d, 1H), 7.68(d, 2H), 8.46(d, 1H). LRMS: m/z (TSP⁺) 525.1, 527.1 [MH⁺] |
| 10[1i] | (homopiperazine with N-Boc group) | 43 White solid | ¹Hnmr (CDCl₃, 400MHz) δ: 1.40(s, 9H), 1.70–2.60(m, 14H), 3.40(bs, 4H), 3.90(d, 1H), 4.62(d, 1H), 7.12(m, 1H), 7.22(d, 1H), 7.40(d, 1H), 7.44(s, 1H), 7.70(s, 2H), 8.44(d, 1H). LRMS: m/z (TSP⁺) 547.2, 549.2 [MH⁺] Microanalysis found: C, 58.52; H, 6.32; N, 9.13. $C_{28}H_{36}Cl_2N_4O_3$; 0.2CH$_2$Cl$_2$; H$_2$O requires C, 58.15; H, 6.64; N, 9.62%. |

[1]= the aldehyde from preparation 11a was used
[2]= prepared as the HCl salt
Starting amines:
[a]= t-butyl N-(2-aminoethyl)carbamate
[b]= 4-(3-azetidinyl)-1-piperazine sulphonamide trifluoroacetate as prepared in WO 9725322
[c]= morpholine
[d]= 4-methyl-4-piperidinol from preparation 26
[e]= N-methyl-4-(4-piperidinyl)benzenesulphonamide as prepared in EP291210
[f]= ethyl 1-piperazinecarboxylate
[g]= 1-methyl-1,4-diazepine as prepared in J.A.C.S., 76, 5805
[h]= 1-(methylsulphonyl)-1,4-diazepine from preparation 82
[i]= t-butyl 1-homopiperazinecarboxylate

EXAMPLES 11 TO 16

The following examples of general structure:

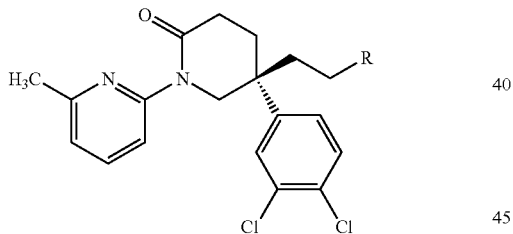

were prepared from the aldehyde from preparation 12a and the appropriate amines, following the procedure described in example 1.

| Example | R | Yield (%) | Data |
|---|---|---|---|
| 11[a] | (4-hydroxypiperidine) | 74 white solid | ¹Hnmr (CDCl₃, 400MHz) δ: 1.54(d, 2H), 1.84–2.30(m, 12H), 2.50–2.74(m, 6H), 3.66(m, 1H), 3.94(d, 1H), 4.60(d, 1H), 7.00(d, 1H), 7.24(d, 1H), 7.42(d, 2H), 7.62(m, 2H). LRMS: m/z (TSP⁺) 462.1, 464.1 [MH⁺] Microanalysis found: C, 59.81; H, 6.34; N, 8.57. $C_{24}H_{29}Cl_2N_3O_2$·0.1CH$_2$Cl$_2$; 0.7H$_2$O requires C, 59.87; H, 6.38; N, 8.69%. |

| Example | R | Yield (%) | Data |
|---|---|---|---|
| 12[b] | 4-hydroxy-4-methylpiperidine (OH, CH₃) | 64 yellow solid | ¹Hnmr (CDCl₃, 400MHz) δ: 1.20(s, 3H), 1.55(d, 2H), 1.70–2.65(m, 18H), 3.90(d, 1H), 4.60(d, 1H), 7.00(d, 1H), 7.25(d, 1H), 7.40(dd, 2H), 7.60(m, 2H). LRMS: m/z (TSP⁺) 476.2, 478.2 [MH⁺] Microanalysis found: C, 59.36; H, 6.63; N, 8.08. $C_{25}H_{31}Cl_2N_3O_2 \cdot 0.05CH_2Cl_2; 1.3H_2O$ requires C, 59.68; H, 6.74; N, 8.34%. |
| 13[c] | 2-(4-piperidinyl)-2-propanol | 70 | ¹Hnmr (CDCl₃, 400MHz) δ: 1.10(s, 6H), 1.22(m, 2H), 1.57–1.80(m, 6H), 1.92(m, 3H), 2.10(m, 2H), 2.25(m, 2H), 2.50(m, 4H), 2.82(m, 2H), 4.88(d, 1H), 4.50(d, 1H), 6.95(d, 1H), 7.20(d, 1H), 7.38(d, 2H), 7.56(m, 2H). LRMS: m/z (ES⁺) 504, 506 [MH⁺] |
| 14[d] | N-(4-phenyl-4-piperidinyl)acetamide | 51 white solid | ¹Hnmr (CDCl₃, 400MHz) δ: 1.90–2.20(m, 12H), 2.30(m, 4H), 2.52(s, 3H), 2.58(m, 2H), 2.70(d, 1H), 3.92(d, 1H), 4.65(d, 1H), 5.40(d, 1H), 7.00(d, 1H), 7.18–7.36(m, 6H), 7.40(d, 2H), 7.60(dd, 2H). LRMS: m/z (TSP⁺) 580.2, 582.2 [MH⁺] |
| 15[e] | 4-(4-fluorophenyl)-4-piperidinol | 39 white solid | ¹Hnmr (CDCl₃, 400MHz) δ: 1.70(m, 3H), 1.95–2.05(m, 4H), 2.18(m, 2H), 2.30(m, 5H), 2.54(s, 3H), 2.54(m, 1H), 2.65(m, 2H), 3.95(d, 1H), 4.62(d, 1H), 7.00(m, 3H), 7.30(m, 1H), 7.40(dd, 4H), 7.60(dd, 2H). LRMS: m/z (ES⁺) 556, 558 [MH⁺] Microanalysis found: C, 63.60; H, 5.76; N, 7.41. $C_{30}H_{32}Cl_2FN_3O_2; 0.1CH_2Cl_2; 0.1H_2O$ requires C, 63.78; H, 5.76; N, 7.41%. |
| 16[f] | morpholine | 62 white solid | ¹Hnmr (CDCl₃, 400MHz) δ: 1.95–2.40(m, 11H), 2.58(s, 3H), 2.58(m, 1H), 3.65(m, 4H), 3.90(d, 1H), 4.62(d, 1H), 7.00(d, 1H), 7.28(d, 1H), 7.40(d, 2H), 7.60(dd, 2H). LRMS: m/z (TSP⁺) 448.2, 450.2 [MH⁺] Microanalysis found: C, 60.64; H, 5.98; N, 9.16. $C_{23}H_{27}Cl_2N_3O_2; 0.1CH_2Cl_2$ requires C, 60.73; H, 6.00; N, 9.20%. |

⊕ indicates text missing or illegible when filed

Starting amines:
[a] = 4-hydroxypiperidine
[b] = 4-methyl-4-piperidinol from preparation 26
[c] = 2-(4-piperidinyl)-2-propanol as prepared in EP 625509
[d] = N-(4-phenyl-4-piperidinyl)acetamide from preparation 32
[e] = 4-(4-fluorophenyl)-4-piperidinol
[f] = morpholine

EXAMPLE 17

(5S)-5-(3,4-Dichlorophenyl)-5-[2-(4-phenyl-1-piperidinyl)ethyl]-1-(2-pyridinyl)-2-piperidinone

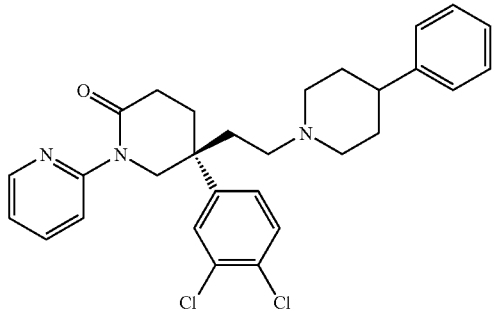

Sodium triacetoxyborohydride (267 mg, 1.26 mmol) was added to a solution of the aldehyde hydrochloride from preparation 11b (250 mg, 0.63 mmol) and 4-phenylpiperidine (151 mg, 0.94 mmol) in dichloromethane (200 ml), and the reaction stirred at room temperature for 2 hours. The mixture was washed with 2N sodium hydroxide solution (200 ml), the aqueous layer extracted with dichloromethane (2×200 ml), the combined organic extracts were dried (MgSO$_4$) and concentrated under reduced pressure. The crude product was purified by column chromatography on silica gel using dichloromethane:methanol:0.88 ammonia (95:5:0.5) as eluant to afford the title compound as a white foam.

$^1$Hnmr (CDCl$_3$, 400 MHz) δ: 1.74 (m, 6H), 1.83–2.08 (m, 5H), 2.18 (m, 2H), 2.32 (m, 2H), 2.40 (m, 1H), 2.60 (m, 1H), 3.90 (d, 1H), 4.68 (d, 1H), 7.18 (m, 4H), 7.28 (m, 3H), 7.41 (d, 1H), 7.50 (s, 1H), 7.73 (m, 2H), 8.50 (d, 1H).

Microanalysis found: C, 66.65; H, 6.16; N, 8.06. C$_{29}$H$_{31}$Cl$_2$N$_3$O;0.78H$_2$O requires C, 66.66; H, 6.28; N, 8.04%.

EXAMPLES 18 TO 25

The following examples of general structure:

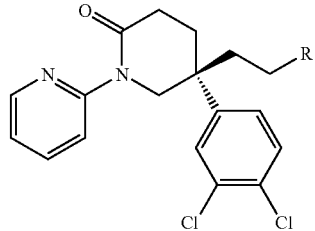

were prepared from the aldehyde hydrochloride from preparation 11b and the appropriate amine, following a similar procedure to that described in example 17.

| Example | R | Yield (%) | Data |
|---|---|---|---|
| 18[1a] | ⤳NH–CH$_2$–Ph | 50 white solid | $^1$Hnmr (CDCl$_3$, 400MHz) δ: 2.24(m, 2H), 2.41–2.75(m, 5H), 2.91(m, 1H), 3.80–4.00(m, 2H), 4.40(d, 1H), 4.54(d, 1H), 7.30(m, 4H), 7.39(d, 1H), 7.43(s, 1H), 7.54(m, 3H), 7.88(d, 1H), 8.15(dd, 1H), 8.61(d, 1H), 9.90(bs, 1H), 10.05(bs, 1H). LRMS: m/z (TSP$^+$) 454.0, 456.0 [MH$^+$] |
| 19[1b] | ⤳NH–CH$_2$CH$_2$–Ph | 65 white solid | $^1$Hnmr (CDCl$_3$, 400MHz) δ: 2.25(m, 2H), 2.42(m, 1H), 2.57(m, 3H), 2.75(m, 1H), 2.90(m, 1H), 3.01(m, 2H), 3.16(m, 2H), 4.35(m, 2H), 4.58(d, 1H), 7.21(m, 5H), 7.38(d, 1H), 7.42(d, 2H), 7.50(s, 1H), 7.84(d, 1H), 8.05(dd, 1H), 8.62(d, 1H), 9.82(bs, 1H), 9.96(bs, 1H). LRMS: m/z (TSP$^+$) 468.0, 470.0 [MH$^+$] Microanalysis found: C, 57.32; H, 5.50; N, 7.59. C$_{26}$H$_{27}$Cl$_2$N$_3$O; 2HCl; 0.05CH$_2$Cl$_2$ requires C, 57.35; H, 5.38; N, 7.70%. |
| 20[c] | azetidine-spiro-tetrahydropyran | 69 white foam | $^1$Hnmr (CDCl$_3$, 300MHz) δ: 1.63–1.88(m, 6H), 2.08–2.40(m, 5H), 2.55–2.64(m, 1H), 2.89(m, 4H), 3.57(m, 4H), 3.93(d, 1H), 4.62(d, 1H), 7.16(m, 1H), 7,23(d, 1H), 7.42(d, 1H), 7.48(s, 1H), 7.74(d, 2H), 8.49(m, 1H). LRMS: m/z (TSP$^+$) 473, 475 [MH$^+$] Microanalysis found: C, 62.66; H, 6.21; N, 8.80. C$_{25}$H$_{29}$Cl$_2$N$_3$O$_2$; 0.1CH$_2$Cl$_2$ requires C,62.43; H, 6.09; N, 8.70%. |

| Example | R | Yield (%) | Data |
|---|---|---|---|
| 21[2d] | 4-hydroxy-4-phenylpiperidine | 15 white foam | ¹Hnmr (CDCl₃, 400MHz) δ: 1.68(m, 2H), 1.91–2.16(m, 5H), 2.16–2.24(m, 2H), 2.24–2.40(m, 4H), 2.53–2.73(m, 3H), 3.95(d, 1H), 4.70(d, 1H), 7.14(m, 1H), 7.27(m, 2H), 7.36(m, 2H), 7.41(d, 1H), 7.45(d, 2H), 7.50(s, 1H), 7.71(m, 2H), 8.48(d, 1H). LRMS: m/z (TSP⁺) 425.1, 526.1 [MH⁺] |
| 22[3e] | 4-(4-fluorophenyl)-4-hydroxypiperidine | 64 white foam | ¹Hnmr (CDCl₃, 400MHz) δ: 1.38–1.78(m, 3H), 1.85–2.43(m, 11H), 2.51–2.78(m, 3H), 3.98(d, 1H), 4.72(d, 1H), 7.02(m, 2H), 7.15(dd, 1H), 7.25(d, 1H), 7.42(m, 3H), 7.51(s, 1H), 7.73(m, 2H), 8.48(d, 1H). LRMS: m/z (TSP⁺) 542.1, 544.1 [MH⁺] Microanalysis found: C, 63.55; H, 5.87; N, 7.48. $C_{29}H_{30}Cl_2FN_3O_2$; 0.3H₂O requires C, 63.58; H, 5.63; N, 7.67%. |
| 23[f] | 4-ethyl-4-hydroxypiperidine | 77 white foam | ¹Hnmr (CDCl₃, 400MHz) δ: 0.80(t, 3H), 1.42(m, 4H), 1.58(m, 3H), 1.95–2.02(m, 3H), 2.17(m, 4H), 2.25(m, 2H), 2.50(m, 3H), 3.88(d, 1H), 4.60(d, 1H), 7.10(dd, 1H), 7.18(d, 1H), 7.38(d, 1H), 7.42(s, 1H), 7.64(m, 2H), 8.42(d, 1H). LRMS: m/z (TSP⁺) 476.2, 478.2 [MH⁺] |
| 24[g] | spiro[isobenzofuran-1(3H),4'-piperidine] | 46 clear oil | ¹Hnmr (CDCl₃, 400MHz) δ: 1.65(m, 2H), 1.82(m, 2H), 1.92–2.36(m, 9H), 2.58(m, 1H), 2.63(m, 2H), 3.90(d, 1H), 4.60(d, 1H), 4.98(s, 2H), 7.04(m, 1H), 7.14(m, 2H), 7.20(m, 3H), 7.39(d, 1H), 7.45(s, 1H), 7.66(s, 2H), 8.45(d, 1H). LRMS: m/z (TSP⁺) 536.2, 538.2 [MH⁺] |
| 25[h] | 3-oxaspiro[isobenzofuran-1(3H),4'-piperidine] | 20 white foam | ¹Hnmr (CDCl₃, 400MHz) δ: 1.60(d, 2H), 1.99(m, 4H), 2.16(m, 2H), 2.20–2.40(m, 5H), 2.58(m, 1H), 2.72(m, 2H), 3.95(d, 1H), 4.61(d, 1H), 7.14(m, 1H), 7.21(m, 1H), 7.32(d, 1H), 7.40(d, 1H), 7.47(m, 2H), 7.61(dd, 1H), 7.66(m, 2H), 7.81(d, 1H), 8.46(d, 1H). LRMS: m/z (TSP⁺) 550.2, 552.2 [MH⁺] |

[1] = Isolated as the dihydrochloride salt
[2] = Free base of the aldehyde used
[3] = Tetrahydrofuran was used as the reaction solvent Starting amines:
[a] = benzylamine
[b] = phenethylamine
[c] = 7-oxa-2-azaspiro[3.5]nonane p-toluenesulphinate from preparation 38
[d] = 4-phenyl-4-piperidinol
[e] = 4-(4-fluorophenyl)-4-piperidinol
[f] = 4-ethyl-4-piperidinol from preparation 56
[g] = spiro[isobenzofuran-1(3H),4'-piperidine] prepared as in EP 630887
[h] = 3-oxaspiro[isobenzofuran-1(3H),4'-piperidine] prepared as in EP 630887

EXAMPLES 26 TO 31

The following examples of general structure:

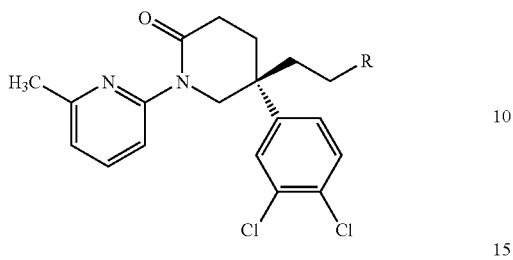

were prepared from the aldehyde hydrochloride from preparation 12b and the appropriate amine, following the procedure described in example 17.

| Example | R | Yield (%) | Data |
|---|---|---|---|
| 26[a] | ![azetidine-tetrahydropyran] | 29 white foam | $^1$Hnmr (CDCl$_3$, 400MHz) δ: 1.14(dq, 2H), 1.45(m, 2H), 1.57(m, 1H), 1.63–1.82(m, 4H), 2.00–2.18(m, 2H), 2.18–2.34(m, 2H), 2.56(m, 2H), 2.66(m, 2H), 3.26(m, 4H), 3.85(d, 1H), 3.94(m, 2H), 4.52(d, 1H), 7.00(d, 1H), 7.21(d, 1H), 7.40(d, 2H), 7.59(m, 2H). LRMS: m/z (TSP$^+$) 502.1, 504.1 [MH$^+$] Microanalysis found: C, 63.30; H, 6.68; N, 8.16. C$_{27}$H$_{33}$Cl$_2$N$_3$O$_2$; 0.15CH$_2$Cl$_2$ requires C, 63.29; H, 6.51; N, 8.16%. |
| 27[b] | ![azetidine-spiro-tetrahydropyran] | 50 white foam | $^1$Hnmr (CDCl$_3$, 400MHz) δ: 1.62–1.88(m, 6H), 2.07–2.39(m, 5H), 2.58(m, 4H), 2.90(m, 4H), 3.58(m, 4H), 3.90(d, 1H), 4.58(d, 1H), 7.01(d, 1H), 7.24(d, 1H), 7.42(d, 2H), 7.60(m, 2H). LRMS: m/z (ES$^+$) 488, 490 [MH$^+$] Microanalysis found: C, 62.96; H, 6.50; N, 8.45. C$_{26}$H$_{31}$N$_3$O$_2$Cl$_2$; 0.1CH$_2$Cl$_2$ requires C, 63.08; H, 6.33; N, 8.46% |
| 28[c] | ![piperidine-pyridine] | 51 clear oil | $^1$Hnmr (CDCl$_3$, 400MHz) δ: 1.68(m, 2H), 1.82–2.04(m, 8H), 2.14(m, 2H), 2.26(m, 2H), 2.50(s, 3H), 2.58(m, 1H), 2.84(m, 2H), 3.90(d, 1H), 4.62(d, 1H), 6.96(d, 1H), 7.08(m, 2H), 7.22(m, 1H), 7.38(m, 2H), 7.58(m, 3H), 8.46(d, 1H). LRMS: m/z (TSP$^+$) 523.9, 525.9 [MH$^+$] |
| 29[d] | ![piperidine-methoxyphenyl] | 42 white foam | $^1$Hnmr (CDCl$_3$, 400MHz) δ: 1.65(m, 4H), 1.82–2.08(m, 5H), 2.18(m, 2H), 2.30(m, 2H), 2.40(m, 1H), 2.60(m, 1H), 2.90(m, 2H), 4.00(d, 1H), 4.66(d, 1H), 7.18(m, 4H), 7.28(m, 3H), 7.41(d, 1H), 7.52(s, 1H), 7.72(m, 2H), 8.50(d, 1H). LRMS: m/z (ES$^+$) 552, 554 [MH$^+$] |

-continued

| Example | R | Yield (%) | Data |
|---|---|---|---|
| 30[e] | ![structure] | 18 white solid | [1]Hnmr (CDCl$_3$, 400MHz) δ: 1.86–2.19(m, 8H), 2.34(m, 6H), 2.48(m, 5H), 3.86(m, 1H), 4.62(m, 1H), 5.15(bs, 2H), 6.98(m, 1H), 7.22(m, 2H), 7.34(m, 4H), 7.39(m, 2H), 7.57(m, 2H). LRMS: m/z (TSP$^+$) 566.1, 568.1 [MH$^+$] |
| 31[f] | ![structure] | 33 | [1]Hnmr (CDCl$_3$, 400MHz) δ: 1.96(m, 2H), 2.05(m, 1H), 2.16(m, 2H), 2.40(m, 3H), 2.50(m, 5H), 3.45(m, 2H), 3.90(d, 1H), 4.68(d, 1H), 6.58(d, 2H), 6.96(d, 1H), 7.22(s, 1H), 7.40(m, 3H), 7.58(d, 2H), 8.15(d, 1H). LRMS: m/z (TSP$^+$) 524.9, 526.9 [MH$^+$] |

[1]= the aldehyde from preparation 12a was used

Starting amines:

[a]= 3-tetrahydro-2H-pyran-4-ylazetidine from preparation 31

[b]= 7-oxa-2-azaspiro[3.5]nonane p-toluenesulphinate from preparation 38

[c]= 2-(4'-piperidinyl)pyridine as prepared in EP 630887

[d]= 4-phenylpiperidine

[e]= 4-phenyl-4-piperidinecarboxamide as prepared in WO 9426735

[f]= 1 (2-pyridinyl)piperazine

EXAMPLE 32

(5S)-5-(3,4-Dichlorophenyl)-1-(2-pyridinyl)-5-(2-{[2-(4-pyridinyloxy)ethyl]amino}ethyl)-2-piperidinone trihydrochloride

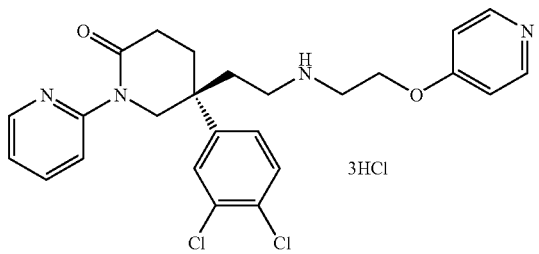

A solution of 2-(4-pyridinyloxy)ethylamine (EP 982322) (90.6 mg, 0.66 mmol) in dichloromethane (0.5 ml) was added to a solution of the aldehyde from preparation 11a (238.2 mg, 0.66 mmol) in dichloromethane (10 ml), and the solution stirred for 5 minutes. Sodium triacetoxyborohydride (139 mg, 0.66 mmol) was added and the reaction stirred for 1 hour. The reaction was washed with aqueous sodium bicarbonate solution (20 ml), brine (20 ml), then dried (MgSO$_4$) and concentrated under reduced pressure. The residue was purified by column chromatography on silica gel using dichloromethane:methanol:0.88 ammonia (90:10:1) as eluant. The product was dissolved in a minimum volume of dichloromethane, 1N ethereal hydrochloric acid added, and the mixture evaporated under reduced pressure to afford the title compound as a white foam, 170 mg.

[1]Hnmr (CD$_3$OD, 400 MHz) δ: 2.24–2.47 (m, 3H), 2.47–2.60 (m, 2H), 2.77–2.92 (m, 2H), 3.01 (m, 1H), 3.73 (s, 2H), 4.29 (d, 1H), 4.45 (d, 1H), 4.64 (s, 2H), 745 (d, 1H), 7.60 (m, 3H), 7.73 (s, 1H), 7.80 (dd, 1H), 8.07 (d, 1H), 8.61 (d, 2H), 8.72 (d, 2H).

LRMS: m/z (TSP$^+$) 485.1, 487.2 [MH$^+$]

Microanalysis found: C, 45.06; H, 5.32; N, 8.19. C$_{25}$H$_{26}$Cl$_2$N$_3$O$_2$;3HCl;4H$_2$O requires C, 45.03; H, 5.59; N, 8.40%.

EXAMPLES 33 TO 40

The following examples of general structure:

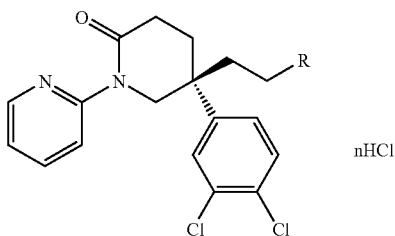

were prepared from the aldehyde from preparation 11a, and the apropriate amines, following a similar procedure to that described in example 32.

| Example | R | Yield (%) | Data |
|---|---|---|---|
| 33[1a] | NH-CH2CH2-O-(pyridin-3-yl) | 53 white solid | ¹Hnmr (CD₃OD, 400MHz) δ: 2.19–2.49(m, 3H), 2.49–2.65(m, 2H), 2.88–2.97(m, 2H), 2.97–3.17(m, 1H), 3.52(s, 2H), 4.28(d, 1H), 4.46(d, 1H), 4.57(m, 2H), 7.47(d, 1H), 7.60(d, 1H), 7.73(s, 1H), 7.80(d, 1H), 8.00–8.17(m, 2H), 8.32(d, 1H), 8.59–8.67(m, 3H), 8.70(s, 1H). Microanalysis found: C, 46.30; H, 5.29; N, 8.39. C₂₅H₂₆Cl₂N₃O₂; 3HCl; 3H₂O requires C, 46.28; H, 5.44; N, 8.64%. |
| 34[1b] | NH-CH2CH2-O-(pyridin-2-yl) | 48 white solid | ¹Hnmr (CD₃OD, 400MHz) δ: 2.23–2.45(m, 3H), 2.45–2.62(m, 2H), 2.79–2.95(m, 2H), 3.00(t, 1H), 3.50(m, 2H), 4.28(d, 1H), 4.46(d, 1H), 4.69(m, 2H), 7.29–7.41(m, 2H), 7.46(d, 1H), 7.60(d, 1H), 7.73(s, 1H), 7.80(dd, 1H), 8.06(d, 1H), 8.23(dd, 1H), 8.35(d, 1H), 8.52–8.69(m, 2H). LRMS: m/z (TSP⁺) 485.2, 487.2 [MH⁺] Microanalysis found: C, 45.82; H, 5.33; N, 8.25. C₂₅H₂₆Cl₂N₃O₂; 3HCl; 3.5H₂O requires C, 45.64; H, 5.52; N, 8.52%. |
| 35[2c] | NH-CH2-(1-methyl-2-oxo-1,2-dihydropyridin-4-yl) | 39 white foam | ¹Hnmr (CDCl₃, 400MHz) δ: 1.80–2.02(m, 2H), 2.12(m, 1H), 2.20–2.36(m, 3H), 2.40(m, 1H), 2.57(m, 1H), 3.35–3.55(m, 5H), 3.91(d, 1H), 4.59(d, 1H), 6.02(d, 1H), 6.38(s, 1H), 7.06–7.23(m, 3H), 7.38(d, 1H), 7.43(s, 1H), 7.61–7.77(m, 2H), 8.47(d, 1H). LRMS: m/z (TSP⁺) 485.3, 487.3 [MH⁺] |
| 36[1d] | NH-CH2CH2CH2-(morpholin-4-yl) | 62 white foam | ¹Hnmr (CD₃OD, 400MHz) δ: 2.17(m, 2H), 2.21–2.40(m, 4H), 2.53(m, 2H), 2.78(m, 2H), 2.92(m, 1H), 3.06(t, 1H), 3.17(t, 2H), 3.26(m, 4H), 3.83(m, 2H), 4.04(m, 2H), 4.20(m, 1H), 4.48(m, 1H), 7.44(d, 1H), 7.60(d, 1H), 7.68(dd, 1H), 7.71(s, 1H), 7.93(d, 1H), 8.40(dd, 1H), 8.59(d, 1H). LRMS: m/z (TSP⁺) 491.2, 493.2 [MH⁺] |
| 37[1e] | NH-CH(CH3)-phenyl | 52 white solid | ¹Hnmr (CD₃OD, 400MHz) δ: 1.60(d, 3H), 2.04–2.33(m, 3H), 2.37–2.43(m, 3H), 2.61–2.83(m, 2H), 4.15(d, 1H), 4.28(q, 1H), 4.40(d, 1H), 7.24–7.40(m, 6H), 7.46(d, 1H), 7.58(s, 1H), 7.61(dd, 1H), 7.82(d, 1H), 8.32(dd, 1H), 8.57(d, 1H). LRMS: m/z (TSP⁺) 468.1, 470.1 [MH⁺] |

-continued

| Example | R | Yield (%) | Data |
|---|---|---|---|
| 38[1],[f] | ![structure: NH-CH(CH3)-phenyl] | 71 white solid | ¹Hnmr (CD$_3$OD, 400MHz) δ: 1.60(d, 3H), 2.05–2.20(m, 1H), 2.20–2.40(m, 2H), 2.40–2.57(m, 2H), 2.57–2.66(m, 2H), 2.70–2.81(m, 1H), 4.18(d, 1H), 4.35(m, 2H), 7.23–7.42(m, 6H), 7.46(d, 1H), 7.60(s, 1H), 7.75(dd, 1H), 7.65(d, 1H), 8.50(dd, 1H), 8.57(d, 1H). LRMS: m/z (TSP$^+$) 468.1, 470.1 [MH$^+$] Microanalysis found: C, 53.31; H, 5.69; N, 6.82. C$_{26}$H$_{27}$Cl$_2$N$_3$O; 2HCl; 2.3H$_2$O requires C, 53.58; H, 5.81; N, 7.21%. |
| 39[g] | ![azetidine-CH2-N(CH3)-C(O)CH3] | | ¹Hnmr (CD$_3$OD, 400MHz) δ: 2.00–2.27(m, 6H), 2.37(m, 1H), 2.35(m, 1H), 2.52(m, 2H), 2.70–3.24(m, 6H), 3.55(m, 1H), 3.68(m, 1H), 3.81(m, 2H), 4.03(m, 1H), 4.21(m, 2H), 4.42(m, 1H), 7.43(m, 1H), 7.60(m, 1H), 7.70(m, 1H), 7.81(m, 1H), 8.07(m, 1H), 8.60(m, 1H). LRMS: m/z (TSP$^+$) 489.1, 491.2 [MH$^+$] |
| 40[h] | ![N-piperidine-C(O)OCH2CH3] | 46 white solid | ¹Hnmr (CDCl$_3$, 400MHz) δ: 1.25(m, 3H), 2.04–2.72(m, 14H), 2.80(m, 2H), 3.35(m, 1H), 4.20(m, 3H), 4.80(m, 1H), 7.20(m, 1H), 7.39(m, 1H), 7.50(m, 2H), 7.80(m, 2H), 8.50(m, 1H). LRMS: m/z (TSP$^+$) 504.1, 506.1 [MH$^+$] |

[1] = aldehyde hydrochloride was used  
[2] = isolated as the free base

Starting amines:  
[a] = 2-(3-pyridinyloxy)ethylamine as prepared in WO 0071520  
[b] = 2-(2-pyridinyloxy)ethylamine as prepared in Tetrahedron, 44, 1988, 91  
[c] = 4-(aminomethyl)-1-methyl-2(1H)-pyridinone from preparation 21  
[d] = N-(3-aminopropyl)morpholine  
[e] = L-(−)-alpha-methylbenzylamine  
[f] = R-(+)-1-phenylethylamine  
[g] = N-(3-azetidinylmethyl)-N-methylacetamide from preparation 25  
[h] = ethyl 4-piperidinecarboxylate

EXAMPLES 41 TO 47

The following examples of general structure:

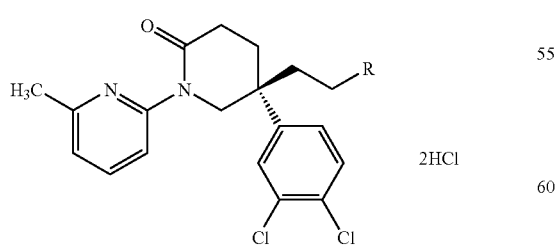

were prepared from the aldehyde from preparation 12a, and the appropriate amines, following a similar procedure to that described in example 32.

| Example | R | Yield (%) | Data |
|---|---|---|---|
| 41[a] | (CH₃, NH, phenyl — α-methylbenzyl, one stereochemistry) | 53 white powder | ¹Hnmr (CD₃OD, 400MHz) δ: 1.58(d, 3H), 2.07–2.28(m, 3H), 2.35–2.50(m, 3H), 2.60–2.75(m, 5H), 4.17(d, 1H), 4.20–4.32(m, 2H), 7.22–7.39(m, 6H), 7.48(d, 1H), 7.53(s, 1H), 7.67(d, 1H), 7.76(d, 1H), 8.44(dd, 1H). LRMS: m/z (TSP⁺) 482.1, 484.1 [MH⁺] Microanalysis found: C, 53.87; H, 5.68; N, 6.82. $C_{27}H_{29}Cl_2N_3O$; 2HCl; 2.35H₂O requires C, 54.25; H, 6.02; N, 7.03%. |
| 42[b] | (CH₃, NH, phenyl — α-methylbenzyl, other stereochemistry) | 24 white foam | ¹Hnmr (CD₃OD, 400MHz) δ: 1.58(m, 3H), 2.08(m, 1H), 2.18–2.32(m, 2H), 2.37–2.61(m, 4H), 2.61–2.75(m, 4H), 4.13(d, 1H), 4.20–4.35(m, 2H), 7.23–7.39(m, 6H), 7.47(d, 1H), 7.57(s, 1H), 7.62(d, 1H), 7.69(d, 1H), 8.39(dd, 1H). LRMS: m/z (TSP⁺) 482.1, 484.0 [MH⁺] Microanalysis found: C, 53.36; H, 5.95; N, 6.55. $C_{27}H_{29}Cl_2N_3O$; 2HCl; 3.0H₂O requires C, 53.24; H, 6.12; N, 6.90%. |
| 43[c] | NH-(CH₂)₃-N(morpholine) | 26 white solid | ¹Hnmr (CD₃OD, 400MHz) δ: 2.11(m, 2H), 2.20–2.37(m, 4H), 2.41–2.56(m, 2H), 2.68–2.78(m, 4H), 2.86(m, 1H), 3.03(t, 2H), 3.10(t, 2H), 3.21(m, 2H), 3.46(m, 2H), 3.79(t, 2H), 4.01(m, 2H), 4.17(d, 1H), 4.37(d, 1H), 7.42(d, 1H), 7.55–7.61(m, 2H), 7.72(m, 2H), 8.55(dd, 1H). LRMS: m/z (ES⁺) 505, 507 [MH⁺] |
| 44[d] | N-methylpyrrolidine-S-NHC(O)CH₃ | 47 white foam | ¹Hnmr (CDCl₃, 400MHz) δ: 1.52(m, 2H), 1.88(s, 3H), 1.92–2.36(m, 10H), 2.51–2.60(m, 5H), 2.79(m, 1H), 3.86(d, 1H), 4.35(bs, 1H), 4.68(d, 1H), 7.00(d, 1H), 7.21(d, 1H), 7.41(m, 2H), 7.56–7.63(m, 2H). LRMS: m/z (TSP⁺) 489.1, 491.1 [MH⁺] Microanalysis found: C, 60.17; H, 6.19; N, 11.11. $C_{25}H_{30}Cl_2N_4O_2$ requires C, 60.24; H, 6.27; N, 11.24%. |
| 45[e] | N-methylpyrrolidine-R-NHC(O)CH₃ | 55 white foam | ¹Hnmr (CDCl₃, 400MHz) δ: 1.53(m, 2H), 1.91(s, 3H), 1.98–2.43 (m, 10H), 2.48–2.66(m, 5H), 2.84(m, 1H), 3.92(d, 1H), 4.38(bs, 1H), 4.60(d, 1H), 7.02(d, 1H), 7.24(d, 1H), 7.44(m, 2H), 7.57–7.66(m, 2H). LRMS: m/z (TSP⁺) 489.2, 491.2 [MH⁺] Microanalysis found: C, 59.52; H, 6.23; N, 10.82. $C_{25}H_{30}Cl_2N_4O_2$; 0.8H₂O requires C, 59.60; H, 6.32; N, 11.12%. |

-continued

| Example | R | Yield (%) | Data |
|---|---|---|---|
| 46[1f] |  | 51 white foam | [1]Hnmr (CDCl$_3$, 400MHz) δ (mixture of diastereoisomers): 1.55(m, 2H), 1.63–2.33(m, 12H), 2.37–2.59(m, 5H), 2.77, 2.86(d, 3H, 60:40), 3.86(2xd, 1H), 4.30, 5.16(m, 1H, 40:60), 4.57(2xd, 1H), 6.96(d, 1H), 7.19(d, 1H), 7.37(d, 2H), 7.50–7.60(m, 2H). LRMS: m/z (ES$^+$) 503, 505 [MH$^+$] |
| 47[1g] |  | 66 white foam | [1]Hnmr (CDCl$_3$, 300MHz) δ: 1.58(m, 2H), 1.95(d, 2H), 2.08(s, 3H), 2.12–2.40(m, 8H), 2.58(s, 3H), 3.40(t, 2H), 3.56(t, 2H), 3.92(d, 1H), 4.71(d, 1H), 7.01(d, 1H), 7.23(m, 1H), 7.43(t, 2H), 7.61(m, 2H). LRMS: m/z (TSP$^+$) 489.2, 491.2 [MH$^+$] Microanalysis found: C, 59.66; H, 6.29; N, 10.95. $C_{25}H_{30}Cl_2N_4O_2$; 0.7H$_2$O requires C, 59.81;H, 6.30; N, 11.16%. |

[1] = product isolated as the free base
Starting amines:
[a] = L-(−)-alpha-methylbenzylamine
[b] = R-(+)-1-phenylethylamine
[c] = N-(3-aminopropyl)morpholine
[d] = (3S)-(−)-3-acetamidopyrrolidine
[e] = (3R)-(+)-3-acetamidopyrrolidine
[f] = 3-(N-acetyl-N-methylamino)pyrrolidine
[g] = 1-acetylpiperazine

EXAMPLE 48

(5S)-5-(3,4-Dichlorophenyl)-5-[2-[(2-fluorobenzyl)amino]ethyl]-1-(2-pyridinyl)-2-piperidinone dihydrochloride

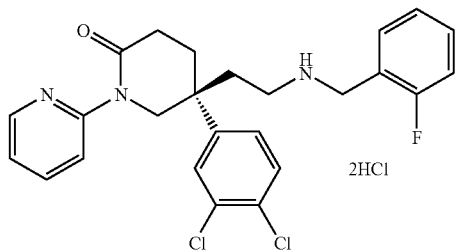

2-Fluorobenzylamine (90 μl, 0.79 mmol) was added to a solution of the aldehyde hydrochloride from preparation 11b (250 mg, 0.63 mmol), in dichloromethane (5 ml), and the solution stirred for 5 minutes. Sodium triacetoxyborohydride (132.6 mg, 0.63 mmol) was added and the reaction stirred for a further 10 minutes. Saturated aqueous sodium bicarbonate solution (3 ml) was added, the mixture stirred for 10 minutes, then filtered through a phase separation filter, and the organic filtrate evaporated. The residue was purified by Biotage® column chromatography on silica gel using dichloromethane:methanol:0.88 ammonia (95:5:0.5) as the eluant. The product was redissolved in dichloromethane, 1N ethereal hydrochloric acid added, and the solvents evaporated under reduced pressure to afford the title compound as a white solid, 77.4 mg.

[1]Hnmr (CD$_3$OD, 400 MHz) δ: 2.10–2.36 (m, 3H), 2.36–2.53 (m, 2H), 2.60–2.80 (m, 2H), 2.92 (m, 1H), 4.13 (d, 1H), 4.18 (s, 2H), 4.42 (d, 1H), 7.12–7.23 (m, 2H), 7.37–7.50 (m, 3H), 7.54 (m, 2H), 7.67 (s, 1H), 7.79 (d, 1H), 8.20 (m, 1H), 8.55 (m, 1H).

LRMS: m/z (TSP$^+$) 472.1, 474.1 [MH$^+$]

Microanalysis found: C, 51.92; H, 5.17; N, 7.00. $C_{25}H_{24}Cl_2FN_3O$.2HCl;1.6H$_2$O requires C, 52.30; H, 4.78; N, 7.32%.

EXAMPLES 49 TO 53

The following compounds of general structure:

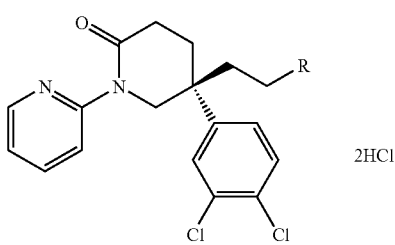

were prepared from the aldehyde hydrochloride from preparation 11b and the corresponding commercially available amine, following the procedure described in example 48.

| Example | R | Yield (%) | Data |
|---|---|---|---|
| 49[a] | 3-fluorobenzyl-NH- | 25 | ¹Hnmr (CD$_3$OD, 400MHz) δ: 2.12–2.36(m, 3H), 2.38–2.55(m, 2H), 2.64–2.80(m, 2H), 2.85(m, 1H), 4.12(d, 1H), 4.19(s, 2H), 4.50(d, 1H), 7.16–7.23(m, 3H), 7.40(m, 2H), 7.50(m, 1H), 7.59(d, 1H), 7.70(d, 1H), 7.74(d, 1H), 8.16(m, 1H), 8.50(m, 1H). LRMS: m/z (TSP⁺) 472.1, 474.1 [MH⁺] Microanalysis found: C, 52.42; H, 5.22; N, 7.03. C$_{25}$H$_{24}$Cl$_2$FN$_3$O; 2HCl;1.5H$_2$O requires C, 52.46; H, 4.76; N, 7.34% |
| 50[b] | 4-fluorobenzyl-NH- | 31 | ¹Hnmr (CD$_3$OD, 400MHz) δ: 2.17–2.40(m, 3H), 2.40–2.57(m, 2H), 2.65–2.82(m, 2H), 2.91(m, 1H), 4.09(s, 2H), 4.20(d, 1H), 4.41(d, 1H), 7.10(m, 2H), 7.32–7.49(m, 3H), 7.57(d, 1H), 7.66(m, 2H), 7.91(d, 1H), 8.41(dd, 1H), 8.58(d, 1H). LRMS: m/z (TSP⁺) 472.1, 474.2 [MH⁺] Microanalysis found: C, 51.12; H, 5.04; N, 6.76. C$_{25}$H$_{24}$Cl$_2$FN$_3$O.2HCl;2.5H$_2$O requires C, 50.86; H, 4.95; N, 7.12% |
| 51[c] | 2-methoxybenzyl-NH- | 16 | ¹Hnmr (CD$_3$OD, 400MHz) δ: 2.19–2.40(m, 3H), 2.43–2.60(m, 2H), 2.68–2.83(m, 2H), 2.83–2.98(m, 1H), 3.85(s, 3H), 4.15(s, 2H), 4.24(d, 1H), 4.43(d, 1H), 6.90–7.13(m, 2H), 7.31(d, 1H), 7.39–7.50(m, 2H), 7.59(d, 1H), 7.70(s, 1H), 7.77(dd, 1H), 8.00(d, 1H), 8.52(dd, 1H), 8.60(d, 1H). LRMS: m/z (TSP⁺) 484.2, 486.2 [MH⁺] Microanalysis found: C, 51.60; H, 5.56;N, 6.72. C$_{26}$H$_{27}$Cl$_2$N$_3$O$_2$; 2HCl; 2.5H$_2$O requires C, 51.84; H, 5.69; N, 6.97% |
| 52[d] | 3-methoxybenzyl-NH- | 11 | ¹Hnmr (CD$_3$OD, 400MHz) δ: 2.19–2.40(m, 3H), 2.42–2.60(m, 2H), 2.71–2.86(m, 2H), 2.92(m, 1H), 3.81(s, 3H), 4.10(s, 2H), 4.22(d, 1H), 4.43(d, 1H), 6.90–7.11(m, 3H), 7.33(dd, 1H), 7.42(d, 1H), 7.59(d, 1H), 7.69(s, 1H), 7.75(dd, 1H), 7.99(d, 1H), 8.48(dd, 1H), 8.60(d, 1H). LRMS: m/z (TSP⁺) 484.2, 486.1 [MH⁺] Microanalysis found: C, 52.10; H, 5.46; N,6.97. C$_{26}$H$_{27}$Cl$_2$N$_3$O$_2$; 2HCl; 2.5H$_2$O requires C, 51.84; H, 5.69; N, 6.97% |

-continued

| Example | R | Yield (%) | Data |
|---|---|---|---|
| 53[e] | 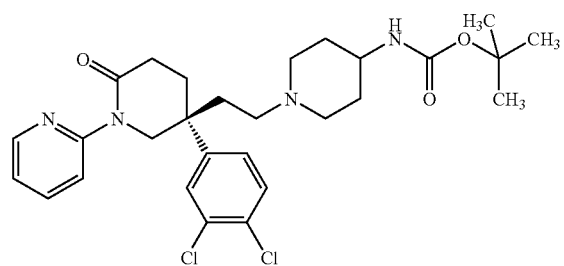 | 8 | [1]Hnmr (CD$_3$OD, 400MHz) δ: 2.13–2.40(m, 3H), 2.40–2.58(m, 2H), 2.65–2.82(m, 2H), 2.82–2.95(m, 1H), 3.80(s, 3H), 4.05(s, 2H), 4.20(d, 1H), 4.44(d, 1H), 6.93(d, 2H), 7.32(d, 2H), 7.42(d, 1H), 7.59(d, 1H), 7.63–7.76(m, 2H), 7.92(d, 1H), 8.40(dd, 1H), 8.59(d, 1H). LRMS: m/z (TSP$^+$) 484.2, 486.2 [MH$^+$] Microanalysis found: C, 51.14; H, 5.70; N, 6.65. C$_{26}$H$_{27}$Cl$_2$N$_3$O$_2$;2HCl; 3H$_2$O requires C, 51.07; H, 5.77; N, 6.91% |

Starting amines:
[a]= 3-fluorobenzylamine
[b]= 4-fluorobenzylamine
[c]= 2-methoxybenzylamine
[d]= 3-methoxybenzylamine
[e]= 4-methoxybenzylamine

EXAMPLE 54 tert-butyl 1-{2-[(3S)-3-(3,4-dichlorophenyl)-6-oxo-1-(2-pyridinyl)piperidinyl]ethyl}-4-piperidinylcarbamate

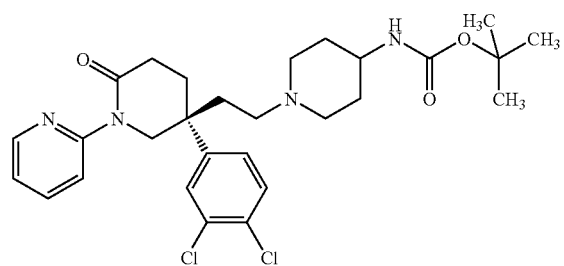

Triethylamine (0.15 ml, 1.1 mmol) was added to a solution of the aldehyde hydrochloride from preparation 11b (400 mg, 1.0 mmol) in dichloromethane (5 ml), and the solution stirred for 5 minutes. Tert-butyl 4-piperidinylcarbamate (240 mg, 1.2 mmol) and sodium triacetoxyborohydride (295 mg, 1.4 mmol) were then added, and the reaction stirred at room temperature for 3 days. Methanol was added, the mixture stirred for 15 minutes, then evaporated under reduced pressure. The residue was purified by column chromatography on silica gel using dichloromethane:methanol:0.88 ammonia (90:10:1) as eluant to give the title compound as a white foam, 580 mg.

[1]Hnmr (CDCl$_3$, 400 MHz) δ: 1.28 (m, 2H), 1.39 (s, 9H), 1.78–2.00 (m, 7H), 2.11 (m, 2H), 2.27 (m, 2H), 2.56 (m, 1H), 2.62 (m, 2H), 3.36 (m, 1H), 3.88 (d, 1H), 4.31 (bs, 1H), 4.58 (d, 1H), 7.10 (dd, 1H), 7.17 (d, 1H), 7.36 (d, 1H), 7.43 (d, 1H), 7.67 (s, 2H), 8.45 (d, 1H).

LRMS: m/z (ES$^+$) 547, 549 [MH$^+$]

Microanalysis found: C, 71.17; H, 6.63; N, 10.23, C$_{28}$H$_{36}$Cl$_2$N$_4$O$_3$ requires C, 61.42; H, 6.63; N, 10.23%.

EXAMPLE 55

(5S)-5-(3,4-Dichlorophenyl)-1-(2-pyridinyl)-5-{2-[(4-pyridinylmethyl)amino]ethyl}-2-piperidinone hydrochloride

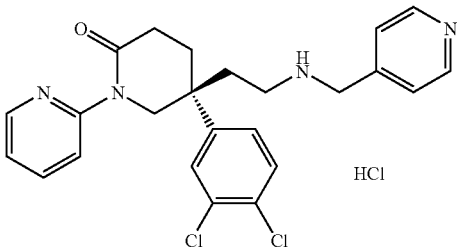

The aldehyde from preparation 11a (192 mg, 0.53 mmol) and 4-(aminomethyl)-pyridine (54 μl, 0.53 mmol) in dichloromethane (10 ml) were stirred together for 5 minutes, then acetic acid (61 μl, 1.06 mmol) and sodium triacetoxyborohydride (224 mg, 1.06 mmol) were added, and the reaction stirred at room temperature for 18 hours. The mixture was washed with aqueous 1N sodium hydroxide solution (5 ml), dried (MgSO$_4$) and concentrated under reduced pressure. The residual oil was purified by column chromatography on silica gel using dichloromethane:methanol:0.88 ammonia (95:5:0.5) as eluant, to give a sticky foam. This product was dissolved in dichloromethane (2 ml), treated with ethereal hydrochloric acid and the mixture evaporated under reduced pressure to give the title compound as a white powder, 208 mg.

[1]Hnmr (CD$_3$OD, 400 MHz) δ: 2.30–2.55 (m, 5H), 2.80 (m, 1H), 2.92 (m, 1H), 3.09 (m, 1H), 4.21 (d, 1H), 4.50 (d, 1H), 4.52 (s, 2H), 7.49 (dd, 1H), 7.61 (d, 1H), 7.67 (dd, 1H), 7.75 (s, 1H), 7.92 (d, 1H), 8.22 (d, 2H), 8.38 (dd, 1H), 8.59 (d, 1H), 8.95 (d, 2H).

LRMS: m/z (TSP$^+$) 455.0, 457.1 [MH$^+$]

Microanalysis found: C, 47.68; H, 5.07; N, 9.17. C$_{24}$H$_{24}$Cl$_2$N$_4$O; 3HCl; 0.5H$_2$O;0.5CH$_2$Cl$_2$ requires C, 47.68; H, 5.07; N, 9.17%.

EXAMPLES 56 TO 57

The compounds of the following general structure:

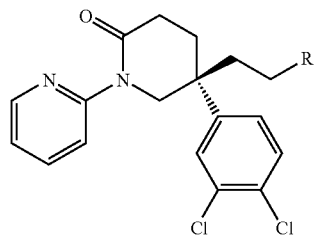

were prepared form the aldehyde from preparation 11a, and the appropriate amine, following a similar procedure to that described in example 55.

from preparation 11a (400 mg, 1 mmol) in dichloromethane (10 ml) and the solution stirred at room temperature for 30 minutes. Sodium triacetoxyborohydride (212 mg, 2 mmol) was added and the reaction stirred at room temperature for 4 hours. The reaction was quenched with methanol (10 ml), the solution stirred for 10 minutes, then concentrated under reduced pressure. The crude product was purified by column chromatography on silica gel using dichloromethane:methanol:0.88 ammonia (90:10:1) as eluant to afford the title compound as a colourless foam, 162 mg.

$^1$Hnmr (CDCl$_3$, 400 MHz) δ: 1.74–2.17 (m, 11H), 2.26 (m, 2H), 2.55 (m, 1H), 2.75 (m, 2H), 3.42 (m, 1H), 3.86 (dd, 1H), 4.61 (dd, 1H), 5.21 (bs, 1H), 5.38 (bs, 1H), 7.08 (m, 1H), 7.19 (m, 1H), 7.36 (m, 1H), 7.42 (s, 1H), 7.62 (m, 2H), 8.42 (m, 1H).

LRMS: m/z (ES$^+$) 475, 477 (MH$^+$)

| | R | Yield (%) | Data |
|---|---|---|---|
| 56[1a] | ![NH-CH2-pyridin-2-yl] | 59 white solid | $^1$Hnmr(CD$_3$OD, 400MHz) δ: 2.21–2.60(m, 5H), 2.75–2.95(m, 2H), 3.05(m, 1H), 4.26(d, 1H), 4.40(s, 2H), 4.43(d, 1H), 7.42(d, 1H), 7.58(d, 1H), 7.65(d, 1H), 7.71(m, 2H), 7.76(m, 1H), 8.01(d, 1H), 8.13(dd, 1H), 8.56(dd, 1H), 8.60(d, 1H), 8.70(d, 1H). LRMS: m/z (TSP$^+$) 455.0, 457.1 [MH$^+$] Microanalysis found: C, 46.29; H, 5.27; N, 8.80. C$_{24}$H$_{24}$Cl$_2$N$_4$O; 3HCl;2H$_2$O requires C, 46.58; H, 5.05; N, 9.05% |
| 57[b] | ![NH-CH2CH2-pyridin-4-yl] | 58 yellow solid | $^1$Hnmr(CD$_3$OD, 300MHz) δ: 2.20–2.40(m, 5H), 2.79(m, 2H), 2.97(m, 1H), 3.59(m, 4H), 4.23(m, 1H), 4.48(m, 1H), 7.48(m, 1H), 7.61(m, 1H), 7.70(m, 1H), 7.76(m, 1H), 7.96(m, 1H), 8.10(m, 2H), 8.41(m, 1H), 8.60(m, 1H), 8.82(m, 2H). Microanalysis found: C, 46.46; H, 5.71; N, 8.78. C$_{25}$H$_{26}$Cl$_2$N$_4$O; 3HCl; 3H$_2$O; 0.2CH$_2$Cl$_2$requires C, 46.58; H, 5.49; N, 8.62%. |

[1] = aldehyde hydrochloride from preparation 11b was used as the starting material
Starting amines:
[a] = 2-(aminoethyl)pyridine
[b] = 4-(2-aminoethyl)pyridine

EXAMPLE 58

1-{2-[(3S)-3-(3,4-Dichlorophenyl)-6-oxo-1-(2-pyridinyl)piperidinyl]ethyl}-4-piperidinecarboxamide

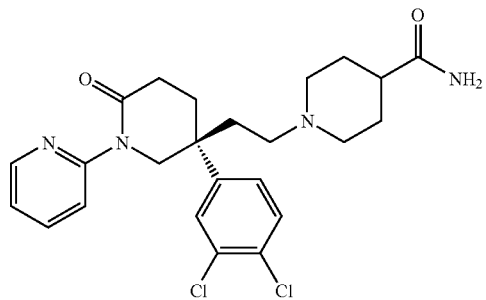

Isonipecotamide (128 mg, 1 mmol) and glacial acetic acid (120 mg, 2 mmol) were added to a solution of the aldehyde Microanalysis found: C, 57.95; H, 6.06; N, 11.02. C$_{24}$H$_{28}$Cl$_2$N$_4$O$_2$; H$_2$O requires C, 58.08; H, 6.06; N, 11.01%.

EXAMPLE 59

(5S)-5-{2-[(1-Acetyl-4-piperidinyl)amino]ethyl}-5-(3,4-dichlorophenyl)-1-(2-pyridinyl)-2-piperidinone

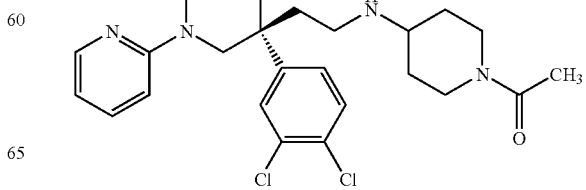

The title compound was prepared as a white foam in 71% yield, from the aldehyde from preparation 11a and the amine from preparation 22, following a similar procedure to that described in example 58.

$^1$Hnmr (CDCl$_3$, 400 MHz) δ: 1.10 (t, 2H), 1.70 (s, 2H), 1.85 (m, 1H), 1.92 (m, 1H), 2.00 (s, 3H), 2.10 (m, 1H), 2.25 (m, 3H), 2.40–2.70 (m, 4H), 2.95 (t, 1H), 3.65 (d, 1H), 3.90 (d, 1H), 4.30 (t, 1H), 4.55 (dd, 1H), 7.10 (dd, 1H), 7.19 (d, 1H), 7.38 (d, 1H), 7.45 (d, 1H), 7.68 (d, 2H), 8.45 (d, 1H).

LRMS: m/z (TSP$^+$) 489.1, 491.1 [MH$^+$]

Microanalysis found: C, 58.91; H, 6.27; N, 10.85. C$_{25}$H$_{30}$Cl$_2$N$_4$O$_2$; 0.3CH$_2$Cl$_2$ requires C, 59.07; H, 5.99; N, 10.88%.

EXAMPLE 60

(5S)-5-(3,4-Dichlorophenyl)-5-(2-{[2-(4-morpholinyl)ethyl]amino}ethyl)-1-(2-pyridinyl)-2-piperidinone trihydrochloride

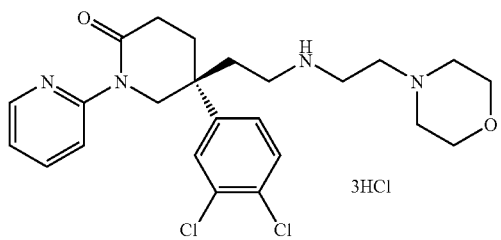

2-(4-Morpholinyl)ethylamine (970 mg, 7.5 mmol), acetic acid (10 drops), and sodium triacetoxyborohydride (500 mg, 2.4 mmol) were added consecutively to a solution of the aldehyde from preparation 11a (270 mg, 0.68 mmol), and the reaction stirred at room temperature for an hour. The mixture was washed with 1N sodium hydroxide solution, then brine, dried (MgSO$_4$) and concentrated under reduced pressure. The product was redissolved in dichloromethane, treated with 1N ethereal hydrochloric acid and the solution evaporated under reduced pressure to afford the title compound as a yellow solid, 220 mg.

$^1$Hnmr (CD$_3$OD, 300 MHz) δ: 2.35 (m, 3H), 2.54 (m, 2H), 2.83 (m, 2H), 2.98 (m, 1H), 3.23 (m, 2H), 3.42–3.66 (m, 6H), 3.87–4.12 (m, 4H), 4.23 (m, 1H), 4.48 (m, 1H), 7.48 (m, 1H), 7.61 (m, 1H), 7.75 (m, 2H), 7.98 (m, 1H), 8.47 (m, 1H), 8.61 (m, 1H).

LRMS: m/z (ES$^+$) 477, 479 [MH$^+$]

Microanalysis found: C, 44.94; H, 6.17; N, 8.72.

C$_{24}$H$_{30}$Cl$_2$N$_4$O$_2$;3HCl;2H$_2$O; 0.25CH$_2$Cl$_2$ requires C, 45.22; H, 5.87; N, 8.70%

EXAMPLE 61

(5S)-5-(3,4-Dichlorophenyl)-5-[2-(4-methoxy-1-piperidinyl)ethyl]-1-(2-pyridinyl)-2-piperidinone

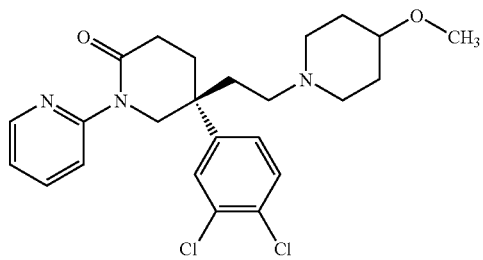

4-Methoxypiperidine (WO 9847876) (81 mg, 0.7 mmol) was added to a solution of the aldehyde hydrochloride from preparation 11b (200 mg, 0.5 mmol) in dichloromethane (4 ml) and triethylamine (100 μl, 0.7 mmol), and the solution stirred at room temperature for 10 minutes. Sodium triacetoxyborohydride (158 mg, 1.5 mmol) and acetic acid (6 μl, 2 mmol) were added and the reaction stirred at room temperature for 2 hours. The reaction was quenched with methanol, and the solution concentrated under reduced pressure. The crude product was purified by column chromatography on silica gel using an elution gradient of dichloromethane:methanol:0.88 ammonia (95:5:0 to 90:10:1) to give the title compound as a white foam, 182 mg.

$^1$Hnmr (CDCl$_3$, 400 MHz) δ: 1.57 (s, 2H), 1.85–2.11 (m, 7H), 2.24 (m, 4H), 2.55 (m, 3H), 3.19 (s, 1H), 3.24 (s, 3H), 3.85 (d, 1H), 4.58 (d, 1H), 7.06 (m, 1H), 7.18 (d, 1H), 7.36 (d, 1H), 7.41 (s, 1H), 7.62 (s, 2H), 7.42 (d, 1H).

LRMS: m/z (ES$^+$) 462, 464 [MH$^+$]

EXAMPLES 62 TO 72

The following examples of general structure:

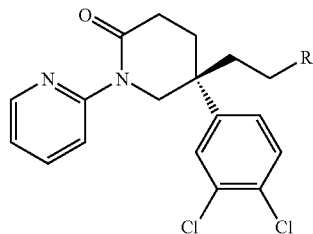

were prepared from the aldehyde hydrochloride from preparation 11b and the appropriate amines, following a similar procedure to that described in example 61.

| | R | Yield (%) | Data |
|---|---|---|---|
| 62[a] | 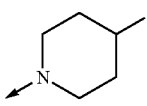 | 39 foam | $^1$Hnmr(CDCl$_3$, 400MHz) δ: 1.53(m, 2H), 1.81(m, 2H), 1.95(m, 5H), 2.11(m, 2H), 2.27(m, 2H), 2.57(m, 3H), 3.25(m, 1H), 3.32(s, 3H), 3.47(d, 2H), 3.51(d, 2H), 3.87(d, 1H), 4.58(d, 1H), 7.09(dd, 1H), 7.18(d, 1H), 7.35(d, 1H), 7.43(s, 1H), 7.65(s, 2H), 8.44(dd, 1H). LRMS: m/z (ES$^+$) 506, 508 [MH$^+$] |
| 63[b] | 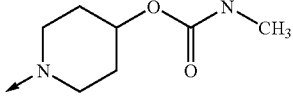 | 78 white foam | $^1$Hnmr(CDCl$_3$, 400MHz) δ: 1.66(m, 2H), 1.80(m, 2H), 1.88–1.98(m, 3H), 2.07(m, 4H), 2.27(m, 2H), 2.51(m, 3H), 2.72(s, 3H), 3.88(d, 1H), 4.51(s, 1H), 4.61(d, 2H), 7.09(dd, 1H), 7.18(d, 1H), 7.36(d, 1H), 7.44(s, 1H), 7.66(s, 2H), 8.44(dd, 1H). Microanalysis found: C, 58.27; H, 6.02; N, 10.61. C$_{25}$H$_{30}$Cl$_2$N$_4$O$_3$; 0.15CH$_2$Cl$_2$ requires C, 58.30; H, 5.89; N, 10.81% |
| 64[c] | 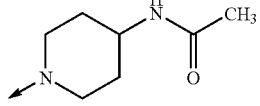 | 49 white foam | $^1$Hnmr(CDCl$_3$, 400MHz) δ: 1.30(m, 2H), 1.80–2.00(m, 10H), 2.14(m, 2H), 2.30(m, 2H), 2.58(m, 1H), 2.69(m, 2H), 3.73(m, 1H), 3.92(d, 1H), 4.59(d, 1H), 5.26(d, 1H), 7.15(dd, 1H), 7.20(d, 1H), 7.40(d, 1H), 7.47(s, 1H), 7.70(s, 2H), 8.48(d, 1H). LRMS: m/z (TSP$^+$) 489.1, 491.2 [MH$^+$] |
| 65[d] | 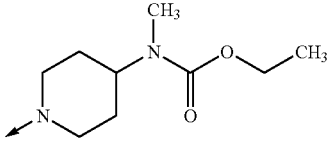 | 48 white foam | $^1$Hnmr(CDCl$_3$, 400MHz) δ: 1.20(t, 3H), 1.52(s, 4H), 1.88(m, 4H), 1.98(m, 1H), 2.10(m, 2H), 2.26(m, 2H), 2.54(m, 1H), 2.69(s, 3H), 2.76(m, 2H), 3.76(bs, 1H), 3.90(d, 1H), 4.08(q, 2H), 4.60(d, 1H), 7.09(dd, 1H), 7.18(d, 1H), 7.36(d, 1H), 7.44(s, 1H), 7.67(s, 2H), 8.45(dd, 1H). Microanalysis found: C, 60.08; H, 6.48; N, 10.21. C$_{27}$H$_{34}$Cl$_2$N$_4$O$_3$; 0.1CH$_2$Cl$_2$ requires C, 60.06; H, 6.36; N, 10.34%. |
| 66[e] | 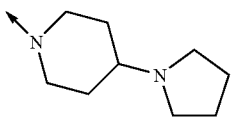 | 48 white solid | $^1$Hnmr(CDCl$_3$, 400MHz) δ: 1.46(m, 2H), 1.64(m, 2H), 1.77(m, 7H), 1.97(m, 4H), 2.13(m, 2H), 2.30(m, 2H), 2.54(m, 4H), 2.76(dd, 2H), 3.92(d, 1H), 4.56(d, 1H), 7.13(dd, 1H), 7.26(d, 1H), 7.39(d, 1H), 7.48(s, 1H), 7.68(m, 2H), 8.48(d, 1H). LRMS: m/z (ES$^+$) 501, 503 [MH$^+$] |
| 67[f] | 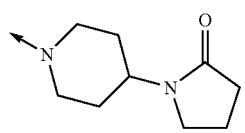 | 42 white foam | $^1$Hnmr(CDCl$_3$, 400MHz) δ: 1.57(m, 3H), 1.90–1.98(m, 8H), 2.13(m, 2H), 2.31(m, 2H), 2.37(m, 2H), 2.58(m, 1H), 2.79(m, 2H), 3.30(t, 2H), 3.90(m, 1H), 3.93(d, 1H), 4.60(d, 1H), 7.13(m, 1H), 7.23(d, 1H), 7.40(d, 1H), 7.47(s, 1H), 7.70(s, 2H), 8.48(d, 1H). LRMS: m/z (ES$^+$) 515, 517 [MH$^+$] |

| | R | Yield (%) | Data |
|---|---|---|---|
| 68[g] | ![structure] | 51 white foam | [1]Hnmr(CDCl[3], 400MHz) δ: 1.50(m, 2H), 1.80–2.00(m, 5H), 2.10(m, 2H), 2.20–2.40(m, 4H), 2.56(m, 1H), 2.80(m, 2H), 3.80(m, 1H), 3.86(s, 2H), 3.90(d, 1H), 4.60(d, 1H), 5.15(s, 1H), 7.10(m, 1H), 7.20(d, 1H), 7.36(d, 1H), 7.45(s, 1H), 7.67(d, 2H), 8.46(d, 1H). LRMS: m/z (ES+) 530, 532 [MH+] |
| 69[h] | ![structure] | 63 white foam | [1]Hnmr(CDCl[3], 400MHz) δ: 1.63(t, 4H), 1.88(m, 2H), 2.00(m, 1H), 2.11(m, 2H), 2.22–2.40(m, 6H), 2.53(m, 1H), 3.88(m, 5H), 4.62(d, 1H), 7.09(dd, 1H), 7.18(d, 1H), 7.37(d, 1H), 7.43(s, 1H), 7.65(s, 2H), 8.43(d, 1H). LRMS: m/z (TSP+) 490.2, 492.2 [MH+] |
| 70[i] | ![structure] | 30 white solid | [1]Hnmr(CDCl[3], 400MHz) δ: 1.61(m, 2H), 1.66(m, 2H), 1.96(m, 5H), 2.12(m, 2H), 2.27(m, 2H), 2.57(m, 1H), 2.88(m, 3H), 3.75(s, 3H), 3.94(d, 1H), 4.64(d, 1H), 6.80(d, 1H), 6.91(m, 1H), 7.10(m, 3H), 7.23(m, 1H), 7.38(d, 1H), 7.47(s, 1H), 7.68(d, 2H), 8.47(m, 1H). LRMS: m/z (ES+) 538, 540 [MH+] Microanalysis found: C, 66.09; H, 6.20; N, 7.67. $C_{30}H_{33}Cl_2N_3O_2$; 0.1CH[2]Cl[2] requires C, 66.09; H, 6.12; N, 7.68%. |
| 71[j] | ![structure] | 84 white solid | [1]Hnmr(CDCl[3], 400MHz) δ: 1.62(m, 4H), 1.97(m, 4H), 2.15(m, 2H), 2.29(m, 3H), 2.56(dd, 1H), 2.73(bs, 1H), 3.07(m, 2H), 3.94(d, 1H), 4.63(d, 1H), 7.12(m, 3H), 7.23(d, 1H), 7.41(d, 1H), 7.48(s, 1H), 7.59(dd, 1H), 7.69(m, 2H), 8.45(m, 2H). LRMS: m/z (ES+) 509, 511 [MH+] |
| 72[k] | ![structure] | 97 white foam | [1]Hnmr(CDCl[3], 400MHz) δ: 1.95(m, 2H), 2.04(m, 1H), 2.15(m, 2H), 2.28(m, 2H), 2.38(m, 4H), 2.58(m, 1H), 3.44(m, 4H), 3.92(d, 1H), 4.63(d, 1H), 6.58(d, 2H), 7.09(m, 1H), 7.20(d, 1H), 7.38(d, 1H), 7.42(m, 1H), 7.46(s, 1H), 7.66(s, 2H), 8.12(d, 1H), 8.43(d, 1H). LRMS: m/z (ES+) 510, 512 [MH+] |

Starting amines:

[a] = 4-(2-methoxyethoxy)piperidine hydrochloride as prepared in U.S. Pat. No. 4237138

[b] = 4-piperidinyl methylcarbamate from preparation 62

[c] = N-(4-piperidinyl)acetamide as prepared in EP 908452

[d] = Ethyl methyl(4-piperidinyl)carbamate as prepared in FR 2321890

[e] = 4-(1-pyrrolidinyl)piperidine

[f] = 1-(4-piperidinyl)-2-pyrrolidinone as prepared in WO 9410146

[g] = 3-(4-piperidinyl)-2,4-imidazolidinedione from preparation 67

[h] = 1,4-dioxa-8-azaspiro[4.5]decane

[i] = 4-(2-methoxyphenyl)piperidine

[j] = 2-(4'-piperidinyl)pyridine as prepared in EP 630887

[k] = 1 (2-pyridinyl)piperazine

EXAMPLE 73

(5S)-5-(3,4-Dichlorophenyl)-5-{2-[3-(4-hydroxy-1-piperidinyl)-1-azetidinyl]ethyl}-1-(2-pyridinyl)-2-piperidinone

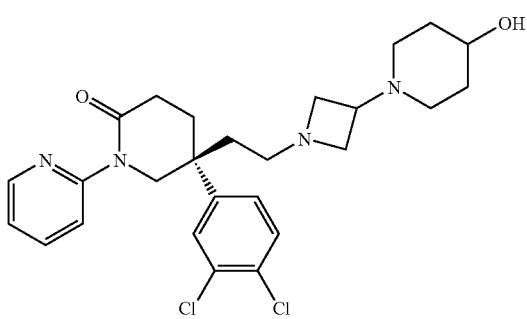

Triethylamine (1 ml, 7.2 mmol) and acetic acid (1.1 ml, 18.3 mmol) were added to a solution of 1-(3-azetidinyl)-4-piperidinol trifluoroacetate (WO 9605193) (250 mg, 0.93 mmol), the aldehyde from preparation 11a (250 mg, 0.62 mmol) and sodium triacetoxyborohydride (250 mg, 1.2 mmol) in dichloromethane (100 ml) and the reaction stirred at room temperature for 90 minutes. The solution was washed with water, dried (MgSO$_4$), and concentrated under reduced pressure. The residual gum was purified by column chromatography on silica gel using an elution gradient of dichloromethane:methanol (100:0 to 95:5) to afford the title compound as a yellow solid, 82 mg.

$^1$Hnmr (CDCl$_3$, 400 MHz) δ:1.55–2.40 (m, 14H), 2.60 (m, 3H), 2.80 (m, 2H), 2.95 (m, 1H), 3.52 (m, 2H), 3.75 (m, 1H), 3.95 (d, 1H), 4.58 (d, 1H), 7.20 (m, 2H), 7.40 (dd, 2H), 7.74 (m, 2H), 8.50 (d, 1H).

LRMS: m/z (TSP$^+$) 503.1, 505.1 [MH$^+$]

EXAMPLES 74 TO 85

The following examples of general structure:

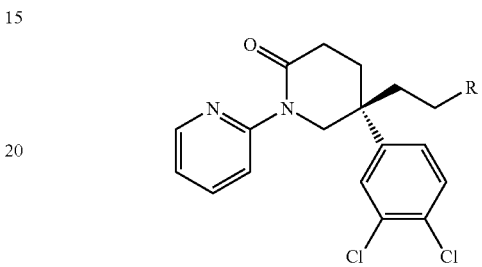

were prepared from the aldehyde from preparation 11a and the appropriate amines, following a similar procdure to that described in example 73.

| Example | R | Yield (%) | Data |
|---|---|---|---|
| 74[a] | ![structure: 4-hydroxy-4-methylpiperidinyl-azetidinyl] | 43 white solid | $^1$Hnmr (CDCl$_3$, 400MHz) δ: 1.25(s, 3H), 1.50–2.00(m, 8H), 2.18(m, 4H), 2.34(m, 4H), 2.60(m, 1H), 2.75(m, 2H), 2.95(m, 1H), 3.44(t, 2H), 3.90(d, 1H), 4.48(d, 1H), 6.55(d, 1H), 7.20(m, 2H), 7.42(d, 1H), 7.45(d, 1H), 7.72(d, 1H), 8.50(d, 1H). LRMS: m/z (TSP$^+$) 517.9, 519.9 [MH$^+$] Microanalysis found: C, 60.41; H, 6.75; N, 10.20. C$_{27}$H$_{34}$Cl$_2$N$_4$O$_2$;0.2CH$_2$Cl$_2$; 0.4H$_2$O requires C, 60.31; H, 6.55; N, 10.34%. |
| 75[b] | ![structure: morpholinyl-azetidinyl] | 60 white solid | $^1$Hnmr(CDCl$_3$, 400MHz) δ: 1.70(m, 1H), 1.82(m, 1H), 2.14(m, 2H), 2.30(m, 7H), 2.58(m, 1H), 2.72(m, 2H), 2.90(m, 1H), 3.40(t, 2H), 3.68(m, 4H), 3.90(d, 1H), 4.56(d, 1H), 7.16(dd, 1H), 7.20(dd, 1H), 7.40(d, 1H), 7.44(s, 1H), 7.70(m, 2H), 8.50(d, 1H). LRMS: m/z (TSP$^+$) 489.1, 491.1 [MH$^+$] |
| 76[1c] | ![structure: 3-hydroxy-3-phenylazetidinyl] | 78 white foam | $^1$Hnmr(CDCl$_3$, 400MHz) δ: 1.78(m, 1H), 1.86(m, 1H), 2.10–2.40(m, 5H), 2.57(m, 1H), 3.25(t, 2H), 3.50(t, 2H), 3.95(d, 1H), 4.63(d, 1H), 7.15(m, 1H), 7.25(m, 2H), 7.35(m, 2H), 7.40(m, 1H), 7.45(m, 3H), 7.70(d, 2H), 8.48(d, 1H). |

-continued

| Example | R | Yield (%) | Data |
|---|---|---|---|
| 77[1d] | [3-hydroxy-3-(2-methoxyphenyl)azetidin-1-yl] | 32 white foam | $^1$Hnmr(CDCl$_3$, 400MHz) δ: 1.80(m, 1H), 1.92(m, 1H), 2.08–2.45(m, 5H), 2.59(m, 1H), 3.42(m, 2H), 3.56(m, 2H), 3.84(s, 3H), 3.90(d, 1H), 4.58(d, 1H), 6.88(d, 1H), 6.95(dd, 1H), 7.14(m, 1H), 7.20(d, 2H), 7.24(m, 2H), 7.39(d, 1H), 7.44(s, 1H), 7.70(m, 2H), 8.45(d, 1H). LRMS: m/z (TSP$^+$) 526.1, 528.1 [MH$^+$] |
| 78[1e] | [3-(4-methanesulfonylpiperazin-1-yl)azetidin-1-yl] | 29 white foam | $^1$Hnmr(CDCl$_3$, 400MHz) δ: 1.70(m, 1H), 1.81(m, 1H), 2.10(m, 2H), 2.27(m, 4H), 2.38(m, 4H), 2.58(m, 1H), 2.70(m, 3H), 2.77(s, 3H), 2.96(m, 1H), 3.21(m, 2H), 3.38(m, 2H), 3.90(d, 1H), 4.57(d, 1H), 7.16(dd, 1H), 7.19(d, 1H), 7.41(d, 1H), 7.42(s, 1H), 7.70(m, 2H), 8.49(d, 1H). LRMS: m/z (TSP$^+$) 566.3 [MH$^+$] |
| 79[f] | [(3R)-3-hydroxypyrrolidin-1-yl] | 25 white solid | $^1$Hnmr(CDCl$_3$, 400MHz) δ: 1.80(m, 1H), 2.0–2.65(m, 12H), 2.80(m, 1H), 3.04(m, 1H), 3.96(d, 1H), 4.36(s, 1H), 4.72(d, 1H), 7.16(dd, 1H), 7.24(d, 1H), 7.44(d, 1H), 7.50(s, 1H), 7.75(m, 2H), 8.48(d, 1H). LRMS: m/z (TSP$^+$) 434.1, 436.1 [MH$^+$] Microanalysis found: C, 57.10; H, 5.73; N, 8.64. C$_{22}$H$_{25}$Cl$_2$N$_3$O$_2$; 0.4CH$_2$Cl$_2$;0.25H$_2$O requires C, 56.90; H, 5.61; N, 8.89%. |
| 80[g] | [4-hydroxy-4-(trifluoromethyl)piperidin-1-yl] | 8 | $^1$Hnmr(CDCl$_3$, 400MHz) δ: 1.62(d, 2H), 1.93(m, 5H), 2.18(m, 5H), 2.30(m, 2H), 2.62(m, 3H), 3.94(d, 1H), 4.74(d, 1H), 7.16(m, 1H), 7.22(d, 1H), 7.41(d, 1H), 7.48(s, 1H), 7.72(s, 2H), 8.48(d, 1H). LRMS: m/z (ES$^+$) 516, 518 [MH$^+$] Microanalysis found: C, 55.52; H, 5.13; N, 7.88. C$_{24}$H$_{26}$Cl$_2$F$_3$N$_3$O$_2$ requires C, 55.45; H, 5.11; N, 7.92%. |
| 81[h] | [4-(4-hydroxypiperidin-1-yl)piperidin-1-yl] | 18 white solid | $^1$Hnmr(CDCl$_3$, 400MHz) δ: 1.50–2.70(m, 24H), 2.88(m, 4H), 3.75(m, 1H), 3.91(d, 1H), 4.64(d, 1H), 7.16(m, 1H), 7.24(dd, 1H), 7.42(d, 1H), 7.50(s, 1H), 7.72 (s, 2H), 8.50 (d, 1H). LRMS: m/z (TSP$^+$) 531.2, 533.2 [MH$^+$] |
| 82[i] | [4-(pyridin-2-yl N-oxide)piperidin-1-yl] | 53 white foam | $^1$Hnmr(CDCl$_3$, 400MHz) δ: 1.26(m, 2H), 1.44(m, 2H), 1.85–2.08(m, 5H), 2.15(m, 2H), 2.26(m, 2H), 2.58(m, 1H), 2.85(m, 2H), 3.41(m, 1H), 3.95(d, 1H), 4.61(d, 1H), 7.08(m, 2H), 7.18(m, 3H), 7.38(d, 1H), 7.46(s, 1H), 7.64(m, 2H), 8.19(d, 1H), 8.42(d, 1H). LRMS: m/z (TSP$^+$) 525.1, 527.2 [MH$^+$] |

-continued

| Example | R | Yield (%) | Data |
|---|---|---|---|
| 83[1j] | [piperidine attached to pyridine N-oxide at 3-position] | 16 white solid | ¹Hnmr(CDCl₃, 400MHz) δ: 1.58(m, 2H), 1.75(m, 2H), 1.81–2.08(m, 5H), 2.15(m, 2H), 2.24–2.40(m, 3H), 2.58(m, 1H), 2.84(m, 2H), 3.90(d, 1H), 4.60(d, 1H), 7.02–7.20(m, 4H), 7.38(d, 1H), 7.45(m, 1H), 7.68(m, 2H), 8.02(m, 2H), 8.45(m, 1H). |
| 84[1k] | [piperidine attached to pyridine N-oxide at 4-position] | 33 white crystal | ¹Hnmr(CDCl₃, 400MHz) δ: 1.58(m, 2H), 1.72(m, 2H), 1.83–2.08(m, 5H), 2.16(m, 2H), 2.28(m, 2H), 2.40(m, 1H), 2.55(m, 1H), 2.85(m, 2H), 3.90(d, 1H), 4.60(d, 1H), 7.02(d, 2H), 7.10(m, 1H), 7.20(m, 1H), 7.38(d, 1H), 7.42(m, 1H), 7.66(m, 2H), 8.08(d, 2H), 8.42(m, 1H). LRMS: m/z (TSP⁺) 525.3, 527.3 [MH⁺] |
| 85[1l] | [piperazine attached to pyridine with CONH₂] | 37 white foam | ¹Hnmr(CDCl₃, 300MHz) δ: 1.94(m, 2H), 2.04(m, 1H), 2.14(m, 2H), 2.30(m, 2H), 2.42(m, 4H), 2.58(m, 1H), 3.17(m, 4H), 2.90(d, 1H), 4.69(d, 1H), 5.62(s, 1H), 7.12(m, 1H), 7.10(m, 1H), 7.20(m, 1H), 7.39(d, 1H), 7.45(s, 1H), 7.68(m, 2H), 8.24(d, 1H), 8.34(m, 2H), 8.45(d, 1H). LRMS: m/z (TSP⁺) 553.2, 555.2 [MH⁺] Microanalysis found: C, 59.34; H, 5.58; N,14.52. C₂₈H₃₀Cl₂N₆O₂; 0.73H₂O requires C, 59.35; H, 5.60; N, 14.83%. |
| 86[m] | [N-acetylhomopiperazine] | 30 white solid | ¹Hnmr(CDCl₃, 400MHz) δ: 1.73–1.98(m, 6H), 2.04(2xs, 3H), 2.17(m, 2H), 2.28(m, 2H), 2.38–2.62(m, 4H), 3.38–3.58(m, 4H), 3.92(d, 1H), 4.66(m, 1H), 7.17(m, 1H), 7.22(m, 1H), 7.41(m, 1H), 7.46(s, 1H), 7.72(m, 2H), 8.46(d, 1H). LRMS: m/z (TSP⁺) 489.1, 491.1 [MH⁺] |

[1]= the aldehyde hydrochloride from preparation 11b was used

[2]= no triethylamine was used in the reaction

Starting amines:

[a]= 1-(3-azetidinyl)-4-methyl-4-piperidinol trifluoroacetate from preparation 28

[b]= 3-morpholinoazetidine dihydrochloride as prepared in WO 9725322

[c]= 3-hydroxy-3-phenylazetidine hydrochloride as prepared in J.A.C.S; 1972; 94(8); 2758

[d]= 3-hydroxy-3-(2-methoxyphenyl)azetidine hydrochloride from preparation 30

[e]= 1-(3-azetidinyl)-4-(methylsulphonyl)piperazine trifluoroacetate as prepared in WO 9725322

[f]= (S)-3-pyrrolidinol

[g]= 4-trifluoromethylpiperidinol trifluoroacetate from preparation 58

[h]= 1-(piperidin-4-yl)-4-piperidinol from preparation 64

[i]= 2-(4-piperidinyl)pyridine 1-oxide as prepared in WO 0037026

[j]= 3-(4-piperidinyl)pyridine 1-oxide dihydrochloride as prepared in preparation 74

[k]= 4-(4-piperidinyl)pyridine 1-oxide dihydrochloride as prepared in preparation 73

[l]= 2-(1-piperazinyl)nicotinamide hydrochloride as prepared in J. Med. Chem. 1983; 26(12); 1696

[m]= N-acetylhomopiperazine

EXAMPLE 87

(5S)-5-(3,4-Dichlorophenyl)-5-{2-[4-hydroxy-4-(trifluoromethyl)-1-piperidinyl]ethyl}-1-(6-methyl-2-pyridinyl)-2-piperidinone

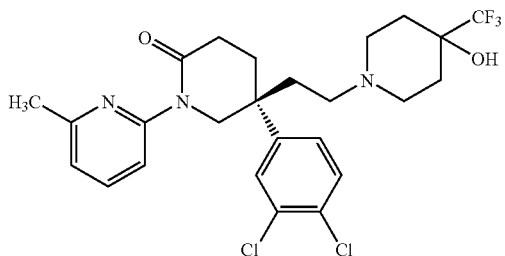

The title compound was obtained as a solid, from the aldehyde from preparation 12a, and the amine from preparation 58, following a similar procedure to that described in example 73.

¹Hnmr (CDCl₃, 400 MHz) δ: 1.62 (m, 4H), 1.82 (m, 2H), 1.94 (t, 2H), 2.02–2.18 (m, 5H), 2.30 (m, 2H), 2.50 (s, 3H), 2.58 (d, 1H), 2.68 (d, 1H), 3.90 (d, 1H), 4.42 (d, 1H), 6.98 (d, 1H), 7.22 (d, 1H), 7.41 (d, 2H), 7.58 (d, 2H).

LRMS: m/z (TSP⁺) 530.1, 532.1 [MH⁺]

Microanalysis found: C, 55.39; H, 5.48; N, 7.58. C₂₅H₂₈Cl₂F₃N₃O₂;0.2CH₂Cl₂ requires C, 55.29; H, 5.23; N, 7.68%.

EXAMPLE 88

N-(1-{2-[(3S)-3-(3,4-Dichlorophenyl)-6-oxo-1-(2-pyridinyl)piperidinyl]ethyl}-4-phenyl-4-piperidinyl)-N-methylacetamide

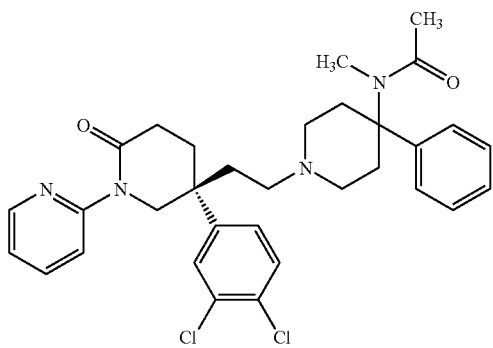

Triethylamine (2 ml) and glacial acetic acid (2 ml) were added to a solution of N-methyl-N-(4-phenyl-4-piperidinyl)acetamide (WO 9805640) (97.9 mg, 036 mmol) and the aldehyde hydrochloride from preparation 11b (145 mg, 0.36 mmol) in dichloromethane (20 ml). Sodium triacetoxyborohydride (79 mg, 0.37 mmol) was added and the reaction stirred at room temperature for 18 hours. The reaction was neutralised using saturated sodium bicarbonate solution, the phases separated and the organic layer washed with brine, dried (MgSO₄), and concentrated under reduced pressure. The crude product was purified by column chromatography on silica gel using dichloromethane:methanol:0.88 ammonia (95:5:0.5) as eluant, and azeotroped with diethyl ether to afford the title compound as a white foam, 92 mg.

¹Hnmr (CDCl₃, 400 MHz) δ: 1.86–2.21 (m, 15H), 2.21–2.37 (m, 2H), 2.60 (m, 3 2.81 (s, 2H), 3.93 (d, 1H), 4.68 (d, 1H), 7.13 (m, 1H), 7.20–7.38 (m, 6H), 7.40 (d, 1H), 7.49 (s, 1H), 7.71 (d, 2H), 8.48 (d, 1H).

LRMS: m/z (TSP⁺) 579.1, 581.1 [MH⁺]

Microanalysis found: C, 63.57; H, 6.72; N, 9.10. C₃₂H₃₆Cl₂N₄O₂; 1.3H₂O require C, 63.74; H, 6.45; N, 9.29%.

EXAMPLES 89 TO 94

The following examples of general structure:

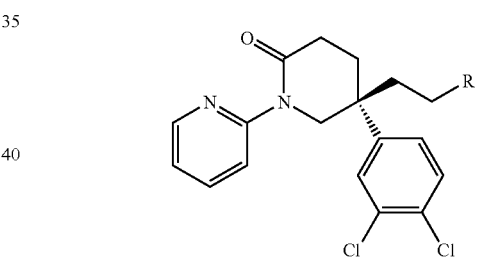

were prepared from the aldehyde hydrochloride from preparation 11b and the appropriate amine, following a similar procedure to that described in example 88.

| Example | R | Yield (%) | Data |
|---|---|---|---|
| 89ᵃ | ![morpholine-piperidine] | 62 white foam | ¹Hnmr(CDCl₃, 300MHz) δ: 1.43(m, 2H), 1.77(m, 4H), 1.97(m, 3H), 2.12(m, 3H), 2.34(m, 2H), 2.52(m, 4H), 2.60(m, 1H), 2.81(m, 2H), 3.71(m, 4H), 3.95(d, 1H), 4.63(d, 1H), 7.14(m, 1H), 7.21(d, 1H), 7.41(d, 1H), 7.50(s, 1H), 7.72(m, 2H), 8.51(d, 1H). Microanalysis found: C, 61.67; H, 6.70; N, 10.63. C₂₇H₃₄Cl₂N₄O₂; 0.5H₂O requires C, 61.59; H, 6.70; N, 10.64%. |

-continued

| Example | R | Yield (%) | Data |
|---|---|---|---|
| 90[1b] | [structure: piperidine with 4-phenyl and 4-NHC(O)CH₃ substituents] | 19 white foam | ¹Hnmr(CDCl₃, 400MHz) δ: 1.83–2.18(m, 12H), 2.21–2.36(m, 4H), 2.49–2.67(m, 3H), 3.91(d, 1H), 4.68(d, 1H), 5.40(bs, 1H), 7.10(m, 1H), 7.15–7.32(m, 6H), 7.39(d, 1H), 7.45(s, 1H), 7.66(m, 2H), 8.42(d, 1H). LRMS: m/z (TSP⁺) 565.2, 567.2 [MH⁺] Microanalysis found: C, 63.41; H, 6.25; N, 9.54. $C_{31}H_{34}Cl_2N_4O_2$; 1.2H₂O requires C, 63.24; H, 6.01; N, 9.27%. |
| 91[2c] | [structure: piperidine with 4-phenyl and 4-C(O)NH₂ substituents] | 62 white foam | ¹Hnmr(CDCl₃, 400MHz) δ: 1.59(m, 2H), 1.80–2.70(m, 14H), 3.92(d, 1H), 4.72(d, 1H), 5.20(bs, 2H), 7.15(m, 1H), 7.24(m, 3H), 7.33–7.46(m, 4H), 7.49(s, 1H), 7.70(m, 2H), 8.44(d, 1H). LRMS: m/z (TSP⁺) 551.1, 553.1 [MH⁺] Microanalysis found: C, 63.28; H, 6.04; N, 9.41. $C_{30}H_{32}Cl_2N_4O_2$; 1.1H₂O requires C, 63.07; H, 6.03; N, 9.81%. |
| 92[2d] | [structure: piperidine with 4-OH and 4-(2-pyridinyl) substituents] | 58 off-white foam | ¹Hnmr(CDCl₃, 300MHz) δ: 1.62(m, 2H), 1.90–2.50(m, 12H), 2.55–2.82(m, 3H), 4.40(d, 1H), 4.69(d, 1H), 7.05–7.29(m, 3H), 7.37(d, 1H), 7.42(d, 1H), 7.53(s, 1H), 7.71(m, 3H), 8.50(m, 2H). LRMS: m/z (TSP⁺) 525.1, 527.1 [MH⁺] Microanalysis found: C, 62.77; H, 5.97; N, 10.19. $C_{28}H_{30}Cl_2N_4O_3$; 0.5H₂O requires C, 62.92; H, 5.85; N, 10.18%. |
| 93[e] | [structure: piperazine with ethyl acetate group] | 14 | ¹Hnmr(CDCl₃, 300MHz) δ: 1.28(t, 3H), 1.84–2.46(m, 12H), 2.46–2.73(m, 4H), 3.19(s, 2H), 3.96(d, 1H), 4.19(q, 2H), 4.66(d, 1H), 7.16(m, 1H), 7.24(d, 1H), 7.42(d, 1H), 7.49(s, 1H), 7.71(m, 2H), 8.50(d, 1H). LRMS: m/z (TSP⁺) 519.2, 521.3 [MH⁺] |
| 94[f] | [structure: piperazine with 2-hydroxyethyl group] | 36 white foam | ¹Hnmr(CDCl₃, 300MHz) δ: 1.82–2.70(m, 18H), 3.59(t, 2H), 3.98(d, 1H), 4.66(d, 1H), 7.16(m, 1H), 7.22(d, 1H), 7.41(d, 1H), 7.51(s, 1H), 7.72(m, 2H), 8.50(d, 1H). Microanalysis found: C, 58.37; H, 6.40; N, 10.95. $C_{24}H_{30}Cl_2N_4O_2$; 0.9H₂O requires C, 58.39; H, 6.40; N, 11.35%. |

[1] = No triethylamine was added to the reaction mixture.

[2] = Tetrahydrofuran was used as the reaction solvent

Starting amines:

[a] = 4-(4-piperidinyl)morpholine hydrochloride from preparation 65

[b] = N-methyl-N-(4-phenyl-4-piperidinyl)acetamide as prepared in WO 9805640

[c] = 4-phenyl-4-piperidinecarboxamide as prepared in WO 9426735

[d] = 4-(2-pyridinyl)-4-piperidinol as prepared in DE 2630152

[e] = ethyl 1-piperazinylacetate

[f] = 2-(1-piperazinyl)ethanol

EXAMPLES 95 TO 96

The following examples of general structure:

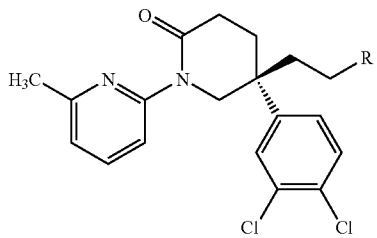

were prepared from the aldehyde hydrochloride from preparation 12b and the appropriate amine, following a similar procedure to that described in example 88, isolating the compounds after azeotroping with diethyl ether.

The title compound was obtained as a white foam in 74% yield, after trituration from diethyl ether, from the aldehyde from preparation 17 and 3-morpholinoazetidine dihydrochloride (WO 9725322), following a similar procedure to that described in example 88.

$^1$Hnmr (CDCl$_3$, 400 MHz) δ: 1.63 (m, 1H), 1.79 (m, 1H), 1.98–2.35 (m, 9H), 2.41–2.55 (m, 1H), 2.60–2.73 (m, 2H), 2.83 (t, 1H), 3.06 (s, 6H), 3.24 (q, 2H), 3.63 (s, 4H), 3.70 (d, 1H), 4.59 (d, 1H), 6.32 (d, 1H), 6.81 (d, 1H), 7.28 (d, 1H), 7.36 (d, 1H), 7.43 (dd, 1H), 7.57 (s, 1H).

LRMS: m/z (TSP$^+$) 532.2, 534.3 [MH$^+$]

Microanalysis found: C, 60.06; H, 6.69; N, 12.85. C$_{27}$H$_{35}$Cl$_2$N$_5$O$_2$; 0.35H$_2$O requires C, 60.19; H, 6.68; N, 13.00%.

| Example | R | Yield (%) | Data |
|---|---|---|---|
| 95$^a$ | ![piperazinyl-pyridinyl-methyl-methanesulfonamide] | 37 white foam | $^1$Hnmr (CDCl$_3$, 300MHz) δ: 1.98(m, 2H), 2.07–2.41(m, 5H), 2.41–2.66(m, 8H), 2.86(s, 3H), 3.10(t, 4H), 3.92(d, 1H), 4.32(d, 2H), 4.77(d, 1H), 5.69(m, 1H), 6.98–7.06(m, 2H), 7.29(d, 1H), 7.44(m, 2H), 7.57–7.66(m, 3H), 8.31(d, 1H). LRMS: m/z (TSP$^+$) 631.3, 633.3 [MH$^+$] Microanalysis found: C, 56.45; H, 6.05; N, 12.41. C$_{30}$H$_{36}$Cl$_2$N$_6$O$_3$S; 0.5(CH$_3$CH$_2$)$_2$O; 0.5 H$_2$O requires C, 56.71; H, 6.25; N, 12.40%. |
| 96$^b$ | ![piperazinyl-pyridyl-dimethylmethanamine] | 36 white foam | $^1$Hnmr (CDCl$_3$, 300MHz) δ: 1.98(m, 2H), 2.14–2.30(m, 10H), 2.30–2.41(m, 2H), 2.41–2.65(m, 7H), 3.26(m, 4H), 3.35(s, 2H), 3.92(d, 1H), 4.77(d, 1H), 6.91(dd, 1H), 7.01(d, 1H), 7.31(d, 1H), 7.42(d, 2H), 7.56–7.72(m, 3H), 8.20(d, 1H). LRMS: m/z (TSP$^+$) 581.1, 583.2 [MH$^+$] Microanalysis found: C, 63.22; H, 6.61; N, 13.72. C$_{31}$H$_{38}$Cl$_2$N$_6$O;0.1(CH$_3$CH$_2$)$_2$O; 0.5H$_2$O requires C, 63.07; H, 6.74; N, 14.05%. |

Starting amines;
$^a$= N-{[2-(1-piperazinyl)-3-pyridinyl]methyl}methanesulphonamide dihydrochloride as prepared in preparation 80
$^b$= N,N-dimethyl[2-(1-piperazinyl)-3-pyridyl]methanamine trihydrochloride as prepared in preparation 79

EXAMPLE 97

(5S)-5-(3,4-Dichlorophenyl)-1-[6-(dimethylamino)-2-pyridinyl]-5-{2-[3-(4-morpholinyl)-1-azetidinyl]ethyl}-2-piperidinone

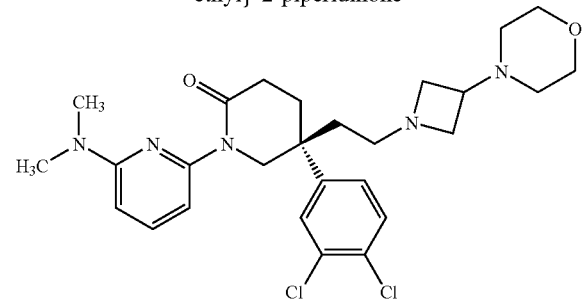

EXAMPLE 98

N-[1-(2-{(3S)-3-(3,4-Dichlorophenyl)-1-[6-(dimethylamino)-2-pyridinyl]-6-oxopiperidinyl}ethyl)-4-piperidinyl]-N-methylacetamide

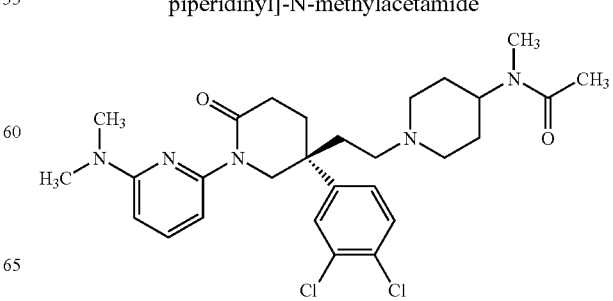

The title compound was obtained as a white foam in 67% yield, from the aldehyde from preparation 17 and the amine from preparation 60, following the procedure described in example 88.

1 Hnmr (CDCl$_3$, 400 MHz) δ: 1.42–1.60 (m, 3H), 1.69 (m, 1H), 1.77–2.29 (m, 12H), 2.55 (m, 1H), 2.72–2.82 (m, 5H), 3.10 (s, 6H), 4.39 (m, 1H), 4.63 (d, 1H), 6.37 (d, 2H), 6.84 (d, 1H), 7.29–7.42 (m, 2H), 7.48 (dd, 1H), 7.61 (s, 1H).

LRMS: m/z (TSP$^+$) 546.3, 548.3 [MH$^+$]

Microanalysis found: C, 60.20; H, 6.93; N, 12.40. C$_{28}$H$_{37}$Cl$_2$N$_5$O$_2$; 0.5H$_2$O requires C, 60.54; H, 6.89; N, 12.61%.

EXAMPLE 99 tert-Butyl 1-{2-[(3S)-3-(3,4-dichlorophenyl)-6-oxo-1-(2-pyridinyl)piperidinyl]ethyl}-4-piperidinyl(methyl)carbamate

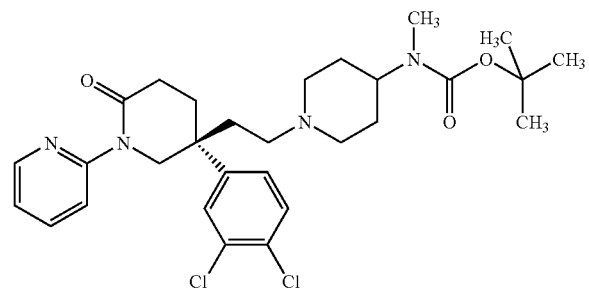

Triethylamine (1.5 ml, 10.8 mmol) was added to a suspension of the aldehyde hydrochloride from preparation 11b (500 mg, 1.25 mmol) and tert-butyl methyl(4-piperidinyl)carbamate (EP 457686) (402 mg, 1.88 mmol) in dichloromethane (250 ml), and the mixture stirred at room temperature for 5 minutes. Acetic acid (1.5 ml, 26.2 mmol) and sodium triacetoxyborohydride (530 mg, 2.5 mmol) were added and the reaction stirred at room temperature for 2 hours. The mixture was washed with 2N sodium hydroxide solution (200 ml), and the aqueous wash extracted with dichloromethane (2×200 ml). The combined organic solutions were washed with brine, dried (MgSO$_4$) and evaporated under reduced pressure. The crude product was purified by Biotage® column chromatography on silica gel using an elution gradient of dichloromethane:methanol (100:0 to 95:5) to afford the title compound as a white foam, 360 mg.

$^1$Hnmr (CDCl$_3$, 300 MHz) δ: 1.45 (s, 9H), 1.58 (m, 6H), 1.81–2.21 (m, 6H), 2.32 (m, 2H), 2.57–2.64 (m, 1H), 2.70 (s, 3H), 2.80 (m, 2H), 3.95 (d, 1H), 4.64 (d 1H), 7.16 (m, 1H), 7.23 (m, 1H), 7.41 (m, 1H), 7.50 (s, 1H), 7.72 (m, 2H), 8.50 (m, 1H).

LRMS: m/z (TSP$^+$) 561.2, 563.2 [MH$^+$]

Microanalysis found: C, 61.50; H, 6.87; N, 9.83. C$_{29}$H$_{38}$Cl$_2$N$_4$O$_3$ requires C, 62.03; H, 6.77; N, 9.98%.

EXAMPLES 100 TO 111

The following examples of general structure:

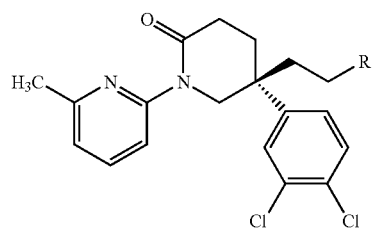

were prepared from the aldehyde hydrochloride from preparation 12b and the appropriate amine, following a similar procedure to that described in example 99, except the products were purified by column chromatography on silica gel using dichloromethane:methanol:0.88 ammonia as eluant.

| Example | R | Yield (%) | Data |
|---|---|---|---|
| 100[a] | ![piperazine-azetidine-SO2NH2] | 28 white solid | $^1$Hnmr (CDCl$_3$, 400MHz) δ: 1.75(m, 1H), 1.82(m, 1H), 2.06–2.18(m, 2H), 2.20–2.08(m, 2H), 2.14(m, 3H), 2.54(m, 3H), 2.79(m, 2H), 2.98(m, 1H), 3.03(m, 5H), 3.16(m, 2H), 3.44(m, 2H), 3.82(d, 1H), 4.46(d, 1H), 6.97(d, 1H), 7.19(d, 1H), 7.38(m, 2H), 7.55(m, 2H). LRMS: m/z (TSP$^+$) 502.8, 504.8 [MH$^+$] |
| 101[b] | ![piperidine-N(CH3)COCH3] | 27 white solid | $^1$Hnmr (CDCl$_3$, 400MHz) δ: 1.56(m, 3H), 1.70(m, 3H), 1.92(m, 4H), 2.03(s, 3H), 2.16(m, 2H), 2.30(m, 2H), 2.55(m, 4H), 2.80(s, 3H), 3.00(m, 1H), 3.42(m, 1H), 4.40(m, 1H), 4.58(dd, 1H), 7.00(d, 1H), 7.22(d, 1H), 7.40(m, 2H), 7.59(d, 2H). LRMS: m/z (TSP$^+$) 517.2, 519.2 [MH$^+$] |

-continued

| Example | R | Yield (%) | Data |
|---|---|---|---|
| 102c | [piperidine-N, 4-(pyridin-2-yl N-oxide)] | 61 white foam | ¹Hnmr (CDCl₃, 400MHz) δ: 1.46(m, 2H), 1.88–2.08(m, 8H), 2.15(m, 2H), 2.25(m, 2H), 2.54(s, 3H), 2.84(m, 2H), 3.42(m, 1H), 3.90(d, 1H), 4.60(d, 1H), 6.98(d, 1H), 7.06(m, 1H), 7.18(m, 3H), 7.39(d, 2H), 7.58(m, 2H), 8.20(d, 1H). LRMS: m/z (TSP⁺) 539.2, 541.1 [MH⁺] |
| 103d | [piperidine-N, 4-(pyridin-3-yl N-oxide)] | 33 | ¹Hnmr (CD₃OD, 400MHz) δ: 2.15(m, 4H), 2.50(m, 3H), 2.77(s, 3H), 2.80–3.00(m, 4H), 3.08(m, 2H), 3.17(m, 2H), 3.63(m, 2H), 4.20(d, 1H), 4.34(d, 1H), 7.42(d, 1H), 7.59(d, 1H), 7.68(m, 2H), 7.80(m, 1H), 7.92(m, 1H), 8.22(m, 1H), 8.42(m, 1H), 8.72(m, 1H), 8.91(s, 1H). |
| 104e | [piperidine-N, 4-(pyridin-4-yl N-oxide)] | 42 | ¹Hnmr (CD₃OD, 400MHz) δ: 2.15(m, 4H), 2.39(m, 2H), 2.50(m, 3H), 2.77(s, 3H), 2.80–3.00(m, 2H), 3.06(m, 2H), 3.19(m, 2H), 3.63(m, 2H), 4.21(d, 1H), 4.34(d, 1H), 7.42(d, 1H), 7.59(d, 1H), 7.68(m, 2H), 7.80(m, 1H), 7.95(m, 2H), 8.44(m, 1H), 8.80(m, 2H). LRMS: m/z (TSP⁺) 539.3 [MH⁺] |
| 105f | [4-hydroxy-4-(pyridin-2-yl)piperidine] | 23 pale yellow solid | ¹Hnmr (CDCl₃, 400MHz) δ: 1.60(d, 1H), 1.75–2.10(m, 7H), 2.18(m, 2H), 2.32(m, 2H), 2.44(m, 2H), 2.56(s, 3H), 2.60(m, 1H), 2.75(m, 2H), 3.94(d, 1H), 4.60(d, 1H), 7.00(d, 1H), 7.20(m, 2H), 7.36(d, 1H), 7.40(dd, 2H), 7.60(m, 2H), 7.71(dd, 1H), 8.50(d, 1H). LRMS: m/z (ES⁺) 539, 541 [MH⁺] Microanalysis found: C, 63.12; H, 5.94; N, 9.94. C₂₉H₃₂Cl₂N₄O₂; 0.2CH₂Cl₂ requires C, 63.02; H, 6.12; N, 9.92%. |
| 106g | [4-hydroxy-4-(4-chlorophenyl)piperidine] | 38 white foam | ¹Hnmr (CDCl₃, 300MHz) δ: 1.65(m, 3H), 1.91–2.40(m, 11H), 2.55(s, 3H), 2.63(m, 2H), 3.96(d, 1H), 4.64(d, 1H), 7.01(d, 1H), 7.28(m, 3H), 7.40(m, 4H), 7.60(m, 2H). LRMS: m/z (TSP⁺) 573.0, 575.1 [MH⁺] |
| 107h | [4-(hydroxymethyl)-4-phenylpiperidine] | 42 white foam | ¹Hnmr (CDCl₃, 300MHz) δ: 1.80–2.37(m, 14H), 2.57(m, 6H), 3.54(m, 2H), 3.92(d, 1H), 4.63(d, 1H), 7.00(m, 1H), 7.19–7.43(m, 8H), 7.60(m, 2H). LRMS: m/z (ES⁺) 552, 554 [MH⁺] |

-continued

| Example | R | Yield (%) | Data |
|---|---|---|---|
| 108[i] | [pyridine N-oxide-2-yl piperazine structure] | 10 white foam | ¹Hnmr (CDCl₃, 400MHz) δ: 1.94(m, 2H), 2.04–2.20(m, 4H), 2.24(m, 2H), 2.50(m, 7H), 3.30(m, 4H), 3.90(d, 1H), 4.64(d, 1H), 6.78(d, 1H), 6.80(dd, 1H), 6.97(d, 1H), 7.17(m, 1H), 7.21(m, 1H), 7.40(m, 2H), 7.58(m, 2H), 8.12(d, 1H). Microanalysis found: C, 60.14; H, 5.99; N, 12.28. $C_{28}H_{31}Cl_2N_5O_2$; $H_2O$ requires C, 60.22; H, 5.96; N, 12.54%. |
| 109[j] | [3-methoxy-2-pyridinyl piperazine structure] | 72 white foam | ¹Hnmr (CDCl₃, 300MHz) δ: 1.93–2.63(m, 15H), 3.39(m, 4H), 3.86(s, 3H), 3.92(d, 1H), 4.74(d, 1H), 6.83(m, 1H), 7.03(dd, 2H), 7.28(m, 1H), .7.43(d, 2H), 7.61(m, 2H), 7.88(d, 1H). LRMS: m/z (ES⁺) 554, 556 [MH⁺] Microanalysis found: C, 61.92; H, 5.95; N, 11.86. $C_{29}H_{33}Cl_2N_5O_2$; $0.5H_2O$ requires C, 61.81; H, 6.08; N, 12.43%. |
| 110[k] | [nicotinamide piperazine structure] | 76 white foam | ¹Hnmr (CDCl₃, 300MHz) δ: 1.97(m, 2H), 2.07–2.62(m, 13H), 3.23(m, 4H), 3.92(d, 1H), 4.78(d, 1H), 5.80(s, 1H), 7.03(m, 1H), 7.09(m, 1H), 7.28(m, 1H), 7.44(m, 2H), 7.62(m, 2H), 8.30(m, 1H), 8.40(m, 2H). LRMS: m/z (TSP⁺) 568.0, 570.1 [MH⁺] Microanalysis found: C, 60.02; H, 5.85; N, 14.25. $C_{29}H_{32}N_6Cl_2O_2$; $0.2CH_2Cl_2$ requires C, 60.00; H, 5.59; N, 14.38%. |
| 111[l] | [nicotinonitrile piperazine structure] | 71 white foam | ¹Hnmr (CDCl₃, 300MHz) δ: 1.96(m, 2H), 2.04–2.59(m, 13H), 3.68(m, 4H), 3.92(d, 1H), 4.74(d, 1H), 6.75(m, 1H), 7.00(d, 1H), 7.27(m, 1H), 7.43(m, 2H), 7.61(m, 2H), 7.75(d, 1H), 8.32(s, 1H). LRMS: m/z (TSP⁺) 550.0, 552.0 [MH⁺] Microanalysis found: C, 62.70; H, 5.55; N, 14.79. $C_{29}H_{30}N_6Cl_2O$; $0.1CH_2Cl_2$ requires C, 62.64; H, 5.46; N, 15.06%. |

¹ = isolated as the hydrochloride salt

Starting amines:

[a] = 4-(3-azetidinyl)-1-piperazine sulphonamide trifluoroacetate as prepared in WO 9725322

[b] = N-methyl-N-(4-piperidinyl)acetamide hydrochloride from preparation 60

[c] = 2-(4-piperidinyl)pyridine 1-oxide as prepared in WO 0037026

[d] = 3-(4-piperidinyl)pyridine 1-oxide dihydrochloride as prepared in preparation 73

[e] = 4-(4-piperidinyl)pyridine 1-oxide dihydrochloride as prepared in preparation 72

[f] = 4-(2-pyridinyl)-4-piperidinol as prepared in DE 2630152

[g] = 4-(4-chlorophenyl)-4-piperidinol

[h] = (4-phenyl-4-piperidinyl)methanol

[i] = 1-(1-oxido-2-pyridinyl)piperazine dihydrochloride as prepared in preparation 74

[j] = 1-(3-methoxy-2-pyridinyl)piperazine as prepared in EP 345808

[k] = 2-(1-piperazinyl)nicotinamide as prepared in J. Med. Chem. 1983; 26(12); 1696.

[l] = 2-(1-piperazinyl)nicotinonitrile

EXAMPLE 112

(5S)-5-(3,4-Dichlorophenyl)-5-(2-{[(1-oxido-2-pyridinyl)methyl]amino}ethyl)-1-(2-pyridinyl)-2-piperidinone

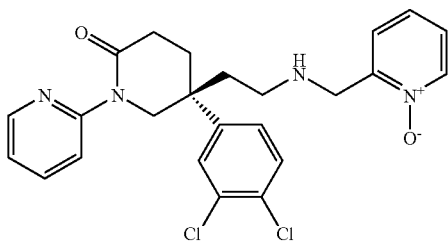

Triethylamine (287 μl, 2.06 mmol) was added to a suspension of the aldehyde from preparation 11a (250 mg, 0.68 mmol) in dichloromethane (10 ml) followed by (1-oxido-2-pyridinyl)methylamine (J.O.C. 1974; 39(9); 1250) (136 mg, 0.68 mmol) and the mixture stirred at room temperature for 15 minutes. Acetic acid (158 μl, 2.75 mmol) and sodium triacetoxyborohydride (292 mg, 1.38 mmol) were added and the reaction stirred at room temperature for 18 hours. The mixture was washed with 2N sodium hydroxide solution (5 ml), dried (MgSO$_4$) and concentrated under reduced pressure. The crude product was purified by column chromatography on silica gel using an elution gradient of dichloromethane:methanol:0.88 ammonia (95:5:0.5 to 93:7:1) to afford the title compound as a white foam, 224 mg.

$^1$Hnmr (CDCl$_3$, 400 MHz) δ: 1.90 (m, 1H), 2.00 (m, 1H), 2.15 (m, 1H), 2.28 (m, 3H), 2.47 (m, 1H), 2.58 (m, 1H), 3.85 (s, 2H), 3.90 (d, 1H), 4.58 (d, 1H), 7.15 (dd, 1H), 7.19 (m, 4H), 7.39 (d, 1H), 7.47 (s, 1H), 7.70 (q, 2H), 8.19 (d, 1H), 8.47 (d, 1H).

LRMS: m/z (TSP$^+$) 471.1, 473.1 [MH$^+$]

Microanalysis found: C, 58.74; H, 5.14; N, 11.28. C$_{24}$H$_{24}$Cl$_2$N$_4$O$_2$; 0.3CH$_2$Cl$_2$ requires C, 58.74; H, 4.99; N, 11.28%.

EXAMPLES 113 TO 118

The following examples of general structure:

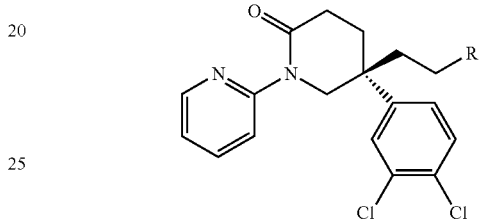

were prepared from the aldehyde from preparation 11b and the appropriate amines, following a similar procedure to that described in example 112.

| Example | R | Yield (%) | Data |
|---|---|---|---|
| 113$^a$ | ![CH3-N-CH2CH2-O-CH3] | 43 clear oil | $^1$Hnmr (CDCl$_3$, 400MHz) δ: 1.82–2.32(m, 10H), 2.39(m, 2H), 2.56(m, 1H), 3.22(s, 3H), 3.30(m, 2H), 3.88(d, 1H), 4.52(d, 1H), 7.10(m, 1H), 7.19(d, 1H), 7.38(d, 1H), 7.43(s, 1H), 7.66(s, 2H), 8.43(d, 1H). LRMS: m/z (TSP$^+$) 436.1, 438.1 [MH$^+$] Microanalysis found: C, 60.17; H, 6.24; N, 9.48. C$_{22}$H$_{27}$Cl$_2$N$_3$O$_2$ requires C, 60.55; H, 6.24; N, 9.63%. |
| 114$^b$ | ![HN-C(=O)CH3 with piperidine-phenyl-azetidine] | 42 white foam | $^1$Hnmr (CDCl$_3$, 400MHz) δ: 1.62(m, 2H), 1.72(m, 1H), 1.84(m, 1H), 2.00(s, 3H), 2.10(m, 6H), 2.30(m, 4H), 2.55–2.75(m, 4H), 2.91(t, 1H), 3.41(t, 2H), 3.88(d, 1H), 4.54(d, 1H), 5.45(s, 1H), 7.17(m, 1H), 7.21(m, 2H), 7.30(m, 2H), 7.37(m, 2H), 7.40(d, 1H), 7.45(s, 1H), 7.70(s, 2H), 8.50(d, 1H). LRMS: m/z (TSP$^+$) 620.3, 622.3 [MH$^+$] |

-continued

| Example | R | Yield (%) | Data |
|---|---|---|---|
| 115[c] | 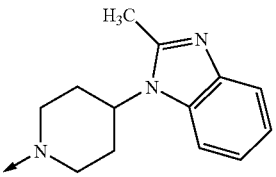 | 48 white foam | ¹Hnmr (CDCl₃, 400MHz) δ: 1.80(d, 2H), 2.00(m, 4H), 2.13(q, 2H), 2.21(m, 2H), 2.33(dd, 2H), 2.46(m, 2H), 2.60(s, 3H), 2.93(d, 1H), 3.01(d, 1H), 4.00(d, 1H), 4.09(m, 1H), 4.75(d, 1H), 7.18(m, 3H), 7.28(d, 1H), 7.45(d, 1H), 7.46(d, 1H), 7.53(s, 1H), 7.68(d, 1H), 7.75(d, 2H), 8.50(d, 1H) LRMS: m/z (TSP⁺) 562.1, 564.1 [MH⁺] Microanalysis found: C, 62.70; H, 5.64; N,11.92. $C_{31}H_{33}Cl_2N_5O$; 0.18CH₂Cl₂ requires C, 62.88; H, 5.69; N, 11.66%. |
| 116[d] | 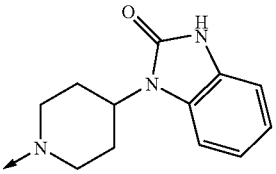 | 79 white foam | ¹Hnmr (CDCl₃, 400MHz) δ: 1.78(d, 2H), 2.00(m, 4H), 2.07(m, 1H), 2.19(q, 2H), 2.32(m, 4H), 2.61(m, 1H), 2.90(m, 2H), 3.99(d, 1H), 4.30(m, 1H), 4.70(d, 1H), 7.05(s, 3H), 7.18(m, 2H), 7.43(d, 1H), 7.50(s, 1H), 7.72(s, 2H), 8.50(d, 1H), 8.62(s, 1H). LRMS: m/z (TSP⁺) 564.1, 566.1 [MH⁺] Microanalysis found: C, 59.45; H, 5.34; N, 11.39. $C_{30}H_{31}Cl_2N_5O_2$;0.6CH₂Cl₂ requires C, 59.72; H, 5.27; N, 11.38%. |
| 117[e] | 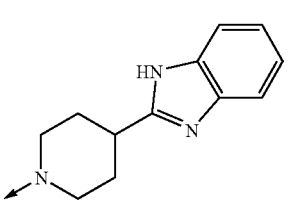 | 16 white foam | ¹Hnmr (CDCl₃, 400MHz) δ: 1.73–1.85(m, 3H), 1.85–1.97(m, 3H), 1.97–2.06(m, 3H), 2.06–2.20(m, 2H), 2.28(m, 2H), 2.55(m, 1H), 2.80(m, 3H), 3.90(d, 1H), 4.41(d, 1H), 7.09(m, 1H), 7.18(m, 3H), 7.20(s, 1H), 7.38(d, 1H), 7.46(s, 1H), 7.65(m, 3H), 8.43(d, 1H), 9.33(bs, 1H). LRMS: m/z (TSP⁺) 548.1, 550.1 [MH⁺] Microanalysis found: C, 63.76; H, 5.85; N,11.99. $C_{30}H_{31}Cl_2N_5O$; 0.25CH₂Cl₂ requires C, 63.77; H, 5.57; N, 12.29%. |
| 118[f] | 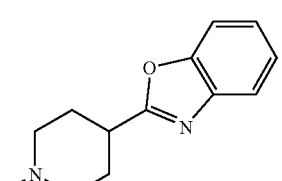 | 66 white foam | ¹Hnmr (CDCl₃, 400MHz) δ: 1.85–2.05(m, 11H), 2.30(m, 2H), 2.59(dd, 1H), 2.75–2.95(m, 3H), 3.94(d, 1H), 4.70(d, 1H), 7.12(dd, 1H), 7.23(d, 1H), 7.29(d, 2H), 7.41(d, 1H), 7.49(d, 1H), 7.50(s, 1H), 7.70(m, 3H), 8.50(d, 1H). LRMS: m/z (TSP⁺) 549.2, 551.1 [MH⁺] Microanalysis found: C, 64.55; H, 5.49; N, 9.89. $C_{30}H_{30}Cl_2N_4O_2$;0.06CH₂Cl₂ requires C, 64.41; H, 5.43; N, 9.96%. |

Starting amines:

[a]= N-(2-methoxyethyl)methylamine

[b]= N-[1-(3-azetidinyl)-4-phenyl-4-piperidinyl]acetamide dihydrochloride from preparation 34

[c]= 2-methyl-1-(4-piperidinyl)-1H-benzimidazole hydrochloride as prepared in J. Heterocycl. Chem. 1983; 20(3); 566

[d]= 1-(4-piperidinyl)-1,3-dihydro-2H-benzimidazol-2-one

[e]= 2-(4-piperidinyl)-1H-benzimidazole

[f]= 2-(4-piperidinyl)-1,3-benzoxazole

EXAMPLE 119

(5S)-5-(3,4-Dichlorophenyl)-1-(6-methoxy-2-pyridinyl)-5-{2-[3-(4-morpholinyl)-1-azetidinyl]ethyl}-2-piperidinone

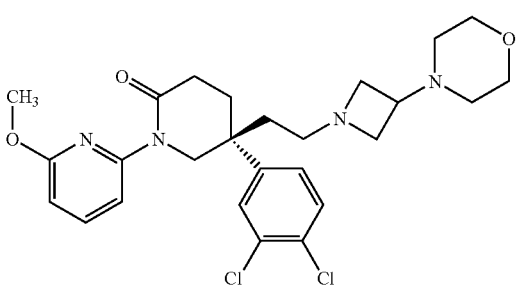

The title compound was obtained as a white foam in 80% yield from the aldehyde from preparation 18 and 3-morpholinoazetidine dihydrochloride (WO 9725322), following the procedure described in example 112.

$^1$Hnmr (CDCl$_3$, 400 MHz) δ: 1.68 (m, 2H), 1.79 (m, 1H), 2.05 (m, 2H), 2.21 (m, 6H), 2.50 (m, 1H), 2.65 (m, 2H), 2.85 (m, 1H), 3.34 (q, 2H), 3.65 (m, 4H), 3.73 (d, 1H), 3.96 (s, 3H), 4.59 (d, 1H), 6.58 (d, 1H), 7.21 (d, 2H), 7.39 (d, 1H), 7.55 (s, 1H), 7.59 (dd, 1H).

LRMS: m/z (TSP$^+$) 519.4, 521.4 [MH$^+$]

Microanalysis found: C, 58.97; H, 6.18; N, 10.47. C$_{26}$H$_{32}$Cl$_2$N$_4$O$_3$; 0.15CH$_2$Cl$_2$ requires C, 59.02; H, 6.12; N, 10.53%.

EXAMPLE 120

N-(1-{2-[(3S)-3-(3,4-Dichlorophenyl)-1-(6-methoxy-2-pyridinyl)-6-oxopiperidinyl]ethyl}-4-piperidinyl)-N-methylacetamide

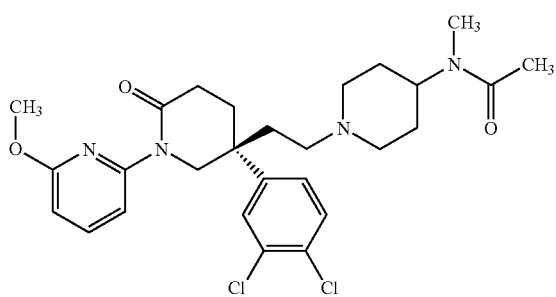

The title compound was obtained as a white foam in 63% yield from the aldehyde from preparation 18 and N-methyl-N-(4-piperidinyl)acetamide hydrochloride from preparation 60 following the procedure described in example 112.

$^1$Hnmr (CDCl$_3$, 400 MHz) δ: 1.50 (m, 4H), 1.80–2.20 (m, 7H), 2.05 (s, 3H), 2.28 (m, 2H), 2.55 (m, 1H), 2.78 (2×s, 3H), 2.80 (m, 2H), 3.41, 4.39 (2×m, 1H), 3.81 (m, 1H), 3.97 (s, 3H), 4.65 (d, 1H), 6.60 (d, 1H), 7.25 (m, 2H), 7.41 (m, 1H), 7.60 (m, 2H).

LRMS: m/z (TSP$^+$) 533.4, 535.4 [MH$^+$]

Microanalysis found: C, 59.50; H, 6.38; N, 10.16. C$_{27}$H$_{34}$Cl$_2$N$_4$O$_3$; 0.18CH$_2$Cl$_2$ requires C, 59.49; H, 6.31; N, 10.21%.

EXAMPLE 121

(5S)-5-(3,4-Dichlorophenyl)-5-{2-[(3R)-3-methoxypyrrolidinyl]ethyl}-1-(2-pyridinyl)-2-piperidinone

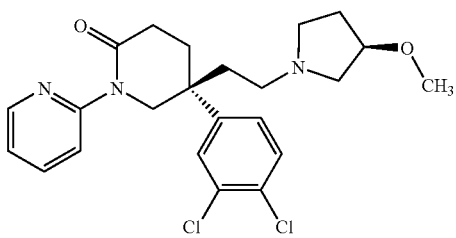

Triethylamine (0.1 ml, 1.6 mmol) was added to a solution of the aldehyde hydrochloride from preparation 11b (200 mg, 0.5 mmol) in dichloromethane (4 ml), followed by (3R)-3-methoxypyrrolidine trifluoroacetate from preparation 47 (186 mg, 0.7 mmol), and the solution stirred at room temperature for 10 minutes. Sodium triacetoxyborohydride (159 mg, 0.75 mmol) and acetic acid (60 μl, 2 mmol) were added, and the reaction stirred at room temperature for 18 hours. Methanol was added, the mixture stirred for 10 minutes, then concentrated under reduced pressure. The residue was partitioned between sodium carbonate solution and dichloromethane, the layers separated, and the organic phase evaporated under reduced pressure, to afford the title compound as a white gum, 199 mg.

$^1$Hnmr (CDCl$_3$, 400 MHz) δ: 1.74 (m, 1H), 1.84–2.00 (m, 3H), 2.10 (m, 2H), 2.25 (m, 4H), 2.44 (m, 1H), 2.55 (m, 3H), 3.20 (s, 3H), 3.80 (m, 1H), 4.10 (d, 1H), 4.54 (d, 1H), 7.08 (m, 1H), 7.19 (d, 1H), 7.39 (d, 1H), 7.42 (s, 1H), 7.65 (d, 2H), 8.46 (d, 1H).

LRMS: m/z (TSP$^+$) 448.0, 449.9 [MH$^+$]

EXAMPLE 122

(5S)-5-(3,4-Dichlorophenyl)-5-{2-[(3S)-3-methoxypyrrolidinyl]ethyl}-1-(2-pyridinyl)-2-piperidinone

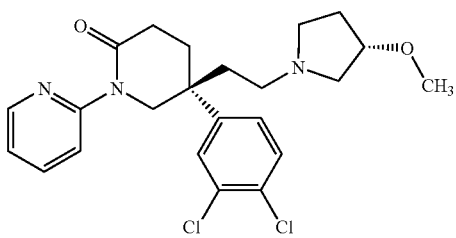

The title compound was obtained as a clear gum, in 85% yield from the aldehyde hydrochloride from preparation 11b and (3S)-3-methoxypyrrolidine trifluoroacetate from preparation 48, following the procedure described in example 121.

$^1$Hnmr (CDCl$_3$, 400 MHz) δ: 1.74 (m, 1H), 1.82–2.16 (m, 5H), 2.23 (m, 4H), 2.44 (m, 1H), 2.52 (m, 3H), 3.20 (s, 3H), 3.80 (m, 1H), 3.88 (d, 1H), 4.10 (d, 1H), 4.54 (d, 1H), 7.08 (m, 1H), 7.19 (d, 1H), 7.39 (d, 1H), 7.42 (s, 1H), 7.65 (d, 2H), 8.46 (d, 1H).

LRMS: m/z (TSP$^+$) 448.1, 450.1 [MH$^+$]

EXAMPLE 123 tert-Butyl 4-{2-[(3S)-3-(3,4-dichlorophenyl)-6-oxo-1-(2-pyridinyl)piperidinyl]ethyl}-1-piperazinecarboxylate

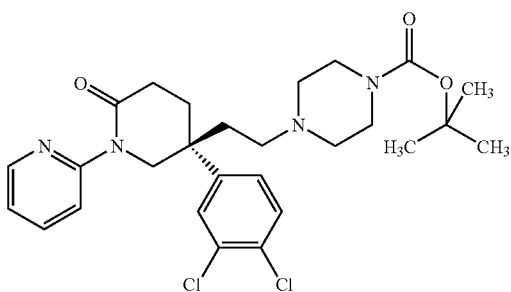

The title compound was obtained as a white foam in 73% yield from the aldehyde hydrochloride from preparation 11b and tert-butyl 1-piperazinecarboxylate, following a similar procedure to that described in example 121.

¹Hnmr (CDCl₃, 400 MHz) δ: 1.40 (s, 9H), 1.90 (m, 2H), 1.98 (m, 1H), 2.04–2.34 (m, 8H), 2.56 (m, 1H), 3.30 (m, 4H), 3.92 (d, 1H), 4.62 (d, 1H), 7.10 (m, 1H), 7.19 (d, 1H), 7.38 (d, 1H), 7.42 (s, 1H), 7.66 (d, 2H), 8.44 (d, 1H).

LRMS: m/z (TSP⁺) 533.3 [MH⁺]

EXAMPLE 124

(5S)-5-(3,4-Dichlorophenyl)-5-{2-[4-(2-methoxyethyl)-1-piperazinyl]ethyl}-1-(2-pyridinyl)-2-piperidinone

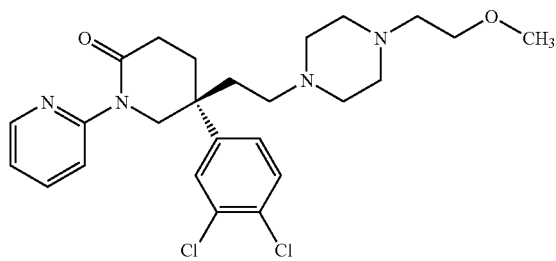

1-(2-Methoxyethyl)piperazine hydrochloride (90 mg, 0.5 mmol), followed by triethylamine (100 mg, 1 mmol) were added to a solution of the aldehyde hydrochloride from preparation 11b (200 mg, 0.5 mmol) in dichloromethane (2.5 ml), and stirring continued for 20 minutes. Acetic acid (50 mg, 0.83 mmol) and sodium triacetoxyborohydride (150 mg, 0.71 mmol) were then added and the reaction stirred at room temperature for 1 hour. Methanol (2 ml) was added, the mixture stirred for 20 minutes and then evaporated under reduced pressure. The residue was purified by column chromatography on silica gel using dichloromethane:methanol (93:7) as eluant. The product was redissolved in dichloromethane (10 ml), washed with 10% aqueous potassium carbonate solution (3 ml), then dried (Na₂SO₄) and evaporated under reduced pressure, to afford the title compound as a clear foam, 180 mg.

¹Hnmr (CDCl₃, 400 MHz) δ: 1.88 (m, 2H), 1.99 (m, 1H), 2.10 (m, 2H), 2.21–2.60 (m, 13H), 3.30 (s, 3H), 3.42 (t, 2H), 3.92 (d, 1H), 4.60 (d, 1H), 7.10 (m, 1H), 7.18 (d, 1H), 7.37 (d, 1H), 7.42 (s, 1H), 7.64 (m, 2H), 8.44 (m, 1H).

LRMS: m/z (ES⁺) 491 [MH⁺]

Microanalysis found: C, 61.10; H, 6.56; N, 11.40. C₂₅H₃₂Cl₂N₄O₂; 0.5H₂O requires C, 60.00; H, 6.65; N, 11.19%.

EXAMPLE 125

N-((3S)-1-{2-[(3S)-3-(3,4-Dichlorophenyl)-6-oxo-1-(2-pyridinyl)piperidinyl]ethyl}pyrrolidinyl)-N-methylacetamide

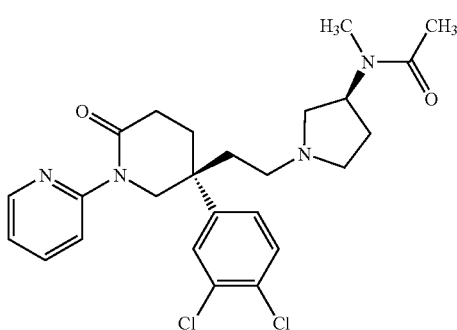

A mixture of the aldehyde from preparation 11a (200 mg, 0.5 mmol), the amine from preparation 44 (256 mg, 1.0 mmol), triethylamine (0.21 ml, 1.5 mmol), acetic acid (0.12 ml, 1.55 mmol) and sodium triacetoxyborohydride (211 mg, 1.0 mmol) in dichloromethane (50 ml) were stirred at room temperature in a STEM® block, for 24 hours. The mixture was washed with aqueous sodium bicarbonate solution and water, the organic layer filtered, dried (MgSO₄) and evaporated under reduced pressure. The crude product was purified by column chromatography on silica gel using dichloromethane:methanol:0.88 ammonia (95:5:1) as eluant, to give the title compound.

¹Hnmr (CDCl₃, 400 MHz) δ: 1.58 (m, 2H), 1.90–2.70 (m, 17H), 2.96 (m, 2H), 3.96 (d, 1H), 4.62 (m, 1H), 7.16 (d, 1H), 7.24 (m, 1H), 7.42 (d, 1H), 7.50 (s, 1H), 7.74 (s, 2H), 8.50 (d, 1H).

LRMS: m/z (TSP⁺) 489.1, 491.2 [MH⁺]

EXAMPLES 126 TO 130

The following compounds of general formula:

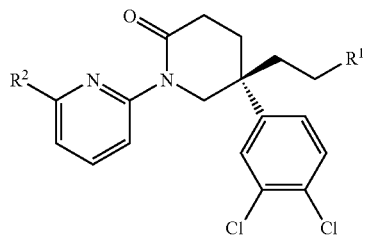

were prepared from the appropriate aldehydes and amines, according to the procedure described in example 125.

| Example | R¹ | R² | Data |
|---|---|---|---|
| 126[a] | (pyrrolidine with N-CH₃, N-acetyl-CH₃ substituent at 3-position) | H | ¹Hnmr (CDCl₃, 400 MHz) δ: 1.53–1.80 (m, 2H), 1.90–2.60 (m, 15H), 2.78 (m, 1H), 2.92 (m, 2H), 3.92 (d, 1H), 4.36, 5.20 (2xs, 1H), 4.62 (m, 1H), 7.12 (m, 1H), 7.20 (d, 1H), 7.40 (d, 1H), 7.45 (s, 1H), 7.72 (m, 2H), 8.48 (d, 1H). LRMS: m/z (TSP⁺) 489.1, 491.1 [MH⁺] Microanalysis found: C, 60.32; H, 6.11; N, 11.25. $C_{25}H_{30}Cl_2N_4O_2$; 0.5 $H_2O$ requires C, 60.24; H, 6.27; N, 11.24%. |
| 127[1b] | (pyrrolidine with 2-oxopyrrolidinyl at 3-position) | H | ¹Hnmr (CDCl₃, 400 MHz) δ: 1.90–2.40 (m, 15H), 2.58 (m, 2H), 2.80 (m, 1H), 3.36 (m, 2H), 3.94 (d, 1H), 4.64 (m, 2H), 7.16 (m, 1H), 7.20 (d, 1H), 7.42 (d, 1H), 7.48 (s, 1H), 7.70 (m, 2H), 8.48 (d, 1H). LRMS: m/z (TSP⁺) 501.1, 503.2 [MH⁺] Microanalysis found: C, 60.68; H, 6.16; N, 10.68. $C_{26}H_{30}Cl_2N_4O_2$: 0.2 $CH_2Cl_2$ requires C, 60.70; H, 5.91; N, 10.81%. |
| 128[1c] | (pyrrolidine with 2-oxopyrrolidinyl at 3-position) | H | ¹Hnmr (CDCl₃, 400 MHz) δ: 1.70–2.70 (m, 18H), 3.38 (m, 2H), 3.92 (d, 1H), 4.62 (d, 1H), 4.70 (bs, 1H), 7.16 (dd, 1H), 7.20 (d, 1H), 7.42 (d, 1H), 7.48 (s, 1H), 7.70 (m, 2H), 8.48 (d, 1H). LRMS: m/z (TSP⁺) 501.1, 503.1 [MH⁺] Microanalysis found: C, 60.74; H, 6.18; N, 10.79. $C_{26}H_{30}Cl_2N_4O_2$: 0.2$CH_2Cl_2$ requires C, 60.70; H, 5.91; N, 10.81%. |
| 129[d] | (pyrrolidine with N-CH₃, N-acetyl-CH₃ substituent at 3-position) | CH₃ | ¹Hnmr (CDCl₃, 400 MHz) δ: 1.70–2.80 (m, 22H), 2.90 (s, 2H), 3.90 (m, 1H), 4.58 (dd, 1H), 7.00 (d, 1H), 7.20 (d, 1H), 7.40 (m, 2H), 7.58 (m, 2H). LRMS: m/z (TSP⁺) 503.1 [MH⁺] |
| 130[e] | (pyrrolidine with N-CH₃, N-acetyl-CH₃ substituent at 3-position) | CH₃ | ¹Hnmr (CDCl₃, 400 MHz) δ: 1.90–2.80 (m, 22H), 2.90 (m, 2H), 4.88 (d, 1H), 4.34, 5.20 (2xbs, 1H), 7.00 (d, 1H), 7.22 (d, 1H), 7.40 (m, 2H), 7.60 (m, 2H). LRMS: m/z (TSP⁺) 503.2 [MH⁺] Microanalysis found: C, 60.28; H, 6.69; N, 10.99. $C_{26}H_{32}Cl_2N_4O_2$; 0.2$CH_2Cl_2$ requires C, 60.46; H, 6.27; N, 10.76% |

[1] 1.5 mmol amine/1 mmol NaBH(OAc)₃/1 mmol Et₃N/1.05 mmol AcOH

Starting amines:

[a] N-methyl-N-[(3S)-pyrrolidinyl]acetamide trifluoroacetamide from preparation 43

[b] 1-[(3S)-pyrrolidin-3-yl]-2-pyrrolidine from preparation 53

[c] 1-[(3R)-pyrrolidin-3-yl]-2-pyrrolidine from preparation 54

[d] N-methyl-N-[(3R)-pyrrolidinyl]acetamide trifluoroacetate from preparation 43

[e] N-methyl-N-[(3S)-pyrrolidinyl]acetamide trifluoroacetate from preparation 44

EXAMPLE 131

(5S)-5-(3,4-Dichlorophenyl)-1-(6-methyl-2-pyridinyl)-5-{2-[3-(4-morpholinyl)-1-azetidinyl]ethyl}-2-piperidinone

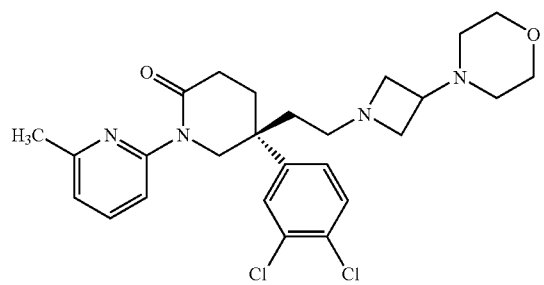

A mixture of the aldehyde from preparation 12a (2.0 g, 5.3 mmol), 3-morpholinoazetidine dihydrochloride (WO 9725322) (1.25 g, 5.83 mmol), triethylamine (1.84 ml, 13.3 mmol) and titanium isopropoxide (16 ml, 53 mmol) in ethanol (20 ml), was stirred at room temperature for 18 hours. Sodium borohydride (320 mg, 7.95 mmol) in ethanol (19 ml) was then added and the reaction stirred for 30 minutes. Sodium hydroxide was added, the resulting precipitate filtered off, and washed with ethyl acetate. The filtrate was washed with water (2×) and brine (2×), dried (MgSO$_4$) and evaporated under reduced pressure. The residual gum was purified by column chromatography on silica gel using an elution gradient of dichloromethane:methanol (100:0 to 99:1) to afford the title compound as a white solid, 1.58 g.

$^1$Hnmr (CDCl$_3$, 400 MHz) δ: 1.72 (m, 1H), 1.82 (m, 1H), 2.14 (m, 2H), 2.24 (m, 7H), 2.56 (m, 1H), 2.58 (s, 3H), 2.75 (m, 2H), 2.90 (m, 1H), 3.40 (m, 2H), 3.65 (m, 4H), 3.88 (d, 1H), 4.50 (d, 1H), 7.00 (d, 1H), 7.20 (d, 1H), 7.40 (d, 2H), 7.55 (s, 1H), 7.60 (dd, 1H).

LRMS m/z (TSP$^+$) 503.6, 505.2 [MH$^+$]

EXAMPLES 132 TO 134

The compounds of the general structure:

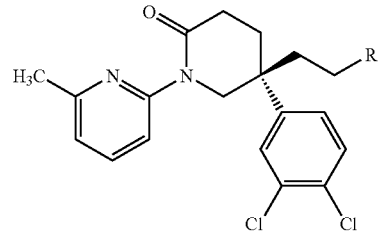

were prepared from the aldehyde from preparation 12a and the appropriate amines, following a similar procedure to that described in example 131.

| Example | R | Yield (%) | Data |
|---|---|---|---|
| 132[a] | ![structure with SO$_2$CH$_3$ on piperidine-azetidine] | 21 white solid | $^1$Hnmr (CDCl$_3$, 400 MHz) δ: 1.10–1.90 (m, 9H), 2.10 (m, 3H), 2.25 (m, 3H), 2.56 (s, 3H), 2.56 (m, 3H), 2.74 (s, 3H), 3.28 (m, 2H), 3.75 (d, 2H), 3.84 (d, 1H), 4.50 (d, 1H), 6.98 (d, 1H), 7.20 (d, 1H), 7.28 (d, 1H), 7.40 (dd, 1H), 7.55 (m, 2H). LRMS : m/z (TSP$^+$) 580.1, 582.1 [MH$^+$] |
| 133[b] | ![structure with SO$_2$CH$_3$ on piperazine-azetidine] | | $^1$Hnmr (CDCl$_3$, 400 MHz) δ: 1.80 (m, 1H), 2.10–2.40 (m, 11H), 2.55 (s, 4H), 2.75 (m, 5H), 2.94 (m, 1H), 3.20 (m, 4H), 3.40 (d, 1H), 3.88 (d, 1H), 4.64 (d, 1H), 7.00 (d, 1H), 7.20 (d, 1H), 7.40 (d, 2H), 7.54 (s, 1H), 7.60 (dd, 1H). LRMS: m/z (ES$^+$) 580, 582 [MH$^+$] |
| 134[1c] | ![4-hydroxy-4-phenylpiperidine structure] | 9 white solid | $^1$Hnmr (CDCl$_3$, 400 MHz) δ: 1.50–2.60 (m, 20H), 3.95 (d, 1H), 4.62 (d, 1H), 7.00 (d, 1H), 7.25 (d, 2H), 7.35 (d, 2H), 7.42 (m, 4H), 7.60 (dd, 2H). LRMS: m/z (TSP$^+$) 538.4 [MH$^+$] Microanalysis found: C, 64.82; H, 6.11; N, 7.49. C$_{30}$H$_{33}$Cl$_2$N$_3$O$_2$; 0.1 (CH$_2$CH$_2$)$_2$O; 0.9H$_2$O requires C, 66.91; H, 6.18; N, 7.80%. |

[1]purified by column chromatography on silica gel using dichloromethane:methanol:0.88 ammonia (90:10:0.05) as eluant and triturated with diethyl ether.
Starting amines:
[a]4-(3-azetidinyl)-1-(methylsulfonyl)piperidine hydrochloride as prepared in EP 992493
[b]1-(3-azetidinyl)-4-(methylsulphonyl)piperazine trifluoroacetate as prepared in WO 9725322
[c]4-hydroxy-4-phenylpiperidine

EXAMPLE 135a (5S)-5-(3,4-Dichlorophenyl)-1-(6-methyl-2-pyridinyl)-5-{2-[3-(4-hydroxypiperidinyl)azetidinyl]ethyl}-2-piperidinone

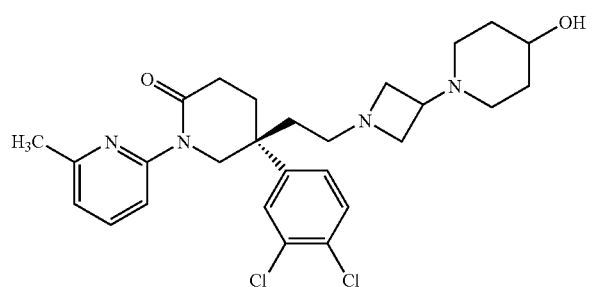

3-(4-hydroxypiperidinyl)azetidine trifluoroacetate (WO 96/05193—preparation 77)(25.2 gm, 65 mmol) was dissolved in tetrahydrofuran (100 ml) and added to a solution of the aldehyde from preparation 12a (24.8 gm, 65 mmol) in dichloromethane (300 ml). Sodium triacetoxyborohydride (21 gm, 98 mmol) was added and the reaction stirred at room temperature for 18 hours. The reaction was concentrated under reduced pressure and the resulting orange oil was dissolved in ethyl acetate (500 ml), washed with 2N sodium hydroxide solution (200 ml), the aqueous layer extracted with ethyl acetate (2×200 ml), the combined organic extracts were dried (MgSO$_4$), and concentrated under reduced pressure. The crude product was purified by column chromatography on silica gel using dichloromethane:methanol:0.88 ammonia (90:10:1) as eluant to afford the title compound as a white foam (17 gm).

$^1$Hnmr (CDCl$_3$, 400 MHz) δ: 1.52 (m, 3H), 1.70 (m, 1H), 1.85 (m, 3H), 1.95 (m, 2H), 2.15 (m, 2H), 2.25 (m, 3H), 2.55 (m, 6H), 2.66 (m, 2H), 2.86 (t, 1H), 3.42 (m, 2H), 3.70 (m, 1H), 3.84 (d, 1H), 4.50 (d, 1H), 7.00 (d, 1H), 7.20 (d, 1H), 7.40 (dd, 2H), 7.58 (s, 1H), 7.60 (dd, 1H).

LRMS: m/z (TSP$^+$) 517.3 [MH$^+$]

EXAMPLE 135b (5S)-5-(3,4-Dichlorophenyl)-1-(6-methyl-2-pyridinyl)-5-{2-[3-(4-hydroxypiperidinyl)azetidinyl]ethyl}-2-piperidinone bisfumarate

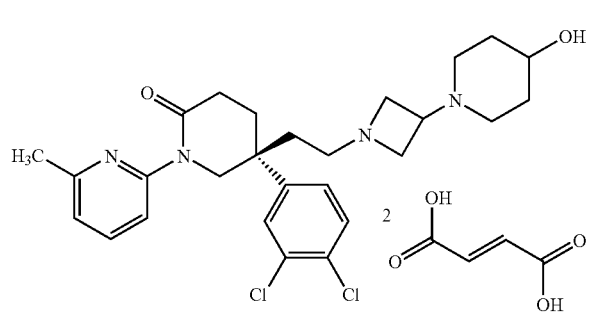

Fumaric acid (8 gm, 69 mmol) was dissolved in a mixture of water (3.4 ml, 190 mmol) and tetrahydrofuran (100 ml) before adding to a solution of the title compound from example 135a (24.7 gm, 47.7 mmol) in tetrahydofuran (50 ml). Resulting solution was allowed to stand at room temperature for 1 hour, during which time a white precipitate had formed. Mixture filtered, filter cake washed with tetrahydrofuran (30 ml), diethyl ether (2×200 ml) and dried at 50° C. for 48 hours to give a white solid (26.4 gm). Solid recrystallised from refluxing 2% (vol/vol) aqueous tetrahydrofuran (250 ml), upon cooling mixture filtered, filter cake washed with tetrahydrofuran (2×100 ml), diethyl ether (3×500 ml) and air dried for 20 minutes. Resulting solid was slurried in acetone (100 ml) for 18 hours, filtered washed with diethyl ether and dried for 48 hours at 50° C. under reduced pressure (6 mbar) to give the title compound as a fine white solid.

$^1$Hnmr (CD$_3$OD, 400 MHz) δ: 1.54 (m, 2H), 1.82 (m, 2H), 1.94 (m, 1H), 2.05 (m, 1H), 2.14 (m, 2H), 2.21 (m, 2H), 2.38 (m, 1H), 2.54 (m, 4H), 2.66 (m, 2H), 2.73 (m, 1H), 2.94 (m, 1H), 3.25 (m, 1H), 3.65 (m, 3H), 3.90 (d, 1H), 4.00 (m, 2H), 4.48 (d, 1H), 6.69 (s, 3H), 7.13 (d, 1H), 7.25 (d, 1H), 7.44 (d, 1H), 7.54 (d, 1H), 7.68 (t, 1H), 7.81 (s, 1H).

LRMS: m/z (TSP$^+$) 517.3 [MH$^+$]

Microanalysis found: C, 55.73; H, 5.67; N, 7.48. C$_{27}$H$_{34}$Cl$_2$N$_4$O$_2$; 2.C$_4$H$_4$O$_4$; 0.25H$_2$O requires C, 55.74; H, 5.68; N, 7.43%.

Mpt. 175.5–177° C.

EXAMPLE 136

(5S)-5-(3,4-Dichlorophenyl)-1-(5-methyl-2-pyridinyl)-5-{2-[3-(4-morpholinyl)-1-azetidinyl]ethyl}-2-piperidinone

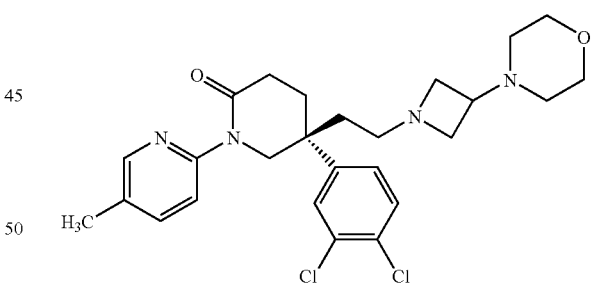

The title compound was prepared as a yellow solid in 6% yield from the aldehyde from preparation 14 and 3-morpholinoazetidine dihydrochloride (WO 9725322), following a similar procedure to that described in example 131, except ethyl acetate:pentane (10:90 to 100:0) was used as the column eluant.

$^1$Hnmr (CDCl$_3$, 400 MHz) δ: 1.75 (m, 1H), 1.85 (m, 1H), 2.20 (m, 9H), 2.38 (s, 3H), 2.58 (m, 1H), 2.76 (m, 2H), 2.95 (m, 1H), 3.42 (m, 2H), 3.68 (m, 4H), 3.90 (d, 1H), 4.50 (d, 1H), 7.12 (d, 1H), 7.42 (d, 1H), 7.50 (s, 1H), 7.58 (m, 2H), 8.32 (s, 1H).

LRMS: m/z (TSP$^+$) 503.3, 504.9 [MH$^+$]

EXAMPLE 137

(5S)-5-(3,4-Dichlorophenyl)-1-(6-ethyl-2-pyridinyl)-5-{2-[3-(4-morpholinyl)-1-azetidinyl]ethyl}-2-piperidinone

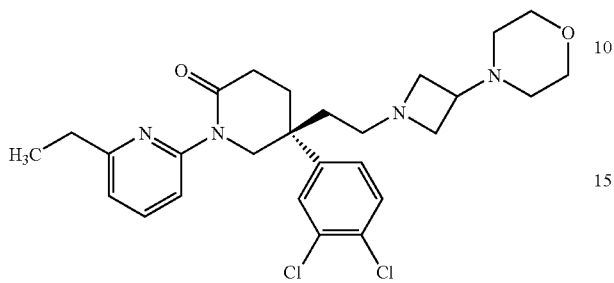

The title compound was prepared as a white solid in 37% yield, from the aldehyde from preparation 16, and 3-morpholinoazetidine dihydrochloride (WO 9725322), following the procedure described in example 131.

EXAMPLE 138

N-(1-{2-[(3S)-3-(3,4-Dichlorophenyl)-6-oxo-1-(3-pyridinyl)piperidinyl]ethyl}-4-piperidinyl)-N-methylacetamide

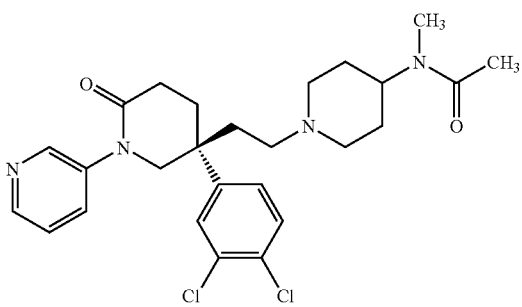

Potassium carbonate (390 mg, 2.82 mmol), copper (90 mg, 1.41 mmol) and 3-bromopyridine (680 μl, 7.06 mmol) were added to the amine from preparation 83 (300 mg, 0.70 mmol) and the mixture stirred at 140° C. for 20 hours. The mixture was partitioned between water (100 ml) and ethyl acetate (100 ml), and the layers separated. The aqueous phase was extracted with ethyl acetate, the combined organic solutions washed with water, then brine, and dried ($Na_2SO_4$) and evaporated under reduced pressure. The crude oil was purified by column chromatography on silica gel using an elution gradient of dichloromethane:methanol (95:5 to 85:15) to afford the title compound as a yellow oil, 80 mg.

$^1$Hnmr ($CDCl_3$, 400 MHz) δ: 1.46 (m, 3H), 1.63 (m, 1H), 1.88 (m, 3H), 2.00 (s, 3H), 2.20 (m, 1H), 2.37 (m, 2H), 2.58 (m, 1H), 2.75 (m, 5H), 3.40 (s, 3H), 3.88 (d, 1H), 4.03 (m, 1H), 4.37 (m, 1H), 7.10 (d, 1H), 7.30 (m, 2H), 7.40 (d, 1H), 7.60 (d, 1H), 8.45 (s, 1H), 8.53 (s, 1H).

LRMS: m/z ($ES^+$) 525, 527 [$MH^+$]

Microanalysis found: C, 58.52; H, 6.18; N, 10.31. $C_{26}H_{32}Cl_2N_4O_2$; $0.5CH_2Cl_2$ requires C, 58.30; H, 6.09; N, 10.26%.

EXAMPLE 139

N-(1-{2-[(3S)-3-(3,4-Dichlorophenyl)-1-(6-methyl-3-pyridinyl)-6-oxopiperidinyl]ethyl}-4-piperidinyl)-N-methylacetamide

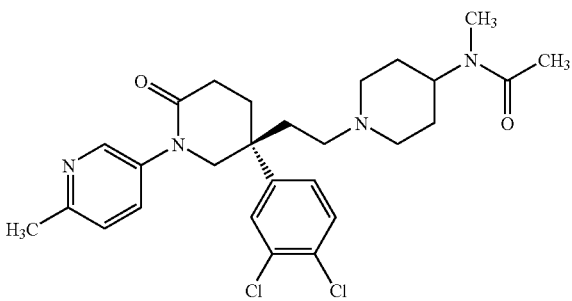

The title compound was obtained as a black solid in 71% yield, from the amine from preparation 83 and 5-bromo-2-methylpyridine, following a similar procedure to that described in example 138, except 1-methyl-2-pyrrolidinone was used as the reaction solvent.

$^1$Hnmr ($CD_3OD$, 400 MHz) δ: 1.45 (m, 1H), 1.58 (m, 2H), 1.65 (m, 1H), 1.85–2.14 (m, 10H), 2.24 (m, 2H), 2.42 (m, 1H), 2.56 (s, 3H), 2.74 (s, 1H), 2.82 (m, 4H), 3.58 (m, 0.2H), 4.0 (d, 1H), 4.10 (d, 1H), 4.24 (m, 0.8H), 7.38 (d, 2H), 7.57 (d, 1H), 7.60 (s, 1H), 7.63 (dd, 1H), 8.35 (s, 1H).

LRMS: m/z ($ES^+$) 539, 541 [$MNa^+$]

Microanalysis found: C, 61.39; H, 6.59; N, 10.41. $C_{27}H_{34}Cl_2N_4O_2$; $0.6H_2O$ requires C, 61.38; H, 6.72; N, 10.60%.

EXAMPLE 140

N-(1-{2-[(3S)-3-(3,4-Dichlorophenyl)-6-oxo-1-(2-pyrazinyl)piperidinyl]ethyl}-4-piperidinyl)-N-methylacetamide

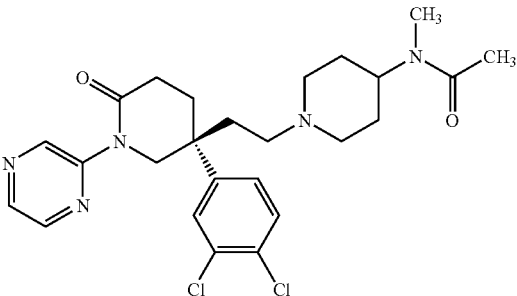

A mixture of the amine from preparation 83 (300 mg, 0.70 mmol), potassium tert-butoxide (160 mg, 1.43 mmol) and chloropyrazine (260 μl, 2.8 mmol) in N-methylpyrrolidine (5 ml) was stirred at 100° C. for 72 hours. The cooled mixture was partitioned between water (100 ml) and ethyl acetate (100 ml), and the layers separated. The aqueous phase was extracted with ethyl acetate, the combined organic solutions washed with water and brine, then dried ($MgSO_4$) and evaporated under reduced pressure. The crude product was purified by column chromatography on silica gel using an elution gradient of dichloromethane:methanol: 0.88 ammonia (99:1:0.1 to 90:10:1) to afford the title compound as a brown, glass-like solid, 45 mg.

¹Hnmr (CDCl₃, 400 MHz) δ: 1.55 (m, 4H), 1.83–2.20 (m, 11H), 2.26–2.43 (m, 2H), 2.60–2.82 (m, 5H), 3.92 (d, 1H), 4.38 (m, 1H), 4.64 (d, 1H), 7.18 (d, 1H), 7.39 (d, 1H), 7.43 (s, 1H), 8.35 (s, 1H), 8.39 (s, 1H), 9.19 (s, 1H).

LRMS: m/z (ES⁺) 526, 528 [MH⁺]

Microanalysis found: C, 52.88; H, 5.29; N, 12.27. C₂₅H₃₁Cl₂N₅O₂;CH₂Cl₂ requires C, 52.98; H, 5.64; N, 11.88%.

EXAMPLE 141

N-(1-{2-[(3S)-3-(3,4-Dichlorophenyl)-1-(6-methyl-2-pyrazinyl)-6-oxopiperidinyl]ethyl}-4-piperidinyl)-N-methylacetamide

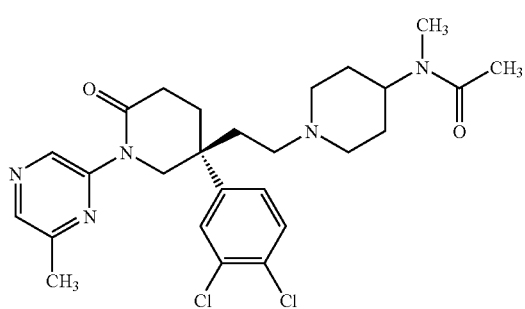

The title compound was obtained as a brown solid in 4% yield, from the amine from preparation 83 and 2-chloro-6-methylpyrazine (Tetrahedron 1972; 28; 4155), following a similar procedure to that described in example 140.

¹Hnmr (CDCl₃, 400 MHz) δ: 1.56 (m, 3H), 1.81–2.19 (m, 11H), 2.32 (m, 2H), 2.58 (s, 3H), 2.62 (m, 1H), 2.80 (m, 5H), 3.40 (m, 0.2H), 3.85 (dd, 1H), 4.42 (m, 0.8H), 4.58 (dd, 1H), 7.18 (d, 1H), 7.40 (d, 1H), 7.50 (s, 1H), 8.22 (s, 1H), 8.86 (s, 1H).

LRMS: m/z (ES⁺) 540, 542 [MNa⁺]

EXAMPLE 142

(5S)-5-(3,4-Dichlorophenyl)-5-(2-{methyl[(1R)-1-phenylethyl]amino}ethyl)-1-(2-pyridinyl)-2-piperidinone dihydrochloride

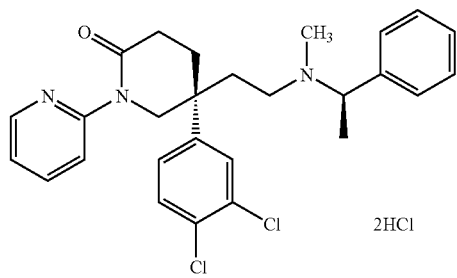

Formaldehyde (75 μl, 37% aq, 0.92 mmol) was added to a solution of the amine from example 37 (160 mg, 0.30 mmol) in dichloromethane (25 ml), and the solution stirred for 5 minutes. Sodium triacetoxyborohydride (63 mg, 0.30 mmol) was added and the reaction stirred at room temperature for 18 hours. Tlc analysis showed starting material remaining, so additional formaldehyde (0.4 ml, 37% aq, 4.93 mmol) and sodium triacetoxyborohydride (62 mg, 0.29 mmol) were added, and the reaction stirred for an hour. The reaction was washed with saturated aqueous sodium bicarbonate solution (25 ml), brine (10 ml), dried (MgSO₄) and concentrated under reduced pressure. The residual foam was redissolved in dichloromethane (10 ml), and treated with 1N ethereal hydrochloric acid (5 ml). This solution was then evaporated under reduced pressure, to afford the title compound as a white foam, 158 mg.

¹Hnmr (CD₃OD, 400 MHz) δ: 1.63 (t, 3H), 2.06–3.00 (m, 11H), 4.04–4.65 (m, 3H), 7.07–7.73 (m, 9H), 7.90 (m, 1H), 8.40 (m, 1H), 8.59 (m, 1H).

LRMS: m/z (TSP⁺) 482.1, 484.1 [MH⁺]

EXAMPLE 143

(5S)-5-(3,4-Dichlorophenyl)-5-(2-{methyl [(1S)-1-phenylethyl]amino}ethyl)-1-(2-pyridinyl)-2-piperidinone dihydrochloride

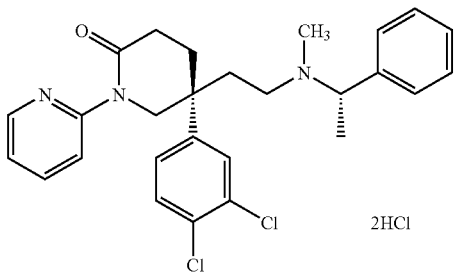

The title compound was prepared in 91% yield from the amine from example 38, following the procedure described in example 142.

¹Hnmr (CD₃OD, 400 MHz) δ: 1.63 (t, 3H), 2.08–2.97 (m, 11H), 4.10–4.23 (m, 1H), 4.28 (m, 0.5H), 4.41 (m, 1H), 4.60 (m, 0.5H), 7.18–7.63 (m, 8H), 7.72 (dd, 1H), 7.92 (dd, 1H), 8.44 (dd, 1H), 8.60 (m, 1H).

LRMS: m/z (TSP⁺) 482.1, 484.1 [MH⁺]

EXAMPLE 144

(5S)-5-(3,4-Dichlorophenyl)-5-(2-{methyl[(1R)-1-phenylethyl]amino}ethyl)-1-(6-methyl-2-pyridinyl)-2-piperidinone Dihydrochloride

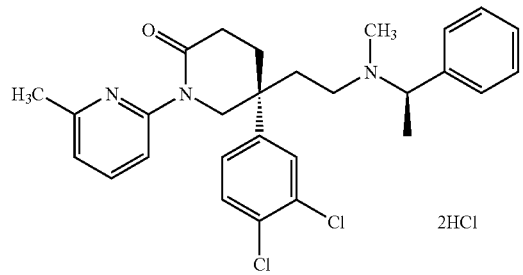

The title compound was prepared from the amine from example 41 as a white solid, following a similar procedure to that described in example 143.

¹Hnmr (CD₃OD, 400 MHz) δ: 1.63 (t, 3H), 2.07–2.97 (m, 14H), 4.08 (d, 1H), 4.22 (q, 1H), 4.37 (m, 1H), 7.16–7.75 (m, 10H), 8.25–8.40 (m, 1H).

LRMS: m/z (TSP⁺) 496.1, 498.2 [MH⁺]

Microanalysis found: C, 53.27; H, 6.15; N, 6.51. $C_{28}H_{31}Cl_2N_3O;2HCl;3.5H_2O$ requires C, 53.18; H, 5.90; N, 6.64%

EXAMPLE 145

(5S)-5-(3,4-Dichlorophenyl)-5-(2-{methyl[3-(4-morpholinyl)propyl]amino}ethyl)-1-(2-pyridinyl)-2-piperidinone trihydrochloride

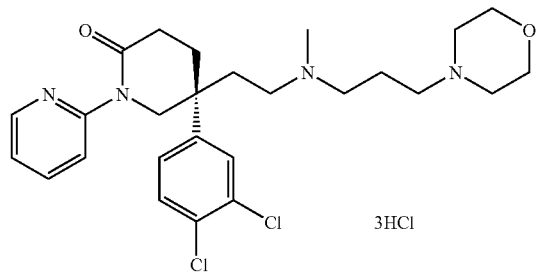

Triethylamine (0.5 ml) was added to a suspension of the amine from example 36 (267 mg, 0.44 mmol) in dichloromethane (20 ml), followed by acetic acid (0.5 ml), formaldehyde (0.36 ml, 4.44 mmol) and finally sodium triacetoxyborohydride (94.6 mg, 0.45 mmol), and the reaction stirred at room temperature for 2 hours. The mixture was washed with saturated aqueous sodium bicarbonate solution (50 ml), brine (25 ml), dried (MgSO₄) and concentrated under reduced pressure. The crude product was redissolved in dichloromethane, 1N ethereal hydrochloric acid added and the solution then evaporated under reduced pressure to afford the title compound as a white foam, 258 mg.

¹Hnmr (CD₃OD, 400 MHz) δ: 2.22 (m, 2H), 2.32–2.59 (m, 6H), 2.78–2.90 (m, 5H), 3.10–3.20 (m, 5H), 3.23 (m, 1H), 3.52 (m, 2H), 3.86 (m, 2H), 4.14 (d, 2H), 4.30 (m, 1H), 4.48 (m, 1H), 7.46 (d, 1H), 7.60 (d, 1H), 7.65 (s, 1H), 7.80 (m, 1H), 8.15 (m, 1H), 8.04–8.56 (m, 2H).

EXAMPLE 146

(5S)-5-(3,4-Dichlorophenyl)-5-{2-[methyl(2-pyridinylmethyl)amino]ethyl}-1-(2-pyridinyl)-2-piperidinone trihydrochloride

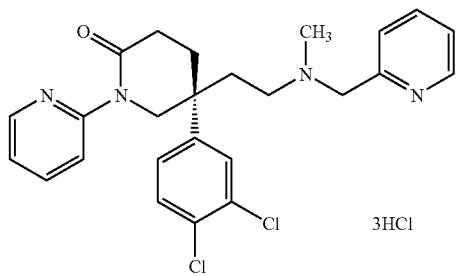

The title compound was prepared as a white foam in 90% yield from the amine from example 56, following the procedure described in example 145.

¹Hnmr (CD₃OD, 400 MHz) δ: 2.30–2.60 (m, 5H), 2.81 (m, 1H), 2.90 (s, 3H), 2,98 (m, 1H), 3.17 (m, 1H), 4.30 (d, 1H), 4.41 (d, 1H), 4.58 (s, 2H), 7.40 (d, 1H), 7.57 (d, 1H), 7.64 (m, 2H), 7.72 (d, 1H), 7.82 (dd, 1H), 8.08 (m, 2H), 8.62 (m, 3H).

LRMS: m/z (TSP⁺) 471.1, 473.1 [MH⁺]

Microanalysis found: C, 43.15; H, 5.29; N, 7.64%. $C_{25}H_{26}Cl_2N_4O; 3HCl;3.5H_2O; CH_2Cl_2$ requires C, 42.96; H, 5.27; N, 7.71%.

EXAMPLE 147

(5S)-5-{2-[3-(4-Amino-1-piperidinyl)-1-azetidinyl]ethyl}-5-(3,4-dichlorophenyl)-1-(2-pyridinyl)-2-piperidinone

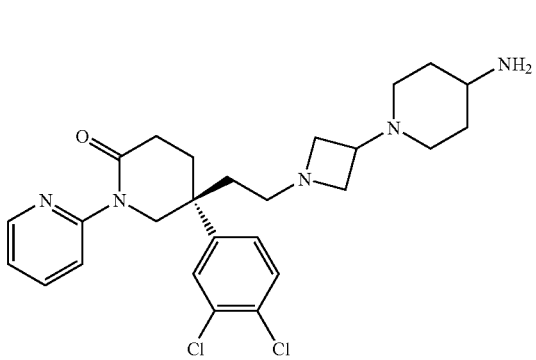

Trifluoroacetic acid (10 ml) was added to an ice-cooled solution of the protected amine from preparation 84 (760 mg, 1.26 mmol) in dichloromethane (5 ml), and the solution stirred at 0° C. for 2 hours. The solution was poured into ice-cooled water (200 ml), basified using 2N sodium hydroxide solution, and extracted with dichloromethane (3×200 ml). The combined organic solutions were washed with brine, dried (MgSO₄), and evaporated under reduced pressure to give the title compound as a white foam, 540 mg.

¹Hnmr (CDCl₃, 300 MHz) δ: 1.34 (m, 2H), 1.81 (m, 8H), 2.13 (m, 2H), 2.30 (m, 3H), 2.52–2.75 (m, 6H), 2.87 (m, 1H), 3.42 (m, 2H), 3.90 (d, 1H), 4.56 (d, 1H), 7.20 (m, 2H), 7.43 (m, 2H), 7.72 (m, 2H), 8.52 (d, 1H).

LRMS: m/z (ES⁺) 502, 504 [MH⁺]

EXAMPLE 148

(5S)-5-(3,4-Dichlorophenyl)-5-[2-(1-piperazinyl)ethyl]-1-(2-pyridinyl)-2-piperidinone

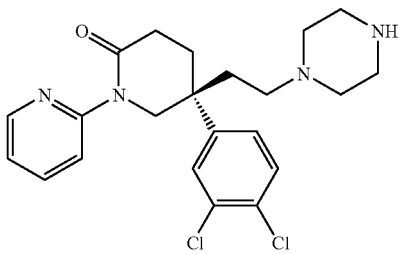

A solution of the protected amine from example 123 (923 mg, 1.78 mmol) in 4M HCl in dioxan (50 ml) was stirred at room temperature for 18 hours. The reaction mixture was concentrated under reduced pressure and the residue partitioned between sodium bicarbonate solution and dichloromethane. The layers were separated, the organic phase dried (MgSO₄) and evaporated under reduced pressure to give a yellow solid, 831 mg.

A sample (50 mg) was purified by column chromatography on silica gel using dichloromethane:methanol:0.88 ammonia (90:10:1) as eluant to afford the title compound as a clear oil.

¹Hnmr (CDCl₃, 400 MHz) δ: 1.83–2.16 (m, 6H), 2.23 (m, 5H), 2.58 (m, 1H), 2.89 (m, 4H), 3.89 (d, 1H), 4.60 (d, 1H), 7.12 (s, 1H), 7.19 (d, 1H), 7.38 (d, 1H), 7.44 (s, 1H), 7.68 (s, 2H), 8.45 (d, 1H).

LRMS: m/z (TSP⁺) 433.1, 43.1 [MH⁺]

EXAMPLE 149

(5S)-5-[2-(4-Amino-1-piperidinyl)ethyl]-5-(3,4-dichlorophenyl)-1-(2-pyridinyl)-2-piperidinone

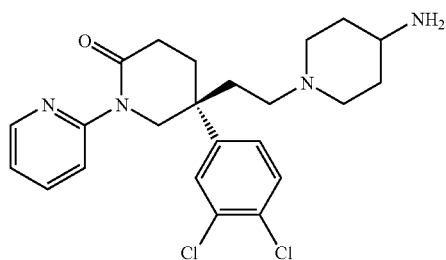

A solution of the protected amine from example 54 (577 mg, 1.05 mmol) in 4M HCl in dioxan (10 ml) was stirred at room temperature for 2 hours. The mixture was evaporated under reduced pressure and the residue partitioned between 10% aqueous sodium carbonate solution and diethyl ether, and the layers separated. The aqueous phase was extracted with diethyl ether, then dichloromethane, the combined organic solutions dried (MgSO₄) and evaporated under reduced pressure, to give the title compound as a white foam, 465 mg.

¹Hnmr (CDCl₃, 400 MHz) δ: 1.42 (m, 2H), 1.83–1.98 (m, 7H), 2.13 (m, 2H), 2.29 (m, 2H), 2.59 (m, 1H), 2.73 (m, 3H), 3.05 (m, 2H), 3.91 (d, 1H), 4.56 (d, 1H), 7.13 (dd, 1H), 7.21 (d, 1H), 7.40 (d, 1H), 7.46 (s, 1H), 7.68 (m, 2H), 8.48 (d, 1H).

LRMS: m/z (TSP⁺) 447.1, 449.1 [MH⁺]

EXAMPLE 150

(5S)-5-(3,4-Dichlorophenyl)-5-{2-[4-(methylamino)-1-piperidinyl]ethyl}-1-(2-pyridinyl)-2-piperidinone dihydrochloride

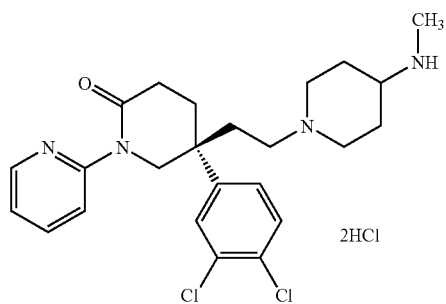

Hydrogen chloride was bubbled through a solution of the protected amine from example 99 (340 mg, 0.607 mmol) in dichloromethane (50 ml) for 5 minutes. The mixture was evaporated under reduced pressure to afford a quantitative amount of the title compound as a white foam.

¹Hnmr (CD₃OD, 400 MHz) δ: 1.98 (m, 2H), 1.98–2.58 (m, 8H), 2.70 (s, 3H), 2.81 (m, 2H), 3.00 (m, 2H), 3.38 (m, 2H), 3.62 (m, 2H), 4.22 (d, 1H), 4.39 (d, 1H), 7.41 (m, 1H), 7.58 (d, 1H), 7.66 (s, 1H), 7.78 (m, 1H), 8.02 (d, 1H), 8.58 (m, 1H).

LRMS: m/z (TSP⁺)461.1, 463.1 [MH⁺]

EXAMPLE 151

N-[1-(1-{2-[(3S)-3-(3,4-Dichlorophenyl)-6-oxo-1-(2-pyridinyl)piperidinyl]ethyl}-3-azetidinyl)-4-piperidinyl]acetamide

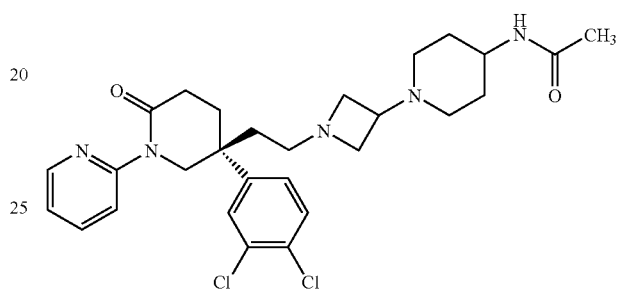

Triethylamine (85 mg, 0.84 mmol) and acetic anhydride (74 mg, 0.63 mmol) were added to a solution of the amine from example 147 (210 mg, 0.42 mmol) in dichloromethane (100 ml), and the reaction stirred at room temperature for 20 minutes. The solution was washed with 2N sodium hydroxide solution, and the aqueous layer extracted with dichloromethane (2×50 ml). The combined organic solutions were dried (MgSO₄), evaporated under reduced pressure and the residue azeotroped with dichloromethane (4×200 ml), to afford the title compound as a white foam, 206 mg.

¹Hnmr (CDCl₃, 300 MHz) δ: 1.72–1.99 (m, 10H), 2.08–2.23 (m, 3H), 2.23–2.42 (m, 3H), 2.54–2.69 (m, 3H), 2.78 (m, 2H), 2.93 (m, 1H), 3.49 (m, 2H), 3.78 (m, 1H), 3.92 (d, 1H), 4.56 (d, 1H), 5.36 (m, 1H), 7.17 (m, 1H), 7.21 (d, 1H), 7.44 (m, 2H), 7.74 (m, 2H), 8.51 (m, 1H).

LRMS: m/z (ES⁺) 544, 546 [MH⁺]

Microanalysis found: C, 57.75; H, 7.00; N, 11.80. C₂₈H₃₅Cl₂N₅O₂; 2H₂O requires C, 57.93; H, 6.77; N, 12.06%.

EXAMPLE 152

(5S)-5-(3,4-Dichlorophenyl)-5-[2-(4-propionyl-1-piperazinyl)ethyl]-1-(2-pyridinyl)-2-piperidinone

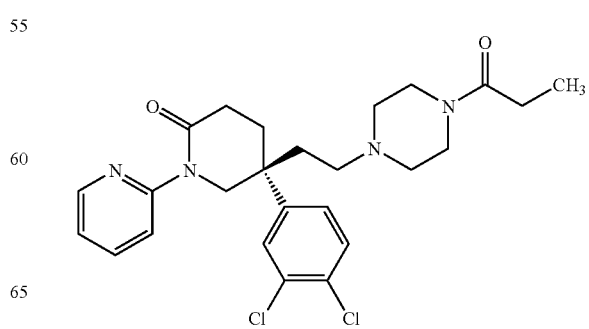

A mixture of the piperazine from example 148 (168 mg, 0.39 mmol), propionyl chloride (34 μl, 0.39 mmol) and triethylamine (54 μl, 0.39 mmol) in dichloromethane (10 ml) was stirred at room temperature for an hour. The mixture was washed with water, and the aqueous solution extracted with dichloromethane. The combined organic solutions were dried (MgSO$_4$) and evaporated under reduced pressure. The crude product was purified by column chromatography on silica gel using dichloromethane:methanol:0.88 ammonia (95:5:0.5) as eluant to afford the title compound as a clear gum, 52 mg.

$^1$Hnmr (CDCl$_3$, 400 MHz) δ: 1.09 (t, 3H), 1.88 (d, 2H), 1.99 (s, 1H), 2.13 (m, 2H), 2.23 (m, 8H), 2.58 (m, 1H), 3.33 (s, 2H), 3.50 (s, 2H), 3.90 (d, 1H), 4.62 (d, 1H), 7.11 (s, 1H), 7.19 (d, 1H), 7.38 (d, 1H), 7.43 (s, 1H), 7.68 (s, 2H), 8.42 (d, 1H).

LRMS: m/z (TSP$^+$) 489.2, 491.2 [MH$^+$]

EXAMPLES 153 TO 156

The following compounds of general formula:

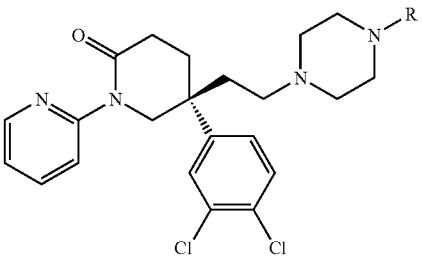

were prepared from the piperazine from example 148 and the appropriate acid chloride, according to the method described in example 152.

| Example | R | Yield (%) | Data |
|---|---|---|---|
| 153 | —C(O)CH$_2$OCH$_3$ | 42 | $^1$Hnmr (CDCl$_3$, 400 MHz) δ: 1.97 (m, 2H), 2.03 (m, 1H), 2.18 (m, 2H), 2.30 (m, 6H), 2.60 (m, 1H), 3.42 (s, 3H), 3.43 (s, 2H), 3.57 (s, 2H), 3.98 (d, 1H), 4.08 (s, 2H), 4.68 (d, 1H), 7.18 (m, 1H), 7.23 (d, 1H), 7.42 (d, 1H), 7.50 (s, 1H), 7.75 (s, 2H), 8.51 (d, 1H). LRMS: m/z (TSP$^+$) 505.1, 507.2 [MH$^+$] |
| 154 | —C(O)OCH(CH$_3$)$_2$ | 33 | $^1$Hnmr (CDCl$_3$, 400 MHz) δ: 1.08 (d, 6H), 1.90–2.35 (m, 11H), 2.55 (s, 1H), 3.33 (m, 4H), 3.86 (d, 1H), 4.60 (d, 1H), 4.82 (m, 1H), 7.08 (m, 1H), 7.20 (d, 1H), 7.38 (d, 1H), 7.41 (s, 1H), 7.63 (s, 2H), 8.41 (s, 1H). LRMS: m/z (TSP$^+$) 519.2, 521.2 [MH$^+$] |
| 155 | —C(O)N(CH$_3$)$_2$ | | $^1$Hnmr (CDCl$_3$, 300 MHz) δ: 1.86–2.10 (m, 3H), 2.10–2.40 (m, 9H), 2.60 (m, 1H), 2.81 (m, 6H), 3.19 (m, 3H), 3.97 (d, 1H), 4.64 (d, 1H), 7.12–7.32 (m, 2H), 7.40 (d, 1H), 7.49 (s, 1H), 7.74 (m, 2H), 8.48 (d, 1H). LRMS: m/z (TSP$^+$) 504.2, 506.2 [MH$^+$] |
| 156 | —C(O)N(CH$_2$CH$_3$)$_2$ | 24 | $^1$Hnmr (CDCl$_3$, 400 MHz) δ: 1.11 (t, 6H), 1.90–2.40 (m, 11 H), 2.60 (m, 1H), 3.19 (m, 8H), 3.97 (d, 1H), 4.68 (d, 1H), 7.18 (m, 1H), 7.22 (m, 1H), 7.41 (d, 1H), 7.50 (s, 1H), 7.73 (d, 2H), 8.51 (d, 1H). LRMS: m/z (TSP$^+$) 532.3, 534.2 [MH$^+$] |

EXAMPLE 157

N'-(1-{2-[(3S)-3-(3,4-Dichlorophenyl)-6-oxo-1-(2-pyridinyl)piperidinyl]ethyl}-4-piperidinyl)-N,N-diethylurea

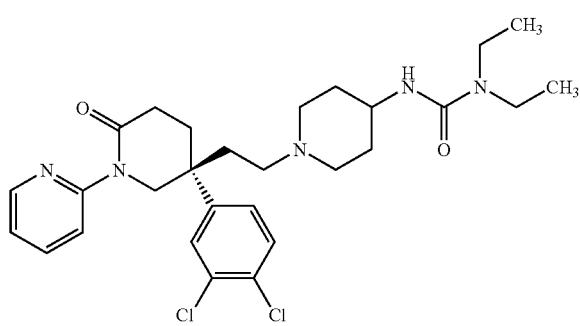

Triethylamine (40 µl, 0.32 mmol) and diethylcarbamoyl chloride (40 µl, 0.30 mmol) were added to a solution of the amine from example 149 (120 mg, 0.27 mmol) in tetrahydrofuran (5 ml), and the reaction stirred at 40° C. for 18 hours. The mixture was concentrated under reduced pressure and the residue purified by column chromatography on silica gel using dichloromethane:methanol:0.88 ammonia (90:10:1) to afford the title compound, 129 mg.

$^1$Hnmr (CDCl$_3$, 400 MHz) δ: 1.11 (t, 6H), 1.27 (m, 2H), 1.96 (m, 6H), 2.14 (m, 2H), 2.30 (m, 2H), 2.58 (m, 1H), 2.68 (d, 2H), 3.22 (q, 4H), 3.62 (m, 1H), 3.92 (d, 1H), 4.06 (d, 1H), 4.61 (d, 1H), 7.14 (dd, 1H), 7.22 (d, 1H), 7.40 (d, 1H), 7.48 (s, 1H), 7.70 (s, 2H), 8.48 (d, 2H).

LRMS: m/z (ES$^+$) 546, 548 [MH$^+$]

EXAMPLE 158

N-(1-{2-[(3S)-3-(3,4-Dichlorophenyl)-6-oxo-1-(2-pyridinyl)piperidinyl]ethyl}-4-piperidinyl)-N-methylacetamide

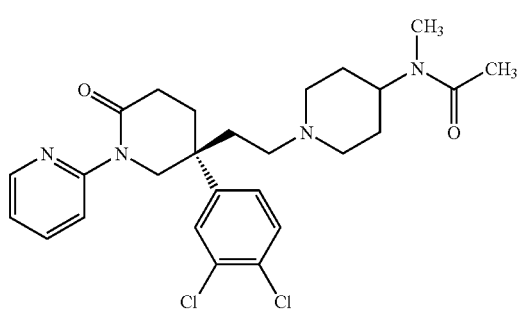

The title compound was obtained as a white foam in 89% yield, from the amine from example 150 and acetyl chloride, following a similar procedure to that described in example 157, except that dichloromethane was used as the reaction solvent.

$^1$Hnmr (CDCl$_3$, 400 MHz) δ: (mixture of rotamers) 1.48 (m, 4H), 1.68 (m, 1H), 1.88 (s, 3H), 1.97 (m, 1H), 2.02 (2×s, 3H), 2.11 (m, 2H), 2.26 (m, 2H), 2.54 (m, 1H), 2.72 (s, 2H), 2.76 (s, 3H), 3.40, 4.36 (2×m, 1H), 3.91 (d, 1H), 4.58 (d, 1H), 7.10 (dd, 1H), 7.19 (d, 1H), 7.37 (d, 1H), 7.44 (s, 1H), 7.67 (s, 2H), 8.44 (s, 1H).

LRMS: m/z (ES$^+$) 503, 505 [MH$^+$]

Microanalysis found: C, 60.66; H, 6.55; N, 10.89. $C_{26}H_{32}Cl_2N_4O_2$; 0.5H$_2$O requires C, 60.94; H, 6.49; N, 10.93%.

EXAMPLE 159

N-(1-{2-[(3S)-3-(3,4-Dichlorophenyl)-6-oxo-1-(2-pyridinyl)piperidinyl]ethyl}-4-piperidinyl)-N',N'-diethyl-N-methylurea

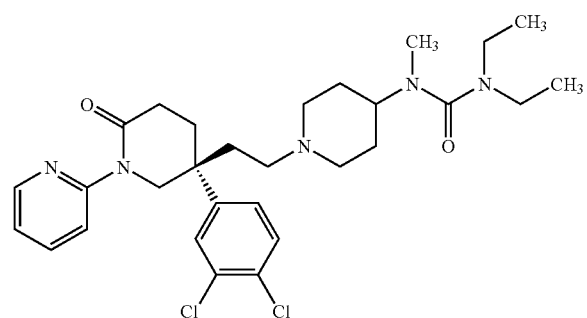

Triethylamine (55 µl, 0.40 mmol) and diethylcarbamoyl chlorde (50 µl, 0.36 mmol) were added to a solution of the amine from example 150 (152 mg, 0.33 mmol) in dichloromethane (5 ml), and the solution stirred at room temperature for 2 hours. Tlc analysis showed starting material remaining, so additional diethylcarbamoyl chloride (50 µl, 0.36 mmol) was added and the reaction stirred at room temperature for 18 hours. The mixture was concentrated under reduced pressure and the residue purified by column chromatography on silica gel using dichloromethane:methanol:0.88 ammonia (90:10:1) as eluant, to afford the title compound as a white foam, 152 mg.

$^1$Hnmr (CDCl$_3$, 400 MHz) δ: 1.09 (t, 6H), 1.63 (m, 4H), 1.93 (m, 5H), 2.12 (m, 2H), 2.30 (m, 2H), 2.58 (m, 1H), 2.66 (s, 3H), 2.80 (m, 2H), 3.12 (q, 4H), 3.54 (m, 1H), 3.92 (d, 1H), 4.62 (d, 1H), 7.13 (dd, 1H), 7.22 (d, 1H), 7.40 (d, 1H), 7.48 (s, 1H), 7.70 (s, 2H), 8.48 (dd, 1H).

LRMS: m/z (ES$^+$) 560, 562 [MH$^+$]

Microanalysis found: C, 61.07; H, 7.04; N, 12.21. $C_{29}H_{39}Cl_2N_5O_2$: 0.15CH$_2$Cl$_2$ requires C, 61.07; H, 6.91; N, 12.22%.

EXAMPLE 160

N-(1-{2-[(3S)-3-(3,4-Dichlorophenyl)-6-oxo-1-(2-pyridinyl)piperidinyl]ethyl}-4-piperidinyl)methanesulfonamide

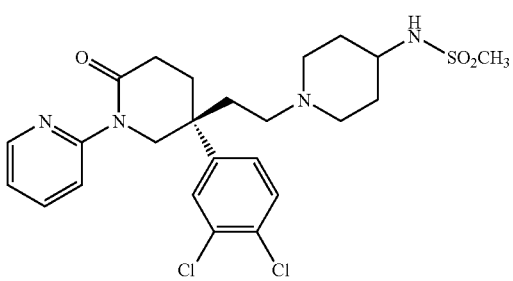

Triethylamine (43 μl, 0.31 mmol) and methanesulphonyl chloride (20 μl, 0.26 mmol) were added to an ice-cooled solution of the amine from example 149 (115 mg, 0.26 mmol) in dichloromethane (5 ml), and the solution stirred at room temperature for an hour. The mixture was washed with water, then brine, dried (MgSO$_4$) and concentrated under reduced pressure. The residue was purified by column chromatography on silica gel using dichloromethane:methanol:0.88 ammonia (90:10:1) to afford the title compound.

$^1$Hnmr (CDCl$_3$, 300 MHz) δ: 1.60 (m, 4H), 1.85–2.44 (m, 11H), 2.63 (m, 1H), 2.80 (m, 1H), 2.99 (s, 3H), 3.32 (m, 1H), 3.97 (d, 1H), 4.65 (d, 1H), 7.17 (m, 1H), 7.23 (d, 1H), 7.44 (d, 1H), 7.51 (s, 1H), 7.73 (m, 2H), 8.50 (d, 1H).

LRMS: m/z (ES$^+$) 525, 527 [MH$^+$]

EXAMPLE 161

N-(1-{2-[(3S)-3-(3,4-Dichlorophenyl)-6-oxo-1-(2-pyridinyl)piperidinyl]ethyl}-4-piperidinyl)benzenesulfonamide

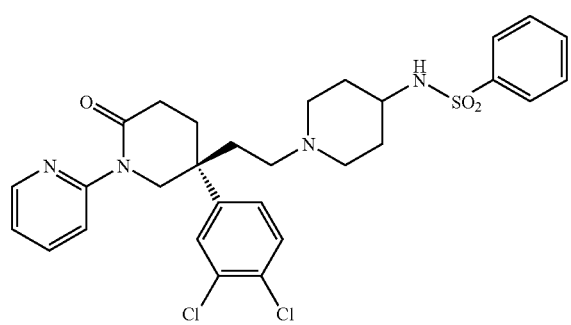

The title compound was obtained, from the amine from example 149 and phenylsulphonyl chloride, following the procedure described in example 160.

$^1$Hnmr (CDCl$_3$, 400 MHz) δ: 1.33 (m, 3H), 1.47–2.17 (m, 8H), 2.18–2.36 (m, 2H), 2.52 (m, 3H), 3.09 (bs, 1H), 3.86 (d, 1H), 4.35 (bs, 1H), 4.60 (d, 1H), 7.10 (m, 1H), 7.18 (d, 1H), 7.28–7.59 (m, 5H), 7.66 (s, 2H), 7.81 (m, 2H), 8.43 (d, 1H).

LRMS: m/z (TSP$^+$) 587.2, 589.2 [MH$^+$]

Microanalysis found: C, 57.25; H, 5.54; N, 8.84. C$_{29}$H$_{32}$Cl$_2$N$_4$O$_3$S; 1.2H$_2$O requires C, 57.18; H, 5.69; N, 9.20%.

EXAMPLE 162

N-(1-{2-[(3S)-3-(3,4-Dichlorophenyl)-6-oxo-1-(2-pyridinyl)piperidinyl]ethyl}-4-piperidinyl)-N-methylmethanesulfonamide

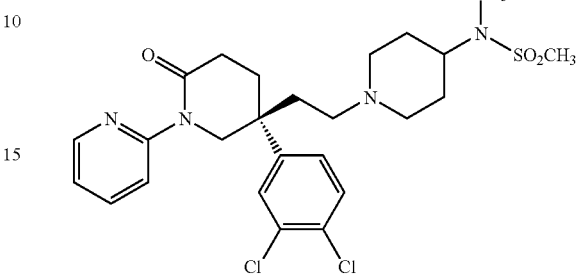

Triethylamine (0.21 ml, 1.51 mmol) followed by methanesulphonyl chloride (0.1 ml, 1.28 mmol) were added to an ice-cooled solution of the amine from example 150 (340 mg, 0.6 mmol) in dichloromethane (10 ml) and the reaction stirred at room temperature for 2 hours. The mixture was washed with water, the aqueous wash extracted with dichloromethane and the combined organic solutions washed with brine, dried (MgSO$_4$) and concentrated under reduced pressure. The residual oil was purified by column chromatography on silica gel using dichloromethane:methanol:0.88 ammonia (95:5:0.5) as eluant to afford the title compound as a white foam, 102 mg.

$^1$Hnmr (CD$_3$Cl, 400 MHz) 67 :1.50 (m, 4H), 1.60 (m, 2H), 1.80–2.18 (m, 6H), 2.28 (m, 2H), 2.58 (m, 1H), 2.72 (m, 4H), 2.78 (s, 3H), 3.61 (m, 1H), 3.95 (d, 1H), 4.59 (d, 1H), 7.10 (m, 1H), 7.20 (m, 1H), 7.39 (m, 1H), 7.42 (s, 1H), 7.69 (m 2H), 8.43 (d, 1H).

LRMS m/z (TSP$^+$) 539.1, 541.2 [MH$^+$]

EXAMPLE 163

N-[1-(1-{2-[(3S)-3-(3,4-Dichlorophenyl)-6-oxo-1-(2-pyridinyl)piperidinyl]ethyl}-3-azetidinyl)-4-piperidinyl]methanesulfonamide

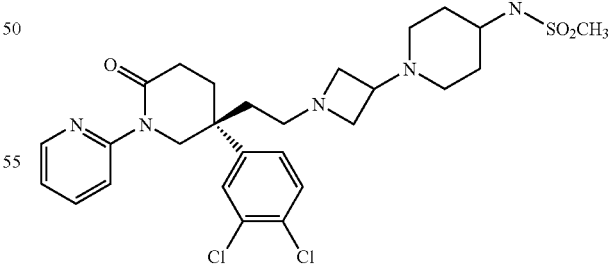

Triethylamine (127 mg, 1.26 mmol) and methanesulphonyl chloride (120 mg, 1.05 mmol) were added to a solution of the amine from example 147 (210 mg, 0.42 mmol) in dichloromethane (100 ml), and the reaction stirred for 20 minutes. The mixture was washed with 0.88 ammonia (20 ml), the layers separated, and the aqueous phase was extracted with dichloromethane (2×100 ml). The combined organic solutions were washed with brine, dried (MgSO$_4$), evaporated under reduced pressure and azeotroped with dichloromethane (4×100 ml), to afford the title compound as a white foam, 210 mg.

$^1$Hnmr (CDCl$_3$, 400 MHz) δ: 1.56 (m, 2H), 1.87–2.04 (m, 5H), 2.08–2.39 (m, 6H), 2.46 (m, 1H), 2.62 (m, 3H), 2.81–3.00 (m, 5H), 3.32 (m, 1H), 3.60 (m, 2H), 3.92 (d, 1H), 4.57 (d, 1H), 4.67 (m, 1H), 7.16 (m, 1H), 7.23 (d, 1H), 7.43 (m, 2H), 7.73 (m, 2H), 8.49 (m, 1H).

LRMS: m/z (ES$^+$) 580, 582 [MH$^+$]

EXAMPLE 164

5-(3,4-Dichlorophenyl)-5-{2-[(2-phenoxyethyl)amino]ethyl}-1-(2-pyridinyl)-2-piperidinone

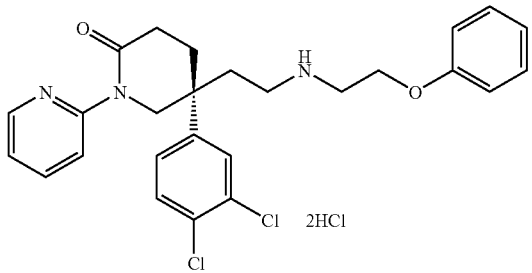

Triethylamine was added to a suspension of 2-phenoxyethylamine in dichloromethane (8 ml) until a solution was obtained, and then sufficient acetic acid was added to achieve a pH of 4. A solution of the aldehyde hydrochloride from preparation 11b (250 mg, 0.63 mmol) in dichloromethane (5 ml) was added followed by sodium triacetoxyborohydride (132 mg, 0.63 mmol), and the reaction stirred for 20 minutes. 4N Sodium hydroxide solution was added, the mixture stirred for 30 minutes, then filtered through a phase separation membrane. The organic filtrate was concentrated under reduced pressure, and the residue purified by column chromatography using dichloromethane:methanol: 0.88 ammonia (95:5:0.5) as eluant. The product was redissolved in dichloromethane, treated with 1N ethereal hydrochloric acid, and the mixture evaporated under reduced pressure to afford the title compound as a white solid, 199 mg.

$^1$Hnmr (CD$_3$OD, 400 MHz) δ: 2.20–2.40 (m, 3H), 2.43–2.60 (m, 2H), 2.73–2.92 (m, 2H), 2.90–3.05 (m, 1H), 3.40 (m, 2H), 4.15–4.27 (m, 3H), 4.46 (d, 1H), 6.88–7.03 (m, 3H), 7.28 (dd, 2H), 7.44 (d, 1H), 7.59 (d, 1H), 7.68–7.75 (m, 2H), 7.93 (d, 1H), 8.43 (dd, 1H), 8.60 (d, 1H).

LRMS: m/z (TSP$^+$) 484.1, 486.1 [MH$^+$]

EXAMPLES 165 TO 167

The following examples of general structure:

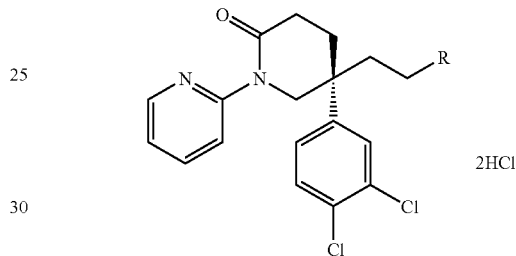

were prepared as white solids, from the aldehyde hydrochloride from preparation 11b and the appropriate amine, according to the procedure described in example 164.

| Example | R | Yield | Data |
|---|---|---|---|
| 165$^a$ | ![NH-CH2CH2-O-(2-fluorophenyl)] | 37 | $^1$Hnmr (CD$_3$OD, 400 MHz) δ: 2.17–2.38 (m, 3H), 2.40–2.57 (m, 2H), 2.70–2.78 (m, 1H), 2.84 (m, 1H), 3.01 (m, 1H), 3.41 (t, 2H), 4.17 (d, 1H), 4.26 (t, 2H), 4.50 (d, 1H), 6.97–7.16 (m, 4H), 7.45 (d, 1H), 7.52–7.60 (m, 2H), 7.73 (d, 1H), 7.80 (d, 1H), 8.20 (dd, 1H), 8.58 (d, 1H). LRMS: m/z (TSP$^+$) 504.2, 506.2 [MH$^+$] |
| 166$^b$ | ![NH-CH2CH2-O-(3-fluorophenyl)] | 39 | $^1$Hnmr (CD$_3$OD, 400 MHz) δ: 2.18–2.42 (m, 3H), 2.42–2.60 (m, 2H), 2.72–2.89 (m, 2H), 2.95 (m, 1H), 3.37 (t, 2H), 4.15–4.36 (m, 3H), 4.43 (d, 1H), 6.60–6.82 (m, 3H), 7.24 (dd, 1H), 7.40 (d, 1H), 7.52 (d, 1H), 7.68 (d, 1H), 7.75 (dd, 1H), 7.99 (d, 1H), 8.50 (dd, 1H), 8.55 (d, 1H). Microanalysis found: C, 50.39; H, 5.26; N, 6.60. C$_{26}$H$_{26}$Cl$_2$FN$_3$O$_2$; 2HCl; 2.5H$_2$O requires C, 49.78; H, 5.30: N, 6.70% |

-continued

| Example | R | Yield | Data |
|---|---|---|---|
| 167[c] | ![NH-CH2CH2-O-C6H4-F structure] | 17 | [1]Hnmr (CD$_3$OD, 400 MHz) δ: 2.21–2.46 (m, 3H), 2.46–2.61 (m, 2H), 2.72–2.90 (m, 2H), 2.99 (m, 1H), 3.39 (t, 2H), 4.12–4.35 (m, 3H), 4.46 (d, 1H), 6.93 (m, 2H), 7.02 (m, 2H), 7.46 (d, 1H), 7.60 (d, 1H), 7.74 (s, 1H), 7.77 (dd, 1H), 8.01 (d, 1H), 8.51 (dd, 1H), 8.60 (d, 1H). Microanalysis found: C, 50.01; H, 5.36; N, 6.89. $C_{26}H_{26}Cl_2FN_3O_2$; 2HCl; 2.5H$_2$O requires C, 49.78; H, 5.30; N, 6.70%. |

Starting amines:
[a]2-(2-fluorophenoxy)ethylamine hydrochloride as prepared in WO 0020401
[b]2-(3-fluorophenoxy)ethylamine hydrochloride from preparation 19
[c]2-(4-fluorophenoxy)ethylamine hydrochloride as prepared in WO 0020401

EXAMPLE 168

5-(3,4-Dichlorophenyl)-1-(6-methyl-2-pyridinyl)-5-{2-[3-(4-oxo-1-piperidinyl)-1-azetidinyl]ethyl}-2-piperidinone

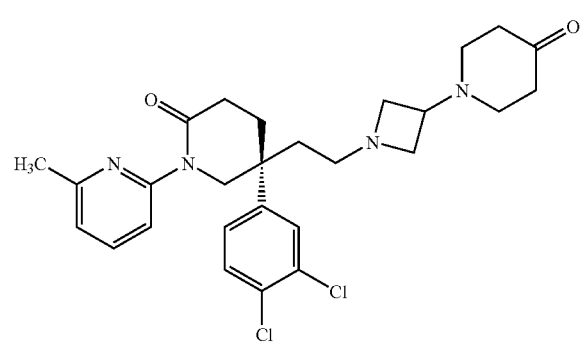

Dess-Martin periodinane (165 mg, 0.39 mmol) was added to a solution of the alcohol from example 132 (200 mg, 0.386 mmol) in dichloromethane (10 ml), and the solution stirred at room temperature for an hour. Tlc analysis showed starting material remaining, so additional Dess-Martin periodinane (82.5 mg, 0.19 mmol) was added and the reaction stirred for a further 30 minutes. Sodium thiosulphate (100 mg), and aqueous sodium bicarbonate solution (10 ml) were added, and the mixture stirred for 10 minutes. The layers were separated, the organic phase dried (Na$_2$SO$_4$) and evaporated under reduced pressure. The residual gum was purified by column chromatography on silica gel using an elution gradient of dichloromethane:methanol:0.88 ammonia (95:5:0.5 to 90:10:1) to afford the title compound as a white foam, 125 mg.

[1]Hnmr (CD$_3$OD, 400 MHz) δ: 1.60–2.60 (m, 25H), 3.95 (d, 1H), 4.50 (d, 1H), 7.00 (d, 1H), 7.24 (d, 1H), 7.44 (d, 2H), 7.60 (m, 2H).

LRMS: m/z (TSP$^+$) 515.1, 517.2 [MH$^+$]

EXAMPLE 169

(5S)-5-(3,4-Dichlorophenyl)-1-(4-methyl-2-pyridinyl)-5-{2-[3-(4-morpholinyl)-1-azetidinyl]ethyl}-2-piperidinone

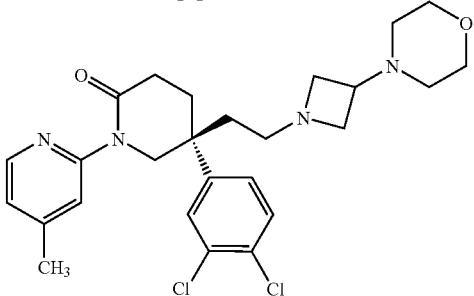

The title compound was prepared as a yellow solid in 32% yield from the aldehyde from preparation 15 and 3-morpholinoazetidine dihydrochloride (WO 9725322), following a similar procedure to that described in example 131.

[1]Hnmr (CDCl$_3$, 400 MHz) 67 : 1.82 (m, 1H), 1.97 (m, 1H), 2.12 (m, 2H), 2.18–2.27 (m, 10H), 2.57 (m, 2H), 2.88–3.10 (m, 3H), 3.63 (m, 5H), 3.88 (d, 1H), 4.42 (d, 1H), 6.96 (d, 1H), 7.20 (m, 1H), 7.40 (m, 2H), 7.48 (s, 1H), 8.30 (d, 1H).

LRMS: m/z (TSP$^+$) 503.2, 504.9 [MH$^+$]

EXAMPLE 170

(5S)-5-(3,4-Dichlorophenyl)-1-(3-methyl-2-pyridinyl)-5-{2-[3-(4-morpholinyl)-1-azetidinyl]ethyl}-2-piperidinone

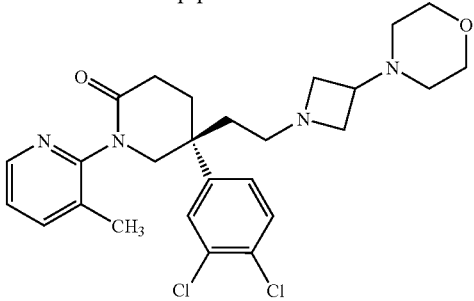

The title compound was prepared as a yellow solid in 8% yield from the aldehyde from preparation 13 and 3-morpholinoazetidine dihydrochloride (WO 9725322), following a similar procedure to that described in example 131.

¹Hnmr (CDCl₃, 400 MHz) δ: 1.72–1.92 (m, 2H), 2.01 (m, 2H), 2.12–2.40 (m, 8H), 2.57 (m, 1H), 2.80 (m, 2H), 2.98 (m, 1H), 3.43 (m, 3H), 3.70 (m, 5.5H), 3.90 (m, 0.5H), 4.22 (m, 0.5H), 4.42 (m, 0.5H), 7.19 (m, 2H), 7.38 (m, 0.5H), 7.44 (m, 1H), 7.58 (m, 1H), 7.80 (m, 0.5H), 8.40 (m, 1H).

LRMS: m/z (TSP⁺) 503.6, 505.7 [MH⁺]

EXAMPLE 171

(5S)-5-(3,4-Dichlorophenyl)-5-[2-(4-phenyl-3,6-dihydro-1(2H)-pyridinyl)ethyl]-1-(2-pyridinyl)-2-piperidinone

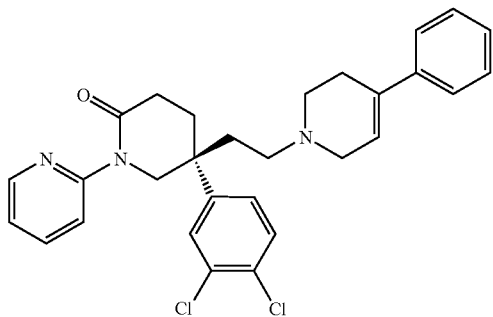

The title compound was prepared in 35% yield as a white foam, from the aldehyde hydrochloride from preparation 11b and 1,2,3,6-tetrahydro-4-phenylpyridine, following a similar procedure to that described in example 17.

¹Hnmr (CDCl₃, 400 MHz) δ: 1.98–2.38 (m, 7H), 2.50 (m, 2H), 2.58 (m, 3H), 3.01 (s, 2H), 3.95 (d, 1H), 4.62 (d, 1H), 5.98 (s, 1H), 7.15 (m, 1H), 7.20–7.38 (m, 7H), 7.40 (d, 1H), 7.52 (s, 1H), 7.72 (d, 2H), 8.47 (d, 1H).

LRMS: m/z (TSP⁺) 506.1, 508.0 [MH⁺]

EXAMPLE 172

(5S)-5-(3,4-Dichlorophenyl)-5-[2-(1,1-dioxido-4-thiomorpholinyl)ethyl]-1-(2-pyridinyl)-2-piperidinone

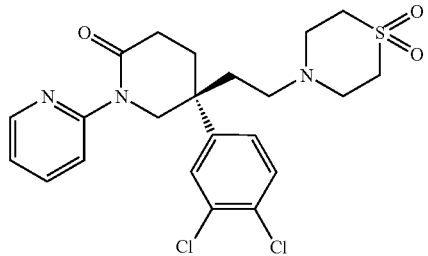

The title compound was prepared in 83% yield as a white foam, from the aldehyde hydrochloride from preparation 11b and thiomorpholine 1,1-dioxide (WO 9605193) following a similar procedure to that described in example 17.

¹Hnmr (CDCl₃, 400 MHz) δ: 1.90 (t, 2H), 2.10–2.38 (m, 5H), 2.58 (m, 1H), 2.78 (m, 2H), 2.86 (m, 2H), 2.99 (m, 4H), 3.88 (d, 1H), 4.90 (d, 1H), 7.18 (m, 2H), 7.41 (d, 1H), 7.45 (s, 1H), 7.72 (dd, 1H), 7.80 (d, 1H), 8.52 (d, 1H).

LRMS: m/z (TSP⁺) 482.1, 484.1 [MH⁺]

Microanalysis found: C, 54.53; H, 5.31; N, 8.50. C₂₂H₂₅Cl₂N₃O₃S requires C, 54.77; H, 5.22; N, 8.71%.

EXAMPLE 173

(5S)-5-(3,4-Dichlorophenyl)-5-[2-(2,6-dimethyl-4-morpholinyl)ethyl]-1-(2-pyridinyl)-2-piperidinone

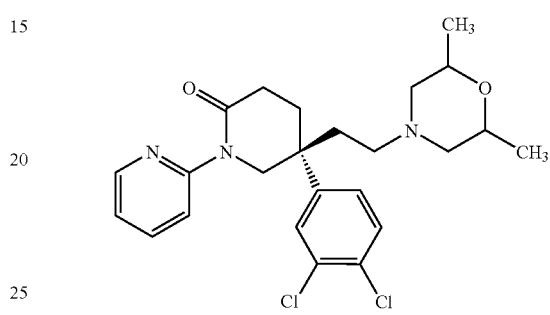

The title compound was prepared in 30% yield as a white foam, from the aldehyde hydrochloride from preparation 11b and 2,6-dimethylmorpholine following a similar procedure to that described in example 17.

¹Hnmr (CDCl₃, 400 MHz) δ: 1.06 (2×d, 6H), 1.55 (m, 2H), 1.92 (m, 3H), 2.02–2.18 (m, 2H), 2.26 (m, 2H), 2.55 (m, 3H), 3.54 (m, 2H), 3.90 (d, 1H), 4.58 (d, 1H), 7.11 (m, 1H), 7.19 (d, 1H), 7.38 (d, 1H), 7.42 (s, 1H), 7.66 (m, 2H), 8.45 (m, 1H).

LRMS: m/z (ES⁺) 462, 464 [MH⁺]

EXAMPLE 174

(5S)-5-{2-[3-(4-Amino-1-piperidinyl)-1-azetidinyl] ethyl}-5-(3,4-dichlorophenyl)-1-(6-methyl-2-pyridinyl)-2-piperidinone tetratrifluoroacetate

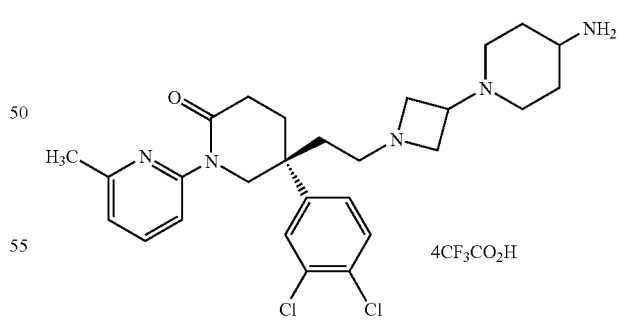

A mixture of the protected amine from preparation 85 (59 mg, 0.1 mmol) and trifluoroacetic acid (0.5 ml) in dichloromethane (3 ml) was stirred at room temperature for 1 hour. The mixture was concentrated under reduced pressure, and the residue azeotroped with toluene (3×) and diethyl ether to afford the title compound as a brown solid, 60 mg.

¹Hnmr (CD₃OD, 400 MHz) δ: 1.74 (m, 2H), 1.99–2.32 (m, 8H), 2.40 (m, 1H), 2.58 (m, 5H), 2.84–3.30 (m, 6H), 3.53 (m, 1H), 3.98 (d, 1H), 4.06 (m, 1H), 4.20 (m, 2H), 4.48 (d, 1H), 7.20 (d, 1H), 7.30 (d, 1H), 7.45 (d, 1H), 7.60 (d, 1H), 7.78 (dd 1H), 7.83 (s, 1H).

Microanalysis found: C, 42.44; H, 4.38; N, 6.48. $C_{27}H_{35}Cl_2N_5O$; $4CF_3CO_2H$;$0.2(C_2H_5)_2O$; $1.5H_2O$ requires C, 42.39; H, 4.37; N, 6.90%.

EXAMPLE 175

5-(3,4-difluorophenyl)-1-(6-methyl-2-pyridinyl)-5-{2-[3-(4-morpholinyl)-1-azetidinyl]ethyl}-2-piperidinone

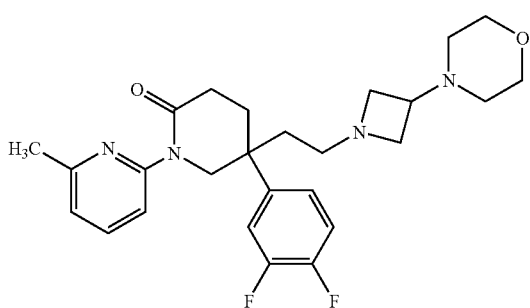

The title compound was prepared as a white foam in 63% yield from the aldehyde from preparation 12c and 3-morpholinoazetidine dihydrochloride (WO 9725322), following a similar procedure to that described in example 112, except dichloromethane:methanol:0.88 ammonia (96:4:0.4) was used as the column eluant.

¹Hnmr (CDCl₃, 400 MHz) δ: 1.50–2.00 (m, 6H), 2.05–2.46 (m, 7H), 2.58 (s, 3H), 2.80 (m, 1H), 2.95 (m, 1H), 3.44 (m, 2H), 3.64 (m, 4H), 3.86 (d, 1H), 4.44 (d, 1H), 6.97(d, 1H), 7.12 (m, 2H), 7.24 (m, 1H), 7.41 (d, 1H), 7.58 (t, 1H).

LRMS: m/z (TSP⁺) 471.3 [MH⁺]

Microanalysis found: C, 65.42; H, 6.90; N, 11.68. $C_{26}H_{32}F_2N_4O_2$; $0.4H_2O$; $0.1\ Et_2O$ requires C, 65.36; H, 7.02; N, 11.55.

EXAMPLE 176

5-(3,4-difluorophenyl)-5-{2-[4-hydroxy-4-phenyl-1-piperidinyl]ethyl}-1-(6-methyl-2-pyridinyl)-2-piperidinone

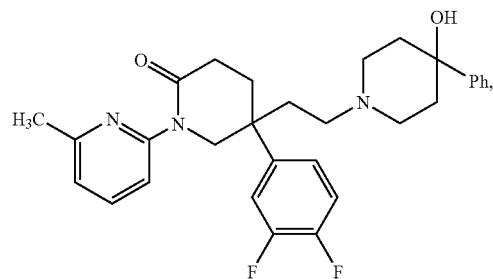

The title compound was prepared as a white solid in 82% yield from the aldehyde from preparation 12c and 4-hydroxy-4-phenylpiperidine, following a similar procedure to that described in example 1, except using a elution gradient of dichloromethane:methanol:0.88 ammonia (97:3:0.3–96:4:0.4).

¹Hnmr (CDCl₃, 400 MHz) δ: 1.55 (m, 3H), 1.72 (m, 2H), 1.90–2.40 (m, 10H), 2.44–2.80 (m, 5H), 3.94 (d, 1H), 4.61 (d, 1H), 6.99 (d, 1H), 7.15 (m, 2H), 7.27 (m, 1H), 7.36 (m, 3H), 7.44 (m, 3H), 7.60 (t, 1H).

LRMS: m/z (TSP⁺) 506.3 [MH⁺]

Microanalysis found: C, 69.78; H, 6.63; N, 8.13. $C_{30}H_{33}F_2N_3O_2$; $0.3H_2O$; $0.1\ CH_2Cl_2$ requires C, 69.59; H, 6.56; N, 8.09.

EXAMPLE 177

5-(3,4-difluorophenyl)-5-{2-[1,4-dioxa-8-azaspiro[4.5]dec-8-yl]ethyl}-1-(6-methyl-2-pyridinyl)-2-piperidinone

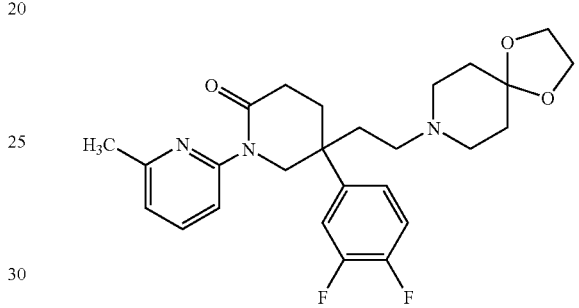

The title compound was prepared as a white foam in 69% yield from the aldehyde from preparation 12c and 1,4-dioxa-8-azaspiro[4.5]decane, following a similar procedure to that described in example 1, except using a elution gradient of dichloromethane:methanol:0.88 ammonia (97:3:0.3–95:5:0.5).

¹Hnmr (CDCl₃, 400 MHz) δ: 1.40–2.80 (m, 19H), 3.92 (m, 5H), 4.60 (m, 1H), 6.96 (d, 1H), 7.12 (m, 2H), 7.24 (m, 1H), 7.40 (d, 1H), 7.57 (t, 1H).

LRMS: m/z (TSP⁺) 472.5 [MH⁺]

Microanalysis found: C, 65.35; H, 6.74; N, 8.70. $C_{26}H_{31}F_2N_3O_3$; $0.4H_2O$; $0.05\ Et_2O$ requires C, 65.23; H, 6.75; N, 8.71.

Preparation 1

(5S)-5-(3,4-Dichlorophenyl)-5-(1,3-dioxolan-2-ylmethyl)-1-(2-pyridinyl)-2-piperidinone

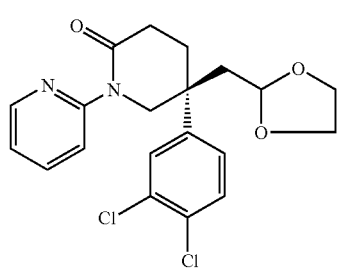

Potassium tert-butoxide (68 g, 0.606 mol) was added to a suspension of (5S)-5-(3,4-dichlorophenyl)-5-(1,3-dioxolan- 2-ylmethyl)-2-piperidinone (WO 9807722) (200 g, 0.606 mol) in 1,2-dimethoxyethane (700 ml), and the mixture heated under reflux for 1 hour. 2-Fluoropyridine (59 g, 0.606 mol) was then added and the mixture stirred under reflux for 1 hour. Additional potassium tert-butoxide (34 g, 0.303 mol) and 2-fluoropyridine (30 g, 0.303 mol) were added and the reaction mixture stirred under reflux for a further hour. The cooled mixture was partitioned with water (500 ml), and the aqueous layer then extracted with ethyl acetate (2×500 ml). The combined organic extracts were dried (MgSO$_4$), and evaporated under reduced pressure. The crude product was purified by column chromatography on silica gel using an elution gradient of ethyl acetate:pentane (20:80 to 100:0) to afford the title compound as a clear gum, 129 g.

$^1$Hnmr (CDCl$_3$, 300 MHz) δ: 1.98 (dd, 1H), 2.16–2.39 (m, 4H), 2.55–2.70 (m, 1H), 3.68 (m, 2H), 3.85 (m, 2H), 3.98 (d, 1H), 4.43 (t, 1H), 4.70 (d, 1H), 7.15 (dd, 1H), 7.29 (dd, 1H), 7.42 (d, 1H), 7.53 (s, 1H), 7.65 (m, 2H), 8.52 (d, 1H).

LRMS: m/z (TSP$^+$) 407.2, 409.5 [MH$^+$]

Preparation 2

(5S)-5-(3,4-Dichlorophenyl)-5-(1,3-dioxolan-2-ylmethyl)-1-(6-methyl-2-pyridinyl)-2-piperidinone

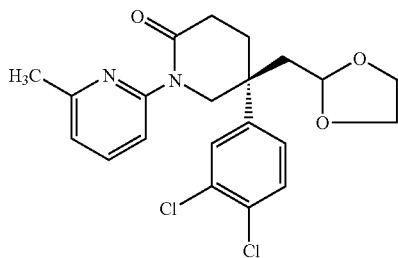

A mixture of (5S)-5-(3,4-dichlorophenyl)-5-(1,3-dioxolan-2-ylmethyl)-2-piperidinone (WO 9807722) (6.5 g, 19.7 mmol), potassium carbonate (3.05 g, 21.7 mmol), copper (I) iodide (400 mg, 2.1 mmol) and 2-bromo-6-methylpyridine (10.2 g, 60 mmol) in 1-methyl-2-pyrrolidinone (200 ml) was stirred at 140° C. for 24 hours. The cooled mixture was partitioned between ethyl acetate and 10% aqueous ammonia, and the layers separated. The aqueous phase was extracted with ethyl acetate, and the combined organic extracts were washed with water, then brine (3×), dried (MgSO$_4$) and evaporated under reduced pressure to give a gum. The crude product was purified by column chromatography on silica gel using an elution gradient of ethyl acetate:pentane (0:100 to 100:0) to afford the title compound as a brown solid, 3.02 g.

$^1$Hnmr (CDCl$_3$, 400 MHz) δ: 2.00 (m, 1H), 2.15–2.38 (m, 4H), 2.58 (m, 4H), 3.69 (m, 2H), 3.85 (m, 2H), 3.95 (d, 1H), 4.45 (t, 1H), 4.62 (d, 1H), 7.00 (d, 1H), 7.26 (m, 1H), 7.40 (dd, 2H), 7.61 (m, 2H).

LRMS: m/z (TSP$^+$) 421.0, 423.0 [MH$^+$]

Preparation 2a 5-(3,4-Difluorophenyl)-5-(1,3-dioxolan-2-yl methyl)-1-(6-methyl-2-pyridinyl)-2-piperidinone

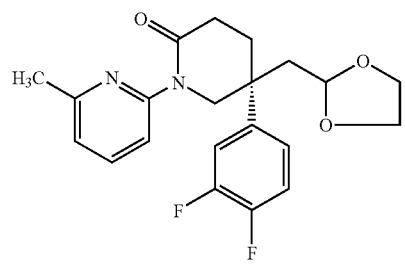

The title compound was obtained as a brown foam in 63% yield from 5-(3,4-difluorophenyl)-5-(1,3-dioxolan-2-ylmethyl)-2-piperidinone (EP 992493) and 2-bromo-6-methylpyridine, following the procedure described in preparation 2.

$^1$Hnmr (CDCl$_3$, 400 MHz) δ: 1.98 (m, 1H), 2.15–2.38 (m, 4H), 2.60 (m, 4H), 3.69 (m, 2H), 3.85 (m, 2H), 3.95 (d, 1H), 4.45 (t, 1H), 4.62 (d, 1H), 7.00 (d, 1H), 7.18 (m, 2H), 7.38 (m, 2H), 7.61 (t, 1H).

LRMS: m/z (TSP$^+$) 389.1 [MH$^+$]

Preparations 3 to 6

The following compounds of the general formula:

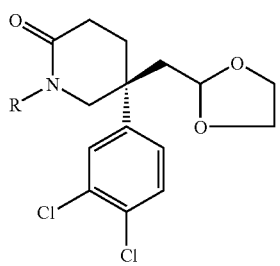

were prepared from (5S)-5-(3,4-dichlorophenyl)-5-(1,3-dioxolan-2-yl methyl)-2-piperidinone (WO 9807722) and the appropriate bromide, according to the procedure described in preparation 2.

| Prep. No. | R | Yield (%) | Data |
|---|---|---|---|
| 3 | 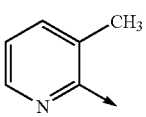 | 17 | ¹Hnmr (CDCl₃, 400 MHz) δ: 1.90–2.35 (m, 9H), 3.62 (m, 2.5H), 3.80 (m, 2H), 4.04 (d, 0.5H), 4.22 (d, 0.5H), 4.36 (t, 1H), 4.50 (d, 0.5H), 7.18 (m, 1.5H), 7.40 (m, 1.5H), 7.55 (m, 1.5H), 7.80 (s, 0.5H), 8.36 (d, 1H). LRMS: m/z (TSP⁺) 421.4, 423.3 [MH⁺] |
| 4 | 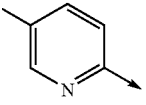 | 28 | ¹Hnmr (CDCl₃, 400 MHz) δ: 1.92 (m, 1H), 2.18–2.38 (m, 7H), 2.56 (m, 1H), 3.64 (m, 2H), 3.84 (m, 2H), 3.92 (dd, 1H), 4.40 (m, 1H), 4.58 (m, 1H), 7.12 (m, 2H), 7.36 (dd, 1H), 7.44 (m, 2H), 8.28 (s, 1H). LRMS : m/z (TSP⁺) 421.1, 423.4 [MH⁺] |
| 5 | 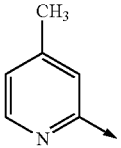 | 19 | ¹Hnmr (CDCl₃, 400 MHz) δ: 1.94 (dd, 1H), 2.22 (m, 4H), 2.36 (s, 3H), 2.58 (m, 1H), 3.62 (m, 2H), 3.84 (m, 2H), 3.94 (d, 1H), 4.40 (t, 1H), 4.60 (d, 1H), 6.95 (d, 1H), 7.22 (dd, 1H), 7.40 (d, 2H), 7.48 (s, 1H), 8.35 (d, 1H). LRMS: m/z (TSP⁺) 421.1, 422.7 [MH⁺] |
| 6 | 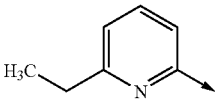 | 16 | ¹Hnmr (CDCl₃, 400 MHz) δ: 1.32 (t, 3H), 1.93 (dd, 1H), 2.20 (m, 4H), 2.56 (m, 1H), 2.80 (q, 2H), 3.68 (m, 2H), 3.82 (m, 3H), 4.41 (t, 1H), 4.80 (d, 1H), 6.96 (d, 1H), 7.30 (d, 1H), 7.38 (m, 2H), 7.58 (dd, 1H), 7.62 (d, 1H). LRMS: m/z (TSP⁺) 435.2, 437.2 [MH⁺] |

Preparation 7

2-Bromo-6-methoxypyridine

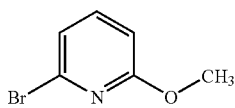

Dried sodium (970 mg, 42.2 mmol) was added portionwise to cooled methanol (50 ml) under nitrogen, and once addition was complete, 2,6-dibromopyridine (10 g, 42.2 mmol) was added portionwise. The resulting suspension was heated under reflux for 24 hours. The cooled reaction was concentrated under reduced pressure, the residue diluted with water (100 ml), and extracted with ethyl acetate (2×75 ml). The organic extracts were dried (MgSO₄), and evaporated under reduced pressure to give a pale yellow oil. The crude product was purified by column chromatography on silica gel using an elution gradient of pentane:ethyl acetate (100:0 to 98:2) to give the title compound as a clear oil, 4.23 g.

¹Hnmr (CDCl₃, 400 MHz) δ: 3.93 (s, 3H), 6.67 (d, 1H), 7.05 (d, 1H), 7.40 (dd, 1H).

Preparation 8

(5S)-5-(3,4-Dichlorophenyl)-5-(1,3-dioxolan-2-ylmethyl)-1-(6-methoxy-2-pyridinyl)-2-piperidinone

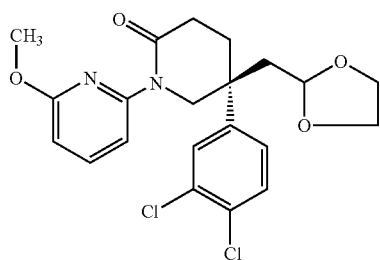

A mixture of (5S)-5-(3,4-d ichlorophenyl)-5-(1,3-d ioxolan-2-yl methyl)-2-piperidinone (WO 9807722) (4.7 g, 14.3 mmol), potassium carbonate (2.97 g, 21.4 mmol), copper (I) iodide (3.0 g, 15.7 mmol) and the bromide from preparation 7 (4.03 g, 21.4 mmol) in 1-methyl-2-pyrrolidinone (25 ml) was stirred at 140° C. for 4 hours, followed by 18 hours at room temperature. The cooled mixture was poured into 2N hydrochloric acid (100 ml), then treated with 0.88 ammonia (100 ml). This aqueous mixture was extracted with ethyl acetate (2×200 ml), the combined organic extracts were washed with water (50 ml), then brine (100 ml), dried (MgSO$_4$) and evaporated under reduced pressure to give an oil. The crude product was purified by column chromatography on silica gel using an elution gradient of dichloromethane:methanol (100:0 to 98:2). The resulting product was dissolved in ether (100 ml), the solution washed with water (5×20 ml), dried (MgSO$_4$) and evaporated under reduced pressure to afford the title compound as a foam, 2.85 g.

$^1$Hnmr (CDCl$_3$, 400 MHz) δ: 1.95 (dd, 1H), 2.18–2.32 (m, 4H), 2.59 (m, 1H), 3.70 (q, 2H), 3.81 (d, 1H), 3.87 (q, 2H), 3.99 (s, 3H), 4.42 (m, 1H), 4.88 (dd, 1H), 6.60 (d, 1H), 7.27 (d, 1H), 7.33 (dd, 1H), 7.41 (d, 1H), 7.61 (dd, 1H), 7.65 (d, 1H).

LRMS: m/z (TSP$^+$) 437.1, 439.1 [MH$^+$]

Preparation 9

(5S)-5-(3,4-Dichlorophenyl)-5-(2,2-dimethoxyethyl)-1-(2-pyridinyl)-2-piperidinone

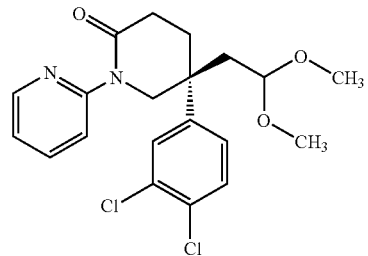

Amberlyst® 15 ion-exchange resin (260 g) was carefully added to a solution of the acetal from preparation 1 (129 g, 0.317 mol) in methanol (800 ml), and the mixture stirred at room temperature for 18 hours. The mixture was filtered, and the resin washed with a methanol:0.88 ammonia solution (10:1, 4×500 ml), and methanol (2×500 ml). The combined filtrate and washings were evaporated under reduced pressure to give a brown solid. The solid was partitioned between dichloromethane (600 ml) and water (300 ml), the layers separated, and the aqueous phase extracted with further dichloromethane (2×100 ml). The combined organic extracts were washed with brine, dried (MgSO$_4$) and evaporated under reduced pressure to give a pale yellow oil. This oil was triturated with ether, and the resulting precipitate was filtered and dried to afford the title compound as a solid, 72 g.

$^1$Hnmr (CDCl$_3$, 400 MHz) δ: 2.04 (t, 2H), 2.15–2.40 (m, 3H), 2.60 (m, 1H), 3.17 (d, 6H), 3.92 (d, 1H), 4.01 (t, 1H), 4.68 (d, 1H), 7.15 (t, 1H), 7.24 (d, 1H), 7.43 (d, 1H), 7.52 (s, 1H), 7.68 (m, 2H), 8.52 (d, 1H).

LRMS: m/z (ES$^+$) 409.0, 411.0 [MH$^+$]

Preparation 10

(5S)-5-(3,4-Dichlorophenyl)-5-(2,2-dimethoxyethyl)-1-(6-methoxy-2-pyridinyl)-2-piperidinone

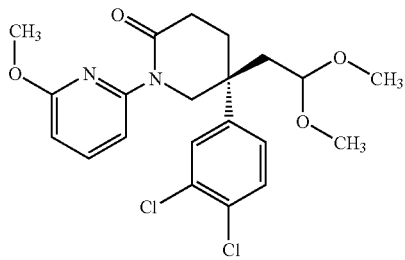

The title compound was obtained as a golden oil (86%) from the acetal of preparation 8, following a similar procedure to that described in preparation 9.

$^1$Hnmr (CDCl$_3$, 400 MHz) δ: 1.95–2.30 (m, 5H), 2.58 (m, 1H), 3.17 (s, 3H), 3.19 (s, 3H), 3.72 (d, 1H), 3.92 (m, 1H), 4.00 (s, 3H), 4.90 (dd, 1H), 6.61 (d, 1H), 7.25 (d, 1H), 7.30 (dd, 1H), 7.42 (d, 1H), 7.61 (dd, 1H), 7.68 (s, 1H).

Preparation 11a

[(3S)-3-(3,4-Dichlorophenyl)-6-oxo-1-(2-pyridinyl)piperidinyl]acetaldehyde

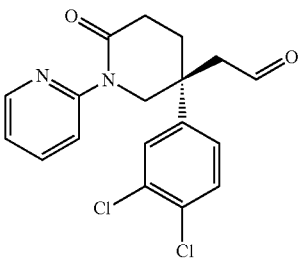

A solution of the acetal from preparation 9 (72 g, 0.176 mol) in tetrahydrofuran (250 ml) was added to an ice-cooled solution of hydrochloric acid (2N, 880 ml), and the solution stirred at room temperature for 18 hours. The mixture was re-cooled in ice, neutralised by the addition of sodium bicarbonate, then basified to pH 9 using 2N sodium hydroxide solution. This aqueous solution was extracted with ethyl acetate (2×1.5L), the combined extracts washed with 2N sodium hydroxide (5×300 ml), dried (MgSO$_4$) and evaporated under reduced pressure to afford the title compound as a pale yellow gum, 47 g.

$^1$Hnmr (CDCl$_3$, 300 MHz) δ: 2.20–2.46 (d, 3H), 2.63 (m, 1H), 2.79 (d, 1H), 2.95 (d, 1H), 4.09 (d, 1H), 4.70 (d, 1H), 7.16 (m, 1H), 7.30 (m, 1H), 7.44 (d, 1H), 7.56 (s, 1H), 7.72 (m, 2H), 8.48 (d, 1H), 9.55 (s, 1H).

Preparation 11b

[(3S)-3-(3,4-Dichlorophenyl)-6-oxo-1-(2-pyridinyl)piperidinyl]acetaldehyde hydrochloride Amberlyst® 15 resin (13 g) was added to a solution of the acetal from preparation 1 (1.34 g, 3.4 mmol) in methanol (50 ml), and the reaction stirred at room temperature for 18 hours. The mixture was filtered, the resin washed with a solution of dichloromethane:methanol:0.88 ammonia (90:10:1), and the combined filtrate evaporated under reduced pressure. The residue was partitioned between diethyl ether and sodium hydroxide solution, the layers separated, and the ether extract was washed with brine, dried (MgSO$_4$) and evaporated under reduced pressure. The residue was dissolved in hydrochloric acid (3N), and the solution stirred at room temperature for 2 hours. The solution was carefully basified using 2N sodium hydroxide solution, and extracted with diethyl ether (3×). The combined organic extracts were dried (MgSO$_4$) and concentrated under reduced pressure. The product was treated with ethereal hydrochloric acid, then evaporated under reduced pressure, to afford the title compound as a white foam, 460 mg.

$^1$Hnmr (CDCl$_3$, 300 MHz) δ: 2.42 (t, 2H), 2.55 (m, 1H), 2.75 (m, 1H), 3.10 (m, 3H), 4.55 (d, 1H), 4.70 (d, 1H), 7.34 (m, 1H), 7.46 (m, 2H), 7.58 (dd, 1H), 7.90 (d, 1H), 8.20 (dd, 1H), 8.64 (d, 1H), 9.58 (s, 1H).

Preparation 12a

[(3S)-3-(3,4-Dichlorophenyl)-6-oxo-1-(6-methyl-2-pyridinyl)piperidinyl]acetaldehyde

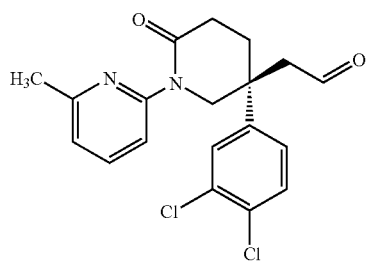

5N Hydrochloric acid (40 ml) was added dropwise to an ice-cooled solution of the acetal from preparation 2 (3.8 g, 9 mmol) in tetrahydrofuran (40 ml), and the reaction stirred at room temperature for 24 hours. The mixture was evaporated, and the residue neutralised by the addition of aqueous sodium bicarbonate solution. The aqueous solution was extracted with ethyl acetate (2×), the combined organic extracts dried (MgSO$_4$), and evaporated under reduced pressure to give the title compound, 2.05 g.

$^1$Hnmr (CDCl$_3$, 300 MHz) δ: 2.24 (m, 1H), 2.38 (m, 2H), 2.56 (s, 3H), 2.58 (m, 1H), 2.88 (dd, 1H), 2.96 (dd, 1H), 4.05 (d, 1H), 4.66 (d, 1H), 7.00 (d, 1H), 7.30 (d, 1H), 7.42 (d, 1H), 7.44 (d, 1H), 7.60 (dd, 1H), 7.65 (d, 1H), 9.56 (s, 1H).

Preparation 12b

[(3S)-3-(3,4-Dichlorophenyl)-6-oxo-1-(6-methyl-2-pyridinyl)piperidinyl]acetaldehyde hydrochloride Amberlyst® 15 resin (320 g) was added to an ice-cooled solution of the acetal from preparation 2 (156 g, 352 mmol) in methanol (1L), and the reaction then stirred at room temperature for 20 hours. The mixture was filtered through Arbocel®, and the resin washed with a (80:20) methanolic ammonia solution (4×1 L) and then dichloromethane (2×1 L), filtering between each wash. The combined filtrates were concentrated under reduced pressure and the residue partitioned between water (1L) and ethyl acetate (2L), and the layers separated. The organic phase was washed with water (2×500 ml), and the combined aqueous solutions extracted with ethyl acetate (500 ml). This organic extract was washed with brine, dried (MgSO$_4$) and evaporated under reduced pressure to give a brown oil, 136 g.

$^1$Hnmr (CDCl$_3$, 300 MHz) δ: 2.02 (m, 2H), 2.15–2.39 (m, 3H), 2.59 (m, 4H), 3.18 (s, 3H), 3.22 (s, 3H), 3.83 (d, 1H), 4.00 (m, 1H), 4.78 (dd, 1H), 7.00 (dd, 1H), 7.30 (dd, 1H), 7.42 (m, 2H), 7.60 (dd, 1H), 7.65 (d, 1H).

A solution of the oil in tetrahydrofuran (280 ml) was added to an ice-cooled solution of 3N hydrochloric acid (530 ml), and the solution stirred at room temperature for 3 hours. The solution was diluted with ethyl acetate (500 ml), and neutralised using sodium bicarbonate. 2N Sodium hydroxide was added to give pH 9, the phases separated, and the organic layer washed with 2N sodium hydroxide (3×100 ml). The combined aqueous washes were extracted with ethyl acetate, then the combined organic solutions washed with brine, dried (MgSO$_4$) and evaporated under reduced pressure. The residual oil was purified by column chromatography on silica gel using ethyl acetate as eluant to give a yellow oil, 94 g. This was dissolved in dichloromethane, and treated with an excess of ethereal hydrochloric acid, and the solution evaporated under reduced pressure. The residue was azeotroped with dichloromethane, to give the title compound as a yellow foam.

$^1$Hnmr (CDCl$_3$, 400 MHz) δ: 2.27–2.52 (m, 3H), 2.66 (m, 1H), 2.94 (s, 3H), 3.17 (s, 2H), 4.38 (d, 1H), 4.68 (d, 1H), 7.22 (d, 1H), 7.44 (m, 4H), 8.15 (dd, 1H), 9.52 (s, 1H).

Preparation 12c

[3-(3,4-difluorophenyl)-6-oxo-1-(6-methyl-2-pyridinyl)piperidinyl]acetaldehyde

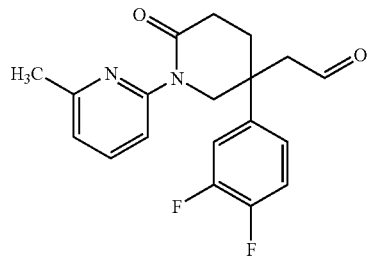

6N Hydrochloric acid (16 ml) was added dropwise to an ice-cooled solution of the acetal from preparation 2a (3.42 g, 9 mmol) in methanol (40 ml), and the reaction stirred at room temperature for 24 hours. The mixture was evaporated, and the residue neutralised by the addition of aqueous sodium bicarbonate solution. The aqueous solution was extracted with ethyl acetate (2×), the combined organic extracts washed with brine, dried (MgSO$_4$) and evaporated under reduced pressure to give a yellow oil, 3.5 g. The crude product was purified by column chromatography on silica gel using dichloromethane:methanol:0.88 ammonia (98:2:0.2) as eluant to give the title compound as a yellow gum, (750 mg).

$^1$Hnmr (CDCl$_3$, 300 MHz) δ: 2.21–2.42 (m, 3H), 2.48–2.64 (m, 4H), 2.78 (dd, 1H), 2.96 (dd, 1H), 4.05 (d, 1H), 4.66 (d, 1H), 7.00 (d, 1H), 7.18 (m, 2H), 7.36 (m, 1H), 7.46 (d, 1H), 7.60 (m, 1H), 9.55 (s, 1H).

LRMS: m/z (TSP$^+$) 345.1 [MH$^+$].

Preparations 13 to 16

The following compounds of the general formula:

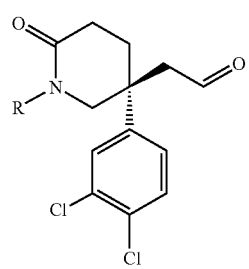

were prepared from the corresponding acetals following the procedure described in preparation 12a.

| Prep. No. | R | Yield (%) | Data |
|---|---|---|---|
| 13 | 3-methyl-2-pyridinyl | 69 | LRMS: m/z (TSP+) 377.2, 378.7 [MH+] |
| 14 | 5-methyl-2-pyridinyl | 78 | LRMS: m/z (TSP+) 377.5, 379.5 [MH+] |
| 15 | 4-methyl-2-pyridinyl | 56 | ¹Hnmr (CDCl₃, 400 MHz) δ: 2.00–2.46 (m, 6H), 2.58 (m, 1H), 2.80 (m, 1H), 3.02 (m, 1H), 4.05 (m, 1H), 4.30 (d, 0.5H), 4.60 (d, 0.5H), 7.20 (m, 1H), 7.41–7.83 (m, 4H), 8.39 (m, 1H), 9.55 (s, 1H). LRMS: m/z (TSP+) 377.2, 378.2 [MH+] |
| 16 | 6-ethyl-2-pyridinyl | 90 | ¹Hnmr (CDCl₃, 400 MHz) δ: 1.30 (t, 3H), 2.20–2.40 (m, 2H), 2.38 (m, 2H), 2.60 (m, 1H), 2.80 (q, 2H), 2.92 (d, 1H), 4.00 (d, 1H), 4.76 (d, 1H), 6.96 (d, 1H), 7.32 (dd, 1H), 7.40 (d, 1H), 7.44 (d, 1H), 7.60 (dd, 1H), 7.74 (d, 1H), 9.54 (s, 1H). LRMS: m/z (TSP+) 391.0, 393.2 [MH+] |

Preparation 17

{(3S)-3-(3,4-Dichlorophenyl)-1-[6-(dimethylamino)-2-pyridinyl]-6-oxopiperidinyl}acetaldehyde hydrochloride

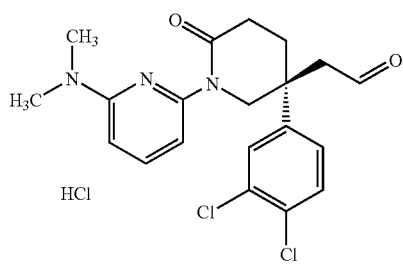

Copper (I) iodide (6.4 g, 33.3 mmol), potassium carbonate (6.3 g, 45.4 mmol) and 6-bromo-2-(dimethylamino)pyridine (WO 9843971) (9 g, 45.4 mmol) were added consecutively to a solution of (5S)-5-(3,4-dichlorophenyl)-5-(1,3-dioxolan-2-ylmethyl)-2-piperidinone (WO 9807722) (10 g, 30.3 mmol), in 1-methyl-2-pyrrolidinone (50 ml), and the mixture was stirred at 140° C. for 4 hours. The cooled mixture was poured into 4N hydrochloric acid, then carefully basified using 10% aqueous ammonia. The aqueous mixture was extracted with ethyl acetate (3×200 ml), and the combined organic extracts were washed with brine, dried (MgSO₄) and evaporated under reduced pressure to give an orange oil. The crude product was purified by column chromatography on silica gel using methanol:dichloromethane (5:95) as eluant, and repeated using ethyl acetate as eluant. The product was treated with 1N ethereal hydrochloric acid, and evaporated under reduced pressure to afford the title compound.

¹Hnmr (CDCl₃, 400 MHz) δ: 2.21–2.43 (m, 2H), 2.55–2.81 (m, 2H), 3.05 (d, 1H), 3.18 (d, 1H), 3.38 (s, 6H), 4.39 (q, 2H), 6.90 (d, 1H), 6.95 (d, 1H), 7.25 (d, 1H), 7.42 (d, 1H), 7.48 (s, 1H), 7.86 (dd, 1H), 9.53 (s, 1H).
LRMS: m/z (TSP+) 406.1, 408.1 [MH+]

Preparation 18

{(3S)-3-(3,4-Dichlorophenyl)-1-[6-methoxy-2-pyridinyl]-6-oxopiperidinyl}acetaldehyde hydrochloride

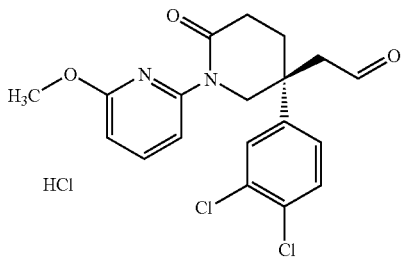

A solution of the acetal from preparation 10 (2.47 g, 5.62 mmol) in tetrahydrofuran (10 ml) was added dropwise to cooled (5° C.) hydrochloric acid (14 ml, 2N, 28 mmol), and the reaction stirred at room temperature for 18 hours. Tlc analysis showed starting material remaining, so additional hydrochloric acid (10 ml, 2N), and tetrahydrofuran (10 ml) were added and the reaction stirred for a further 24 hours at room temperature. The solution was cooled in ice, neutralised by the addition of sodium bicarbonate, and basified by the addition of 1N sodium hydroxide solution (10 ml). The mixture was extracted with ethyl acetate (3×50 ml), and the combined organic extracts washed with brine (2×20 ml), dried (MgSO₄) and concentrated under reduced pressure.

The crude product was purified by column chromatography on silica gel using ethyl acetate:pentane (75:25) as eluant, to afford the title compound as a foam, 760 mg.

¹Hnmr (CDCl₃, 400 MHz) δ: 2.24–2.40 (m, 3H), 2.60 (m, 1H), 2.70–3.00 (ABq, 2H), 3.95 (d, 1H), 3.98 (s, 3H), 4.81 (d, 1H), 6.62 (d, 1H), 7.27 (d, 1H), 7.35 (dd, 1H), 7.45 (d, 1H), 7.63 (dd, 1H), 7.69 (d, 1H), 9.52 (s, 1H).

Preparation 19

2-(3-Fluorophenoxy)ethylamine hydrochloride

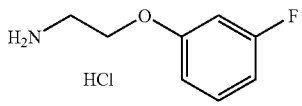

A solution of 3-fluorophenol (20 g, 178 mmol) in tetrahydrofuran (100 ml) and N,N-dimethylformamide (100 ml), was added dropwise to a cooled (10° C.) suspension of sodium hydride (13.38 g, 80% dispersion in mineral oil, 446 mmol) in tetrahydrofuran (200 ml). Once addition was complete, the mixture was stirred at room temperature for 45 minutes. 2-Bromoethylamine hydrobromide (36.56 g, 178 mmol) was added portionwise over 30 minutes, and then the reaction stirred at 45° C. for 18 hours. Water (800 ml) was carefully added to the cooled solution, and the mixture extracted with ethyl acetate (3×250 ml). The organic solutions were extracted with 2M hydrochloric acid (3×200 ml), and these acidic fractions then basified to pH 10 using 2N sodium hydroxide solution. This was re-extracted with ethyl acetate (4×250 ml), these combined organic solutions dried (MgSO₄) and evaporated under reduced pressure. The residual oil was dissolved in ethyl acetate (200 ml), and the solution treated with 1N ethereal hydrochloric acid (150 ml), and the suspension stirred for 2 hours. The resulting precipitate was filtered and dried in vacuo, to afford the title compound as a white solid, 8.0 g.

¹Hnmr (CD₃OD, 400 MHz) δ: 3.35 (s, 2H), 4.20 (s, 2H), 6.65–6.82 (m, 3H), 7.25 (m, 1H).

LRMS: m/z (ES⁺) 156 [MH⁺]

Preparation 20

1-Methyl-2-oxo-1,2-dihydro-4-pyridinecarbonitrile

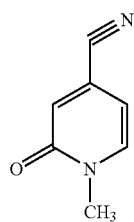

Oxalyl chloride (250 μl, 2.87 mmol) was added to an ice-cooled solution of N,N-dimethylformamide (243 μl, 3.14 mmol) in acetonitrile (3 ml). A suspension of 1-methyl-2-oxo-1,2-dihydro-4-pyridinecarboxamide (J.O.C. 24; 1959; 196) (201.5 mg, 1.32 mmol) and pyridine (470 μl, 5.82 mmol) in acetonitrile (20 ml) was added to the resulting white suspension, and the mixture stirred at room temperature for 18 hours. The mixture was diluted with water (20 ml), and extracted with ethyl acetate (2×100 ml). The combined organic solutions were washed with brine, dried (MgSO₄) and concentrated under reduced pressure. The crude product was purified by column chromatography on silica gel using ethyl acetate:pentane (75:25), then dichloromethane:methanol (90:10) as eluants, to afford the title compound as a pale yellow solid, 112.3 mg.

¹Hnmr (CDCl₃, 300 MHz) δ: 3.40 (s, 3H), 6.27 (d, 1H), 6.93 (s, 1H), 7.41 (d, 1H).

Preparation 21

4-(Aminomethyl)-1-methyl-2(1H)-pyridinone

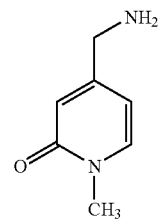

Raney Nickel® (10 mg) was added to a solution of the nitrile from preparation 20 (112.3 mg, 0.84 mmol) and potassium hydroxide (69.7 mg, 1.24 mmol) in ethanol (15 ml) and the mixture hydrogenated at 60 psi for 18 hours. The mixture was filtered through Arbocel®, and washed through with ethanol. The filtrate was evaporated under reduced pressure, and the residue partitioned between water and dichloromethane, and the phases separated. The aqueous layer was evaporated under reduced pressure and the residue triturated with methanol (70 ml). This organic solution was concentrated under reduced pressure and the residue purified by column chromatography on silica gel using dichloromethane:methanol:0.88 ammonia (90:10:1) as eluant to give the title compound as a crystalline solid, 66.3 mg.

¹Hnmr (CDCl₃, 300 MHz) δ: 3.50 (s, 3H), 3.69 (s, 2H), 6.11 (d, 1H), 6.49 (s, 1H), 7.21 (d, 1H).

LRMS: m/z 277.3 [2MH⁺]

Preparation 22

1-Acetyl-4-piperidinamine

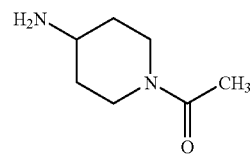

0.88 Ammonia (85 ml) was added to a solution of N-acetylpiperidone (15 g, 106 mmol) in methanol (120 ml), followed by palladium hydroxide (2 g) and the mixture hydrogenated at room temperature and 60 psi for 18 hours. The reaction mixture was filtered through Arbocel®, the filtrate concentrated under reduced pressure and the residue azeotroped with toluene to give a yellow oil. The crude product was purified by column chromatography on silica gel using an elution gradient of dichloromethane:methanol:

0.88 ammonia (96:3.5:0.5 to 84:14:2) to afford the title compound as a clear oil, 9.6 g.

¹Hnmr (CDCl₃, 400 MHz) δ: 1.20 (m, 2H), 1.80 (m, 2H), 2.04 (s, 3H), 2.66 (m, 1H), 2.88 (m, 1H), 3.03 (m, 1H), 3.75 (m, 1H), 4.42 (m, 1H).

LRMS: m/z (ES⁺) 165 [MNa⁺]

Preparation 23 tert-Butyl 3-[(acetylamino)methyl]-1-azetidinecarboxylate

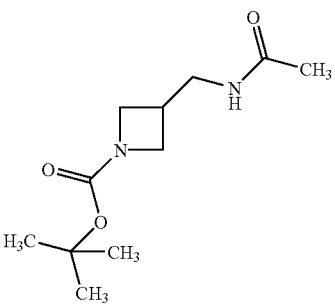

Triethylamine (0.76 ml, 5.45 mmol) and acetic anhydride (0.43 ml, 4.56 mmol) were added to an ice-cooled solution of tert-butyl 3-(aminomethyl)-1-azetidinecarboxylate (J. Med. Chem. 2001; 44(1); 94) (850 mg, 4.56 mmol) in dichloromethane (50 ml), and the reaction stirred for 30 minutes. The solution was washed with water (50 ml), brine (50 ml), dried (MgSO₄) and evaporated under reduced pressure. The crude product was purified by column chromatography on silica gel using ethyl acetate as eluant to afford the title compound as a yellow oil.

¹Hnmr (CDCl₃, 300 MHz) 67 :1.43 (s, 9H), 2.00 (s, 3H), 2.72 (m, 1H), 3.44 (m, 2H), 3.61 (m, 2H), 4.00 (m, 2H), 5.74 (bs, 1H).

LRMS: m/z (ES⁻) 227 (M−H)⁻

Preparation 24 tert-Butyl 3-{[acetyl(methyl)amino]methyl}-1-azetidinecarboxylate

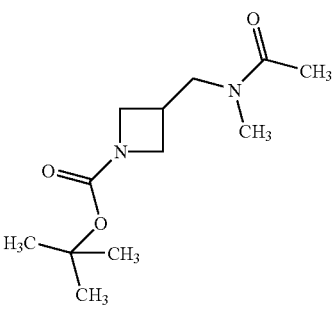

Sodium hydride (154.7 mg, 60% dispersion in mineral oil, 3.87 mmol) was added to a solution of the acetamide from preparation 23 (740 mg, 3.24 mmol) in tetrahydrofuran (20 ml), and the mixture stirred for 45 minutes. Methyl iodide (0.40 ml, 6.42 mmol) was added and the reaction stirred at room temperature for 18 hours. Water (10 ml) was then carefully added, and the tetrahydrofuran removed under reduced pressure. The aqueous solution was extracted with dichloromethane (2×30 ml), the combined organic solutions washed with brine, dried (MgSO₄) and evaporated under reduced pressure to give the title compound as a yellow oil.

¹Hnmr (CDCl₃, 300 MHz) 6 (mixture of rotamers in 8:3 ratio): 1.43 (s, 9H), 2.08, 2.16 (s, 3H), 2.81 (m, 1H), 2.90, 3.02 (s, 3H), 3.50–3.75 (m, 4H), 3.96–4.10 (m, 2H).

LRMS: m/z (ES⁺) 243.2 [MH⁺]

Preparation 25

N-(3-Azetidinyl methyl)-N-methylacetamide

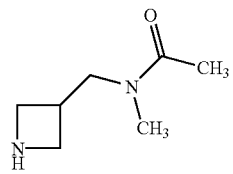

Trifluoroacetic acid (3 ml) was added to an ice-cooled solution of the protected amine from preparation 24 (720 mg, 2.97 mmol) in dichloromethane (20 ml), and the reaction stirred for 3 hours. The solution was diluted with toluene (30 ml), then concentrated under reduced pressure. The residue was purified by column chromatography on silica gel using an elution gradient of dichloromethane:methanol:0.88 ammonia (90:10:1 to 80:20:3), and the product triturated with a solution of ether:ethyl acetate (50:50, 3×30 ml), to give the title compound as a foam.

¹Hnmr (CD₃OD, 300 MHz) δ: 2.10 (s, 3H), 3.08 (s, 3H), 3.21 (m, 1H), 3.64 (d, 2H), 3.95 (m, 2H), 4.09 (m, 2H).

LRMS: m/z (TSP⁺) 285.3 [MH⁺]

Preparation 26

4-Methyl-4piperidinol

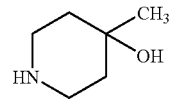

A mixture of 1-benzyl-4-methyl-4-piperidinol (Tet.Lett. 37; 8;1996; 1297) (1.58 g, 7.7 mmol) and palladium hydroxide (500 mg) in ethanol (50 ml) was hydrogenated at 50 psi and 50° C. for 18 hours. The cooled mixture was filtered through Arbocel®, and the filtrate evaporated under reduced pressure to give the title compound as a solid, 880 mg.

¹Hnmr (CDCl₃, 400 MHz) δ: 1.22 (s, 3H), 1.58 (m, 4H), 2.82 (m, 2H), 2.98 (m, 2H).

Preparation 27 tert-Butyl 3-(4-hydroxy-4-methyl-1-piperidinyl)-1-azetidinecarboxylate

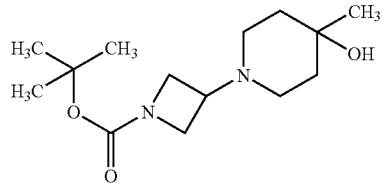

A mixture of the piperidine from preparation 26 (220 mg, 1.91 mmol), tert-butyl 3-iodo-1-azetidinecarboxylate (600 mg, 2.0 mmol) (EP 992493) and potassium carbonate (276 mg, 2.0 mmol) in 1-methyl-2-pyrrolidinone (10 ml) was stirred at 80° C. for 48 hours. The mixture was partitioned between water and ethyl acetate, and the layers separated. The organic phase was washed with water, then brine, dried ($Na_2SO_4$), and evaporated under reduced pressure. The crude product was purified by column chromatography on silica gel using an elution gradient of dichloromethane:methanol:0.88 ammonia (100:0:0 to 90:10:0.5) to afford the title compound, 162 mg.

$^1$Hnmr ($CDCl_3$, 400 MHz) δ: 1.20 (s, 3H), 1.38 (s, 9H), 1.60 (m, 5H), 2.20 (t, 2H), 2.42 (m, 2H), 3.05 (m, 1H), 3.88 (m, 2H), 3.90 (t, 2H).

LRMS: m/z ($TSP^+$) 271.1 [$MH^+$]

Preparation 28

1-(3-Azetidinyl)-4-methyl-4-piperidinol trifluoroacetate

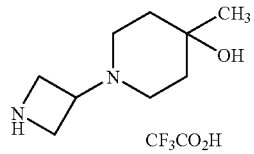

A mixture of the protected azetidine from preparation 27 (160 mg, 0.6 mmol) in trifluoroacetic acid (1 ml) and dichloromethane (1 ml), was stirred at room temperature for 2 hours. The solution was concentrated under reduced pressure and azeotroped with toluene, to afford the title compound as a yellow gum, 155 mg.

$^1$Hnmr ($CDCl_3$, 400 MHz) δ: 1.25 (s, 3H), 1.76 (d, 2H), 1.90 (m, 2H), 3.16 (t, 2H), 3.25 (m, 3H), 4.35 (m, 4H), 4.50 (m, 2H).

LRMS: m/z ($ES^+$) 172 [$MH^+$]

Preparation 29

1-Benzhydryl-3-(2-methoxyphenyl)-3-azetidinol

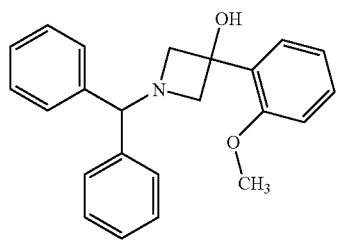

2-Methoxyphenylmagnesium bromide (5.9 ml, 1M solution in tetrahydrofuran, 5.9 mmol) was added to a cooled (−78° C.) solution of 1-benzhydryl-azetidin-3-one (WO 9412181) (1 g, 4.2 mmol) in tetrahydrofuran (20 ml), and the reaction stirred at −78° C. for 15 minutes, then allowed to warm to room temperature over 30 minutes. The mixture was partitioned between water (100 ml) and ethyl acetate (100 ml), the layers separated, and the aqueus phase extracted with ethyl acetate (100 ml). The combined organic solutions were washed with brine (100 ml), dried ($MgSO_4$) and evaporated under reduced pressure. The residual yellow oil was purified by column chromatography on silica gel using pentane:ethyl acetate (50:50) as eluant to afford the title compound as a white foam.

$^1$Hnmr ($CDCl_3$, 400 MHz) δ: 3.58 (m, 4H), 3.95 (s, 3H), 4.42 (s, 1H), 6.94 (d, 1H), 7.00 (dd, 1H), 7.20 (m, 2H), 7.28 (m, 6H), 7.46 (m, 4H).

LRMS: m/z ($TSP^+$) 346.1 [$MH^+$]

Preparation 30

3-(2-Methoxyphenyl)-3-azetidinol hydrochloride

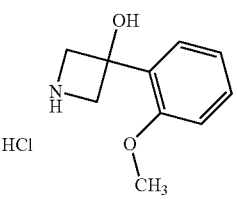

A mixture of palladium hydroxide (1 g, 7.14 mmol), and the azetidine from preparation 29 (950 mg, 2.75 mmol) in methanol (100 ml) was hydrogenated at 50° C. and 50 psi for 18 hours. The cooled reaction mixture was filtered through Arbocel®, and 1N ethereal hydrochloric acid was added to the filtrate. The filtrate was evaporated under reduced pressure, azeotroped with dichloromethane, and the product triturated with diethyl ether, to afford the title compound as a white solid.

$^1$Hnmr ($CD_3OD$, 400 MHz) δ: 3.95 (s, 3H), 4.15 (d, 2H), 4.62 (d, 2H), 6.99 (dd, 1H), 7.07 (d, 1H), 7.30 (d, 1H), 7.38 (dd, 1H).

LRMS: m/z ($TSP^+$) 180.1 [$MH^+$]

Preparation 31

3-Tetrahydro-2H-pyran-4-yl-azetidine p-toluenesulfinate

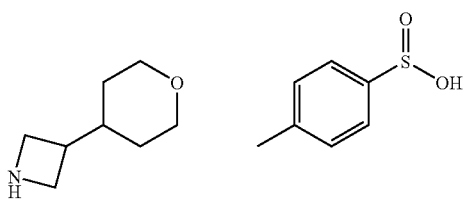

Sodium (390 mg, 16.6 mmol) was added to a solution of naphthalene (2.61 g, 20.4 mmol) in 1,2-dimethoxyethane (25 ml), and the solution stirred at room temperature for 4 hours. This solution was then added dropwise to a cooled (−70° C.) solution of 4-methylphenyl 3-tetrahydro-2H-pyran-4-yl-1-azetidinesulfonate (EP 962457) (1 g, 3.39 mmol) in 1,2-dimethoxyethane (25 ml), and once the addition was complete, the mixture was stirred at −70° C. for 20 minutes. The reaction was allowed to warm to room temperature, the reaction quenched by the addition of water and concentrated under reduced pressure. The residual gum was purified by column chromatography on silica gel using dichloromethane:methanol:0.88 ammonia (80:20:3) as eluant to give the title compound as an off-white gum, 690 mg.

$^1$Hnmr (CD$_3$OD, 400 MHz) δ: 1.18 (m, 2H), 1.58 (m, 2H), 1.81 (m, 1H), 2.38 (s, 3H), 2.68 (m, 1H), 3.40 (t, 2H), 3.90 (m, 4H), 4.04 (t, 2H), 7.22 (d, 2H), 7.55, 7.72 (d, 2H).

Preparation 32

N-(4-Phenyl-4-piperidinyl)acetamide

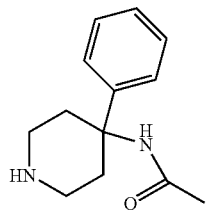

A mixture of N-(1-Benzyl-4-phenyl-4-piperidinyl)acetamide (Bioorg. Med. Chem. Lett. 1996; 6(19); 2307) (49 g, 158 mmol), and palladium hydroxide (5 g) in methanol (600 ml) was hydrogenated at 50 psi and room temperature for 18 hours. The mixture was filtered, the filtrate concentrated under reduced pressure and the residue azeotroped with dichloromethane to give the title compound as a foam.

$^1$Hnmr (CDCl$_3$, 300 MHz) δ: 2.00 (m, 5H), 2.38 (m, 2H), 2.97 (m, 4H), 7.19–7.40 (m, 5H).

Preparation 33

N-[1-(1-Benzhydryl-3-azetidinyl)-4-phenyl-4-piperidinyl]acetamide

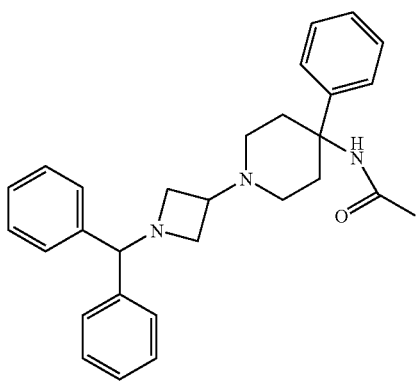

A mixture of 1-(diphenylmethyl)-3-azetidinylmethanesulfonate (8 g, 25.2 mmol), the amine from preparation 32 (7.1 g, 27.7 mmol) and triethylamine (4.6 ml, 32.8 mmol) in acetonitrile (80 ml) was heated under reflux for 18 hours. The cooled mixture was concentrated under reduced pressure, the residue partitioned between sodium bicarbonate solution and ethyl acetate, and the layers separated. The organic phase was washed with water, then brine, dried (MgSO$_4$) and evaporated under reduced pressure. The residual foam was purified by column chromatography on silica gel using an elution gradient (hexane:ethyl acetate:methanol 80:20:0 to 0:100:0 to 0:93:7) to afford the title compound as a white solid, 2.31 g.

$^1$Hnmr (CDCl$_3$, 300 MHz) δ: 2.00 (s, 3H), 2.01–2.20 (m, 4H), 2.37 (m, 2H), 2.62 (m, 2H), 2.84–3.06 (m, 3H), 3.41 (t, 2H), 4.41 (s, 1H), 5.44 (s, 1H), 7.12–7.54 (m, 15H).

Preparation 34

N-[1-(3-Azetidinyl)-4-phenyl-4-piperidinyl]acetamide dihydrochloride

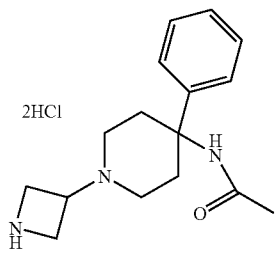

α-Chloroethylchoroformate (630 μl, 8.63 mmol) was added dropwise to an ice-cooled solution of the azetidine from preparation 33 (2.3 g, 5.23 mmol) in dichloromethane (25 ml), and the solution stirred at room temperature for 18 hours. The mixture was concentrated under reduced pressure the residue suspended in methanol (37 ml), potassium carbonate (2.2 g, 15.7 mmol) added, and the mixture heated under reflux for an hour. The cooled mixture was filtered, the filtrate acidifed to pH 3 using ethereal hydrochloric acid, then re-filtered. The filtrate was concentrated under reduced pressure, the residual gum triturated with diethyl ether, to give the title compound as a pale brown solid, 1.5 g.

$^1$Hnmr (DMSOd$_6$, 300 MHz) 67 :1.92 (s, 2H), 2.30 (m, 1H), 2.48 (s, 3H), 2.63 (m, 1H), 3.10 (m, 1H), 4.08 (m, 7H), 4.50 (m, 2H), 7.12–7.65 (m, 5H), 8.30 (s, 1H), 9.15 (bs, 1H), 10.10 (bs, 1H).

LRMS: m/z (TSP$^+$) 274.3 [MH$^+$]

Preparation 35

Ethyl 4-cyanotetrahydro-2H-pyran-4-carboxylate

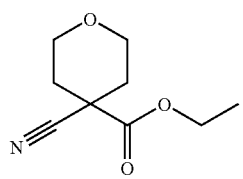

Ethyl cyanoacetate (22.6 g, 0.2 mol) and bis(2-chloroethyl)ether (14 g, 0.1 mol) were added to a suspension of potassium carbonate (70 g, 0.5 mol) in N,N-dimethylformamide (150 ml), and the mixture stirred at 100° C. for 72 hours. The cooled mixture was partitioned between water and diethyl ether (500 ml), the layers separated and the aqueous solution extracted with diethyl ether (3×200 ml). The combined organic solutions were washed with 2N hydrochloric acid (3×100 ml), brine (2×100 ml), dried (MgSO$_4$) and evaporated under reduced pressure to give a yellow oil. This crude product was purified by column chromatography on silica gel using ethyl acetate:cyclohexane (50:50) as eluant, to afford the title compound, 9.3 g.

$^1$Hnmr (CDCl$_3$, 400 MHz) δ: 1.34 (t, 3H), 2.00 (m, 2H), 2.14 (m, 2H), 3.74 (m, 2H), 3.98 (m, 2H), 4.26 (q, 2H).

Preparation 36

[4-({[(4-Methylphenyl)sulfonyl]amino}methyl)tetrahydro-2H-pyran-4-yl]methyl 4-methylbenzenesulfonate

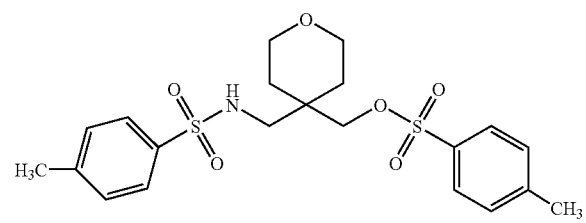

A solution of the ester from preparation 35 (9.3 g, 51 mmol) in tetrahydrofuran (50 ml) was added dropwise to a suspension of lithium aluminium hydride (10 g, 263 mmol) in tetrahydrofuran (200 ml), and once addition was complete, the mixture was heated under reflux for an hour. The mixture was cooled in ice, and water (15 ml) in tetrahydrofuran (50 ml) was added dropwise. Additional tetrahydrofuran (200 ml) was added, the mixture poured into a suspension of MgSO$_4$ (200 g) in tetrahydrofuran (300 ml), and the resulting slurry filtered. The solids were washed well with tetrahydrofuran, and the combined filtrates evaporated under reduced pressure. The residual gum was dissolved in 1,2-dimethoxyethane (200 ml), and triethylamine (20 ml), p-toluenesulfonyl chloride (29 g, 153 mmol) and pyridine (21 ml) added, and the reaction heated under reflux for 18 hours. The cooled mixture was partitioned between dichloromethane (300 ml) and 2N hydrochloric acid (300 ml), the layers separated, and the aqueous phase extracted with dichloromethane (5×300 ml). The combined organic extracts were washed with brine, dried (MgSO$_4$) and the mixture filtered through a plug of silica gel. The filtrate was discarded, the silica washed well with ethyl acetate, and this filtrate concentrated under reduced pressure. The residue was triturated with diethyl ether, to afford the title compound as a beige solid, 6.0 g.

$^1$Hnmr (CDCl$_3$, 300 MHz) δ: 1.43 (m, 1H), 1.55 (m, 3H), 2.46 (2×s, 6H), 3.00 (d, 2H), 3.60 (m, 4H), 3.88 (s, 2H), 4.88 (t, 1H), 7.37 (2×d, 4H), 7.77 (2×d, 4H).

LRMS: m/z (ES$^+$) 454 [MH$^+$]

Preparation 37

2-[(4-Methylphenyl)sulfonyl]-7-oxa-2-azaspiro[3.5]nonane

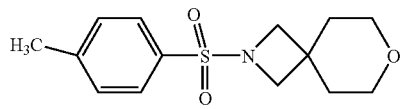

Potassium tert-butoxide (2.0 g, 18 mmol) was added to a suspension of the compound from preparation 36 (5.5 g, 12 mmol) in 1,2-dimethoxyethane (300 ml), and the reaction stirred at 100° C. for 30 minutes. The cooled mixture was concentrated under reduced pressure and the residue partitioned between dichloromethane and 2N sodium hydroxide solution, and the layers separated. The aqueous phase was extracted with further dichloromethane (2×250 ml), and the combined organic solutions washed with brine, dried (MgSO$_4$) and evaporated under reduced pressure to give the title compound as a white solid, 3.3 g.

$^1$Hnmr (CDCl$_3$, 300 MHz) 67 :1.57 (m, 4H), 2.48 (s, 3H), 3.51 (m, 8H), 7.39 (d, 2H), 7.75 (d, 2H).

LRMS: m/z (ES$^+$) 282 [MH$^+$]

Preparation 38

7-Oxa-2-azaspiro[3.5]nonane p-toluenesulphinate

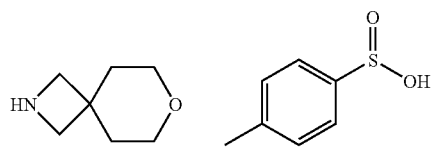

Freshly cut sodium (2.3 g, 100 mmol) was added to a solution of napthalene (15.4 g, 120 mmol) in 1,2-dimethoxyethane (100 ml), and the mixture stirred at room temperature for 3 hours.

The compound from preparation 37 (6.0 g, 21 mmol) was dissolved in 1,2-dimethoxyethane (100 m!), and the solution cooled to −70° C. The prepared solution of sodium naphtalenide was then added, the solution stirred for 10 minutes, and then quenched by the addition of water (5 ml). The solution was allowed to warm to room temperature, potassium carbonate (200 g) and additional 1,2-dimethoxyethane (500 ml) added, and the mixture filtered and evaporated under reduced pressure. The crude product was purified by column chromatography on silica gel using dichloromethane:methanol:0.88 ammonia (80:20:5) as eluant, and the product azeotroped with toluene (5×100 ml) to give a gum. This was triturated with ether to afford the title compound as a white solid, 4.1 g.

$^1$Hnmr (CDCl$_3$, 300 MHz) 67 :1.65 (m, 4H), 2.38 (s, 3H), 3.44 (m, 4H), 3.52 (s, 4H), 7.22 (d, 2H), 7.56 (d, 2H).

Preparation 39 tert-Butyl (3R)-3-(acetylamino)-1-pyrrolidinecarboxylate

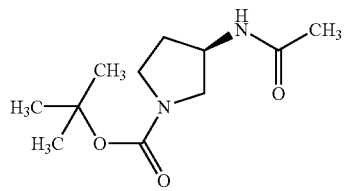

Di-tert-butyl dicarbonate (1.92 g, 8.8 mmol) was added to a solution of N-[(3R)-pyrrolidinyl]acetamide (1 g, 8 mmol) in dichloromethane (30 ml), and the solution cooled in ice. Hünig's base (1.5 ml, 8.8 mmol) was added dropwise, and once addition was complete the reaction was stirred for 2 hours. The mixture was washed with sodium bicarbonate solution (3×), then brine (3×), dried (MgSO$_4$) and evaporated under reduced pressure to give the title compound, 1.75 g.

$^1$Hnmr (CDCl$_3$, 300 MHz) δ: 1.46 (s, 9H), 1.96 (s, 3H), 2.16 (m, 2H), 3.18 (m, 1H), 3.40 (m, 2H), 3.60 (m, 1H), 4.42 (m, 1H), 5.70 (bs, 1H).

Preparation 40 tert-Butyl (3S)-3-(acetylamino)-1-pyrrolidinecarboxylate

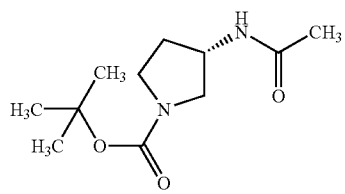

The title compound was obtained as a colourless gum, from N-[(3S)-pyrrolidinyl]acetamide, following the procedure described in preparation.

$^1$Hnmr (CDCl$_3$, 300 MHz) δ: 1.46 (s, 9H), 1.96 (s, 3H), 2.10 (m, 2H), 3.16 (m, 1H), 3.38 (m, 2H), 3.58 (m, 1H), 4.42 (m, 1H), 5.52 (bs, 1H).

Preparation 41 tert-Butyl (3R)-3-[acetyl(methyl)amino]-1-pyrrolidinecarboxylate

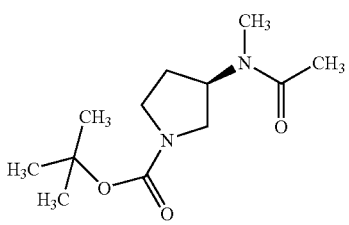

A solution of the pyrrolidine from preparation 39 (1.75 g, 7.7 mmol) in N,N-dimethylformamide (5 ml), was added dropwise to a mixture of sodium hydride (470 mg, 11.7 mmol) in N,N-dimethylformamide (10 ml), and the solution stirred for 30 minutes. Iodomethane (0.8 ml, 8.4 mmol) was added, and the reaction stirred at room temperature for 2 hours. Aqueous ammonium chloride solution was added and the mixture extracted with ethyl acetate. The combined organic solutions were washed with water, brine, then dried (MgSO$_4$) and evaporated under reduced pressure to give the title compound as a yellow gum, 725 mg.

$^1$Hnmr (CDCl$_3$, 300 MHz) δ: 1.44 (s, 9H), 1.90–2.16 (m, 5H), 2.95 (s, 3H), 3.12 (m, 1H), 3.30 (m, 1H), 3.50 (m, 2H), 4.38, 5.20 (2×m, 1H).

LRMS: m/z (TSP$^+$) 243.2 [MH$^+$]

Preparation 42 tert-Butyl (3S)-3-[acetyl(methyl)amino]-1-pyrrolidinecarboxylate

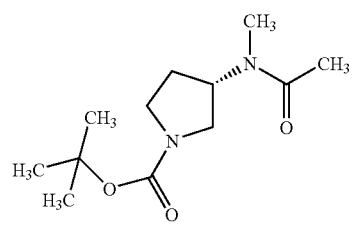

The title compound was obtained as a yellow gum in 44% yield, from the pyrrolidine from preparation 40, following the procedure described in preparation 41.

$^1$Hnmr (CDCl$_3$, 300 MHz) δ: 1.42 (s, 9H), 1.82–2.15 (m, 5H), 2.84 (s, 3H), 3.14 (m, 1H), 3.25 (m, 1H), 3.54 (m, 2H), 4.38, 5.18 (2×m, 1H).

LRMS: m/z (TSP$^+$) 243.2 [MH$^+$]

Preparation 43

N-Methyl-N-[(3R)-pyrrolidinyl]acetamide Trifluoroacetate

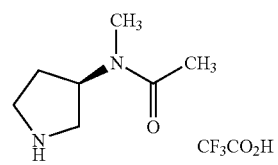

A mixture of the protected pyrrolidine from preparation 41 (720 mg, 2.96 mmol) and trifluoroacetic acid (4 ml) in dichloromethane (4 ml) was stirred at room temperature for 1 hour. The mixture was concentrated under reduced pressure, the residue azeotroped with toluene (3×), dichloromethane (3×) and diethyl ether (3×) to afford the title compound as a gum.

$^1$Hnmr (CD$_3$OD, 400 MHz) δ: 2.10 (s, 3H), 2.16 (m, 1H), 2.38 (m, 1H), 3.06 (s, 3H), 3.20 (m, 1H), 3.40 (m, 2H), 3.60 (m, 1H), 4.50 (m, 1H).

LRMS: m/z (TSP$^+$) 285.2 [MH$^+$]

Preparation 44

N-Methyl-N-[(3S)-pyrrolidinyl]acetamide trifluoroacetate

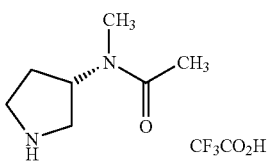

The title compound was obtained as a gum, from the protected pyrrolidine from preparation 42, following the procedure described in preparation 43.

$^1$Hnmr (CD$_3$OD, 400 MHz) δ: 2.08 (s, 3H), 2.18 (m, 1H), 2.38 (m, 1H), 3.06 (s, 3H), 3.20 (m, 1H), 3.40 (m, 2H), 3.60 (m, 1H), 4.50 (m, 1H).
LRMS: m/z (TSP$^+$) 285.2 [MH$^+$]

Preparation 45 tert-Butyl (3R)-3-methoxy-1-pyrrolidinecarboxylate

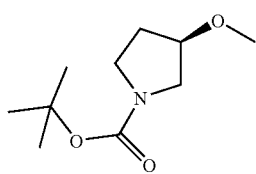

Sodium hydride (2.2 g, 80% dispersion in mineral oil, 73.2 mmol) was added to an ice-cooled solution of (3R)-N-tert-butoxycarbonylpyrrolidin-3-ol (J. Med. Chem. 41; 25; 1998; 4983) (12.5 g, 66.7 mmol) in tetrahydrofuran (330 ml), and the solution stirred at room temperature for an hour. Methyl iodide (14.5 g, 100 mmol) was then added and the reaction stiired for 18 hours. Water (100 ml) was added and the mixture concentrated under reduced pressure to remove the organic solvents. The aqueous was extracted with ethyl acetate, the combined organic solutions dried (MgSO$_4$) and evaporated under reduced pressure to give the title compound as an oil, 12.48 g.

$^1$Hnmr (CDCl$_3$, 400 MHz) δ: 1.42 (s, 9H), 1.86–2.01 (m, 2H), 3.32 (s, 3H), 3.40 (m, 4H), 3.93 (m, 1H).
Microanalysis found: C, 59.71; H, 9.63; N, 6.71. C$_{10}$H$_{19}$NO$_3$ requires C, 59.68; H, 9.52; N, 6.96%.

Preparation 46 tert-Butyl (3S)-3-methoxy-1-pyrrolidinecarboxylate

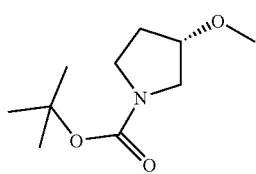

The title compound was prepared from (3S)-N-tert-butoxycarbonylpyrrolidin-3-ol (U.S. Pat. No. 6,180,627), following the procedure described in preparation 45.

$^1$Hnmr (CDCl$_3$, 400 MHz) δ: 1.42 (s, 9H), 1.84–2.00 (m, 2H), 3.32 (s, 3H), 3.40 (m, 4H), 3.92 (m, 1H).
Microanalysis found: C, 59.72; H, 9.62; N, 6.63. C$_{10}$H$_{19}$NO$_3$ requires C, 59.68; H, 9.52; N, 6.96%.

Preparation 47

(3R)-3-Methoxypyrrolidine trifluoroacetate

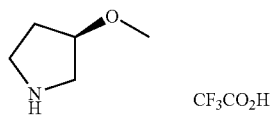

Hydrogen chloride was bubbled through a solution of the protected amine from preparation 45 (24.8 g, 123 mmol) in diethyl ether (615 ml), until saturated, and the solution then stirred for 1 hour at room temperature. The reaction was concentrated under reduced pressure, the residue resuspended in diethyl ether, the solution stirred for 2 hours the ether decanted off, and the residue evaporated under reduced pressure. The product was dissolved in ethanol, trifluoroacetic acid (200 ml) added, and the solution evaporated under reduced pressure to afford the title compound.

$^1$Hnmr (CDCl$_3$, 400 MHz) δ: 2.00 (m, 1H), 2.18 (m, 1H), 3.24–3.50 (m, 7H), 4.05 (m, 1H), 8.80 (bs, 1H), 9.37 (bs, 1H).
Microanalysis found: C, 33.76; H, 5.35; N, 5.54. C$_5$H$_{11}$NO.1.25CF$_3$CO$_2$H; 1.25H$_2$O requires C, 33.84; H, 5.59; N, 5.26%.

Preparation 48

(3S)-3-Methoxypyrrolidine trifluoroacetate

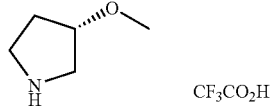

The title compound was obtained, from the protected amine from preparation 46, following the procedure described in preparation 47.

$^1$Hnmr (CDCl$_3$, 400 MHz) δ: 2.00 (m, 1H), 2.18 (m, 1H), 3.25–3.48 (m, 7H), 4.06 (m, 1H), 8.75 (bs, 1H), 9.24 (bs, 1H).

Preparation 49

N-[(3S)-1-Benzyl pyrrolidinyl]-4-chlorobutanamide

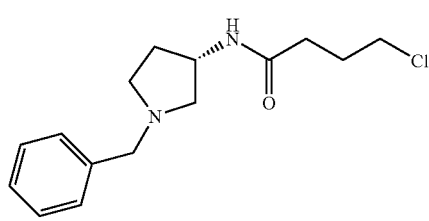

4-Chlorobutyryl chloride (0.31 ml, 3.1 mmol) was added to a mixture of (3S)-1-benzyl-3-pyrrolidinamine (500 mg, 2.8 mmol) in tetrahydrofuran (30 ml), and the reaction was stirred at room temperature for 2 hours. The mixture was washed with water, then brine, dried (MgSO$_4$) and evaporated under reduced pressure to give the title compound as a yellow gum, 823 mg.

$^1$Hnmr (CDCl$_3$, 400 MHz) δ: 1.62 (m, 1H), 2.06 (m, 2H), 2.24 (m, 4H), 2.56 (m, 1H), 2.62 (m, 1H), 2.94 (m, 1H), 3.58 (m, 4H), 4.44 (m, 1H), 6.05 (bs, 1H), 7.20–7.35 (m, 5H).

LRMS: m/z (ES$^+$) 281, 283 [MH$^+$]

Preparation 50

N-[(3R)-1-Benzylpyrrolidinyl]-4-chlorobutanamide

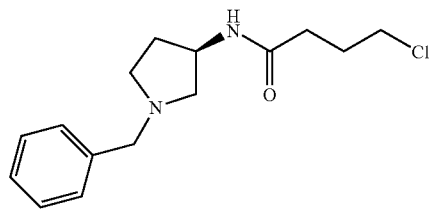

The title compound was obtained as a gum from (3R)-1-benzyl-3-pyrrolidinamine following the procedure described in preparation 49.

$^1$Hnmr (CDCl$_3$, 400 MHz) δ: 1.62 (m, 1H), 2.10 (m, 2H), 2.232 (m, 4H), 2.58 (m, 1H), 2.64 (m, 1H), 2.96 (m, 1H), 3.62 (m, 4H), 4.50 (m, 1H), 6.02 (bs, 1H), 7.15–7.35 (m, 5H).

LRMS: m/z (TSP$^+$) 281.1, 283.1 [MH$^+$]

Preparation 51

1-[(3S)-1-Benzylpyrrolidinyl]-2-pyrrolidone

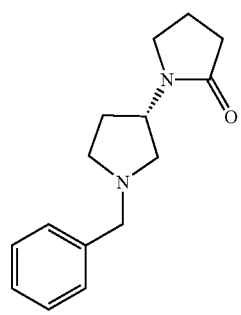

The pyrrolidine from preparation 49 (825 mg, 3 mmol) was added to a mixture of sodium hydride (176 mg, 60% dispersion in mineral oil, 4.4 mmol) in 1-methyl-2-pyrrolidine (10 ml), and the reaction stirred at room temperature for 18 hours. Aqueous ammonium chloride was added to quench the reaction, then the mixture extracted with ethyl acetate. The combined organic solutions were washed with water (3×), brine (3×), dried (MgSO$_4$) and evaporated under reduced pressure. The residual gum was purified by column chromatography on silica gel using dichloromethane:methanol (95:5) as eluant, to afford the title compound as a yellow oil, 250 mg.

$^1$Hnmr (CDCl$_3$, 400 MHz) δ: 1.70 (m, 1H), 1.94 (m, 2H), 2.10 (m, 1H), 2.28 (m, 3H), 2.44 (m, 1H), 2.56 (m, 1H), 2.84 (m, 1H), 3.38–3.68 (m, 4H), 4.76 (m, 1H), 7.20–7.35 (m, 5H).

LRMS: m/z (TSP$^+$) 245.1 [MH$^+$]

Preparation 52

1-[(3R)-1-Benzylpyrrolidinyl]-2-pyrrolidone

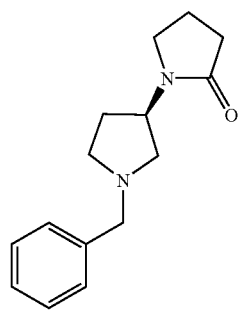

The title compound was obtained as a yellow gum in 18% yield, from the compound from preparation 50, following the procedure described in preparation 51.

$^1$Hnmr (CDCl$_3$, 400 MHz) δ: 1.74 (bs, 1H), 1.98 (m, 2H), 2.08 (m, 1H), 2.16 (m, 3H), 2.50 (m, 1H), 2.62 (m, 1H), 2.90 (m, 1H), 3.40–3.75 (m, 4H), 4.78 (s, 1H), 7.20–7.35 (m, 5H).

LRMS: m/z (TSP$^+$) 245.2 [MH$^+$]

Preparation 53

1-[(3S)-Pyrrolidinyl]-2-pyrrolidone

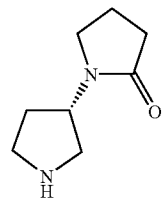

A mixture of the protected pyrrolidine from preparation 51 (246 mg, 1 mmol) and palladium hydroxide (150 mg) in ethanol (10 ml), was hydrogenated at 60 psi and 60° C. for 18 hours. The cooled mixture was filtered through Arbocel®, washing through with ethanol, and the filtrate evaporated under reduced pressure, to give the title compound as a yellow gum, 156 mg.

$^1$Hnmr (CDCl$_3$, 400 MHz) δ: 1.86 (m, 1H), 1.97–2.17 (m, 3H), 2.38 (t, 2H), 3.02 (m, 2H), 3.20 (m, 2H), 3.41 (m, 2H), 4.60 (m, 1H) 4.70–4.92 (bs, 1H).

Preparation 54

1-[(3R)-pyrrolidin-3-yl]-2-pyrrolidone

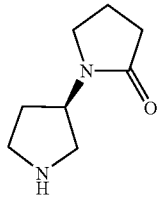

The title compound was obtained as a gum, from the protected pyrrolidine from preparation 52, following the procedure described in preparation 53.

¹Hnmr (CDCl₃, 400 MHz) δ: 1.78 (m, 1H), 2.05 (m, 3H), 2.38 (t, 2H), 2.8–3.05 (m, 3H), 3.16 (m, 2H), 3.42 (t, 2H), 4.60 (m, 1H).

LRMS: m/z (TSP⁺) 155.2 [MH⁺]

Preparation 55

1-Benzyl-4-ethyl-4-piperidinol

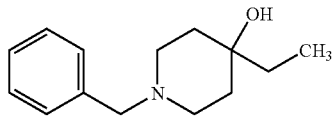

Ethylmagnesium bromide (18 ml, 3M solution in diethyl ether, 54 mmol) was added dropwise over 30 minutes to a cooled (−78° C.) solution of 1-benzyl-4-piperidinone (5 g, 26.4 mmol) in diethyl ether (50 ml). Once addition was complete, the mixture was allowed to warm to room temperature and then stirred for 18 hours.

The residual gum was purified by column chromatography on silica gel using an elution gradient of dichloromethane:methanol:0.88 ammonia (97:3:0.5 to 90:10:1) to afford the title compound as an oil, 848 mg.

¹Hnmr (CDCl₃, 400 MHz) δ: 0.94 (t, 3H), 1.52 m, 4H), 1.63 (m, 2H), 2.35 (m, 2H), 2.62 (m, 2H), 3.55 (s, 2H), 7.32 (m, 5H).

Preparation 56

4-Ethyl-4-piperidinol

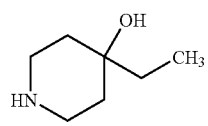

A mixture of the amine from preparation 55 (848 mg, 3.87 mmol) and palladium hydroxide (300 mg) in ethanol (30 ml) was hydrogenated at 60 psi and room temperature for 18 hours. The mixture was filtered through Arbocel®, and the filtrate evaporated under reduced pressure to give the title compound as an oil, 380 mg.

¹Hnmr (CDCl₃, 400 MHz) δ: 0.93 (t, 3H), 1.45–1.66 (m, 6H), 2.88–3.04 (m, 4H).

Preparation 57 tert-Butyl 4-hydroxy-4-(trifluoromethyl)-1-piperidinecarboxylate

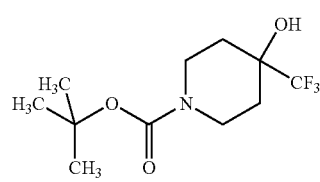

Tetrabutylammonium fluoride (50 mg, 1M solution in tetrahydrofuran) was added to an ice-cooled solution of (trifluoromethyl)trimethylsilane (2.1 g, 15 mmol) and tert-butyl 4-oxo-1-piperidinecarboxylate (2 g, 10 mmol) in tetrahydrofuran (20 ml), and the reaction stirred at room temperature for 18 hours. The mixture was concentrated under reduced pressure, the residue suspended in ethyl acetate, hydrochloric acid (20 ml, 1N) was added, the mixture stirred for an hour, and then neutralised using sodium bicarbonate. The solution was washed with water, then brine, dried (MgSO₄) and evaporated under reduced pressure to give a gum. This was purified by column chromatography on silica gel using an elution gradient of dichloromethane:methanol (100:0 to 98:2) to afford the title compound, 1.94 g.

¹Hnmr (CDCl₃, 400 MHz) δ: 1.42 (s, 9H), 1.68 (d, 2H), 1.76 (m, 2H), 3.02 (m, 2H), 4.02 (m, 2H).

LRMS: m/z (TSP⁺) 270.2 [MH⁺]

Preparation 58

4-Trifluoromethylpiperidinol trifluoroacetate

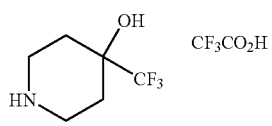

A mixture of the piperidine from preparation 57 (950 mg, 3.6 mmol) and trifluoroacetic acid (5 ml) in dichloromethane (5 ml) was stirred at room temperature for 90 minutes. The mixture was concentrated under reduced pressure, and the residue azeotroped with toluene and dichloromethane. The product was triturated with diethyl ether to afford the title compound as a yellow solid, 866 mg.

¹Hnmr (CDCl₃, 400 MHz) δ: 1.94 (m, 4H), 3.18–3.35 (m, 4H).

LRMS: m/z (TSP⁺) 170.0 [MH⁺]

Preparation 59 tert-Butyl 4-[acetyl(methyl)amino]-1-piperidinecarboxylate

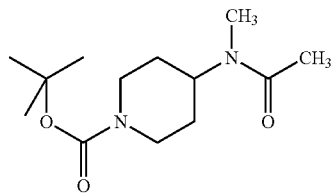

Triethylamine (18 ml, 132 mmol), followed by acetic anhydride (8.8 ml, 93 mmol) were added to a solution of tert-butyl 4-[(methyl)amino]-1-piperidinecarboxylate (WO 9639385) (9 g, 89 mmol) in dichloromethane (300 ml), and the reaction stirred at room temperature for 1 hour. The solution was diluted with dichloromethane (200 ml), washed with 2N citric acid (2×200 ml), brine, dried (MgSO$_4$) and evaporated under reduced pressure. The crude product was purified by column chromatography on silica gel using dichloromethane:methanol (90:10), and the product azeotroped with dichloromethane to afford the title compound as a yellow oil, 20.5 g.

$^1$Hnmr (CDCl$_3$, 300 MHz) δ: (mixture of rotamers) 1.40–1.74 (m, 13H), 2.09, 2.13 (2×s, 3H), 2.67–2.83 (m, 5H), 3.62, 4.60 (2×m, 1H), 4.12–4.25 (m, 2H).

Preparation 60

N-methyl-N-(4-piperidinyl)acetamide hydrochloride

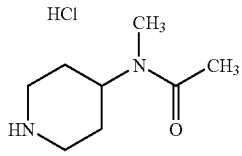

A solution of the protected amine from preparation 59 (20 g, 78 mmol) in dichloromethane (200 ml) was saturated with hydrogen chloride, and the reaction then stirred at room temperature for 1 hour. The mixture was concentrated under reduced pressure, the residue azeotroped with dichloromethane (3×300 ml), and the resulting solid triturated with diethyl ether. The solid was filtered off, and dried under vacuum, to give the title compound as a white solid, 16.3 g.

$^1$Hnmr (DMSOd$_6$, 300 MHz) δ: (mixture of rotamers) 1.55 (m, 1H), 1.70 (m, 1H), 1.96–2.15 (m, 5H), 2.60, 2.78 (2×s, 3H), 2.82–3.02 (m, 2H), 3.22 (m, 2H), 3.98, 4.47 (2×m, 1H), 9.23–9.42 (bs, 2H).

Preparation 61

1-Benzyl-4-piperidinyl methylcarbamate

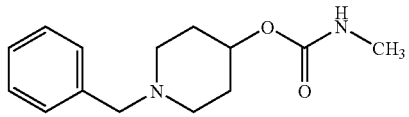

Methyl isocyanate (8.94 g, 157 mmol) was added to a solution of 1-benzyl-4-piperidinol (10 g, 52.3 mmol) in chloroform (80 ml), and the reaction stirred under reflux for 16 hours. The cooled mixture was concentrated under reduced pressure, the residual solid was triturated from 40–60 petroleum ether, and the product filtered and dried to afford the title compound as a white solid, 1 g. m.p.—106–108° C.

Microanalysis found: C, 67.86; 8.14; N, 11.25. C$_{14}$H$_{20}$N$_2$O$_2$ requires C, 67.71; H, 8.12;N, 11.28%.

Preparation 62

4-Piperidinyl methylcarbamate

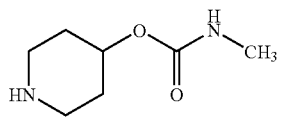

A mixture of the piperidine from preparation 61 (8.2 g, 33.0 mmol) and 10% palladium on charcoal (1 g) in ethanol (200 ml) was hydrogenated at 50° C. and 50 psi for 18 hours. The cooled reaction was filtered through Hyflo®, and the filtrate evaporated under reduced pressure to afford the title compound as a white solid, 5.5 g.

$^1$Hnmr (CDCl$_3$, 90 MHz) δ: 1.0–2.10 (m, 4H), 2.30–3.30 (m, 7H), 4.40–5.20 (m, 2H).

Microanalysis found: C, 53.29; H, 8.87; N, 17.78. C$_7$H$_{14}$N$_2$O$_2$ requires C, 53.14; H, 8.91; N, 17.71%.

Preparation 63 tert-Butyl 4-(4-hydroxypiperidin-1-yl)-1-piperidinecarboxylate

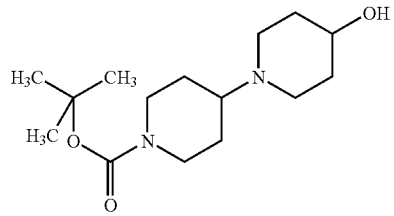

Acetic acid (3.25 ml, 41.3 mmol) followed by tert-butyl 4-oxo-1-piperidinecarboxylate (1 g, 5.0 mmol) and sodium triacetoxyborohydride (2.11 g, 10 mmol) were added to a solution of 4-piperidinol (757 mg, 7.5 mmol) and triethylamine (5.5 ml, 37.5 mmol) in dichloromethane (50 ml), and the reaction stirred at room temperature for 18 hours. The reaction was washed with sodium bicarbonate solution, dried (MgSO$_4$) and evaporated under reduced pressure. The residual oil was purified by column chromatography on silica gel using an elution gradient of dichloromethane:methanol:0.88 ammonia (95:5:0.5 to 93:7:0.5) to give the title compound as a clear gum, 700 mg.

$^1$Hnmr (CDCl$_3$, 400 MHz) δ: 1.40 (m, 11H), 1.58 (m, 2H), 1.78 (m, 2H), 1.95 (m, 2H), 2.24–2.48 (m, 3H), 2.68 (m, 2H), 2.82 (m, 2H), 3.70 (m, 1H), 4.16 (m, 2H).

Preparation 64

1-(Piperidin-4-yl)-4-piperidinol ditrifluoroacetate

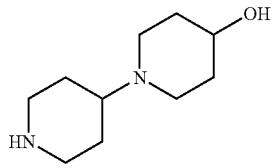

Trifluoroacetic acid (0.58 ml, 7.5 mmol) was added dropwise to an ice-cooled solution of the amine from preparation 63 (700 mg, 2.5 mmol) in dichloromethane (10 ml), and the reaction stirred at room temperature for 18 hours. Tlc analysis showed starting material remaining, so additional trifluoroacetic acid (0.97 ml, 12.5 mmol) was added, and the reaction stirred for a further 2 hours. The mixture was concentrated under reduced pressure and the residue azeotroped with toluene to afford the title compound as an oil, 1.25 g.

$^1$Hnmr (CD$_3$OD, 400 Hz) 67 :1.97 (m, 4H), 2.17 (m, 1H), 2,37 (m, 3H), 3.15 (m, 3H), 3.28–3.61 (m, 7H).

Preparation 65

4-(4-piperidinyl)morpholine Hydrochloride

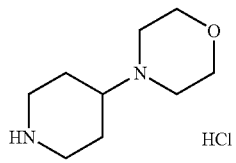

Hydrogen chloride was bubbled through an ice-cooled solution of tert-butyl 4-(4-morpholinyl)-1-piperidinecarboxylate (J.O.C. 1990; 55(8); 2552) (6.5 g, 24 mmol) in dichloromethane (100 ml), and the solution then stirred at 0° C. for 2 hours. The reaction was degassed under nitrogen, allowed to warm to room temperature, and evaporated under reduced pressure to afford the title compound as a white solid, 5.91 g.

$^1$Hnmr (DMSOd$_6$, 400 MHz) δ: 1.90 (m, 2H), 2.22 (m, 2H), 2.80 (m, 2H), 3.00 (m, 2H), 3.38 (m, 5H), 3.90 (m, 4H), 8.92 (bs, 1H), 9.20 (bs, 1H).

LRMS: m/z (ES$^+$) 171.2 [MH$^+$]

Preparation 66

3-(4-Pyridyl)-2,4-imidazolidinedione

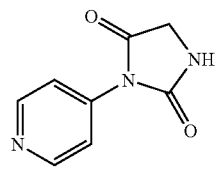

A mixture of 4-aminopyridine (25 g, 266 mmol) and ethylisocyanoacetate (35 g, 271 mmol) in N,N-dimethylformamide (250 ml) was heated under reflux for 90 minutes, and allowed to cool. The resulting precipitate was filtered off, and the filtrate heated under reflux for a further 5 hours. The cooled mixture was concentrated under reduced pressure, and the residue triturated with hot ethanol (500 ml). The resulting solid was filtered, and recrystallised from N,N-dimethylformamide to afford the title compound as a yellow crystalline solid, 47.8 g.

m.p. 232–234° C.

Microanalysis found: C, 53.98; H, 3.99; N, 23.63. C$_8$H$_7$N$_3$O$_2$ requires C, 54.23; H, 3.98; N, 23.63%

Preparation 67

3-(4-Piperidinyl)-2,4-imidazolidinedione

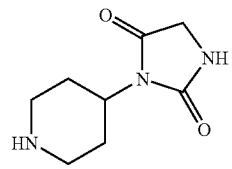

The pyridyl compound from preparation 66 (42 g, 0.24 mol) was dissolved in 5N hydrochloric acid, then evaporated under reduced pressure. The solid was dissolved in water, 5% rhodium on alumina (15 g) added, and the mixture hydrogenated at 50° C. and 750 psi. The cooled mixture was filtered, the filtrate concentrated under reduced pressure and the residue dissolved in water. The solution was basified and evaporated under reduced pressure. The resulting solid was extracted into ethyl acetate using a Soxhlet apparatus over 2 days. The organic solution was evaporated under reduced pressure and the residual yellow solid recrystallised from methanol/butanol to afford the title compound as a white solid, 6.9 g.

m.p. 214–217° C.

Microanalysis found: C, 52.20; H, 7.21; N, 23.04. C$_7$H$_{12}$N$_3$O$_2$ requires C, 52.44; H, 7.15; N, 22.94%

Preparation 68 tert-Butyl 4-(4-pyridinyl)-1-piperidinecarboxylate

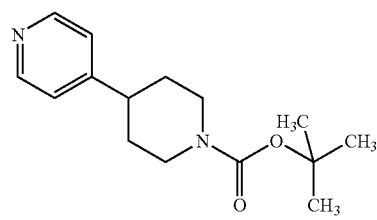

Dichloromethane (0.1 ml) was added to a suspension of zinc (2 g, 31.7 mmol) in N,N-dimethylformamide (5 ml), and the mixture warmed until gas evolution occurred. tert-Butyl 4-iodo-1-piperidinecarboxylate (EP 1078928) (4.9 g, 15.8 mmol), and hydroquinone (35 mg, 0.32 mmol) in N,N-dimethylformamide (5 ml) was added, and the mixture warmed until an exotherm was evident. 4-Bromopyridine (1 g, 6.33 mmol), tris(dibenzylideneacetone)dipalladium (0) (73 mg, 0.127 mmol) and tri(2-furyl)phosphine (59 mg, 0.25 mmol) in N,N-dimethylformamide (5 ml) were added, and the reaction stirred at 60° C. for 30 minutes. The cooled mixture was partitioned between water (100 ml) and diethyl ether (50 ml), and the layers separated. The aqueous phase was extracted with diethyl ether (2×50 ml), the combined organic solutions washed with brine (50 ml), dried (MgSO$_4$) and evaporated under reduced pressure, to give a brown oil. This was purified by column chromatography on silica gel using ethyl acetate:pentane (50:50) as eluant to afford the title compound as a yellow oil, 1.1 g.

$^1$Hnmr (CDCl$_3$, 400 MHz) δ: 1.43 (s, 9H), 1.58 (m, 2H), 1.80 (m, 2H), 2.60 (m, 1H), 2.78 (m, 2H), 4.25 (m, 2H), 7.09 (d, 2H), 8.49 (d, 2H).

LRMS: m/z (TSP$^+$) 263.2 [MH$^+$]

Preparation 69 tert-Butyl 4-(3-pyridinyl)-1-piperidinecarboxylate

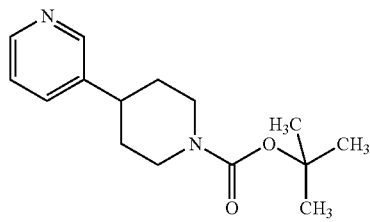

The title compound was obtained as an oil in 40% yield, from tert-butyl 4-iodo-1-piperidinecarboxylate (EP 1078928) and 3-bromopyridine, according to the procedure described in preparation 68.

$^1$Hnmr (CDCl$_3$, 400 MHz) δ: 1.42 (s, 9H), 1.58 (m, 2H), 1.78 (m, 2H), 2.62 (m, 1H), 2.78 (m, 2H), 4.21 (m, 2H), 7.20 (m, 1H), 7.45 (d, 1H), 8.42 (m, 2H).

LRMS: m/z (TSP$^+$) 263.1 [MH$^+$]

Preparation 70 tert-Butyl 4-(1-oxido-4-pyridinyl)-1-piperidinecarboxylate

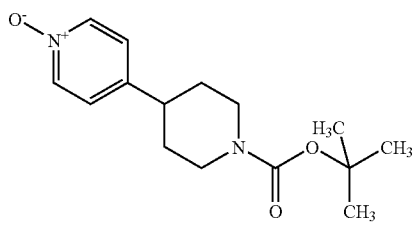

Phthalic anhydride (1.41 g, 9.53 mmol) was added to a suspension of urea hydrogen peroxide addition compound (2.87 g, 30.5 mmol) in dichloromethane (10 ml), and the mixture stirred at room temperature for 15 minutes. The pyridyl compound from preparation 68 (1 g, 3.82 mmol) in dichloromethane (10 ml) was added and the reaction stirred at room temperature for 72 hours. The mixture was washed with water (100 ml), and the aqueous solution was extracted with further dichloromethane (3×75 ml). The combined organic solutions were washed with brine (75 ml), dried (MgSO$_4$) and concentrated under reduced pressure. The residual oil was purified by column chromatography on silica gel using dichloromethane:methanol (95:5) as eluant to afford the title compound as an off-white oil, 978 mg.

$^1$Hnmr (CDCl$_3$, 400 MHz) δ: 1.46 (s, 9H), 1.58 (m, 2H), 1.82 (m, 2H), 2.66 (m, 1H), 2.80 (m, 2H), 4.28 (m, 2H), 7.14 (d, 2H), 8.18 (d, 2H).

LRMS: m/z (TSP$^+$) 279.2 [MH$^+$]

Preparation 71 tert-Butyl 4-(1-oxido-3-pyridinyl)-1-piperidinecarboxylate

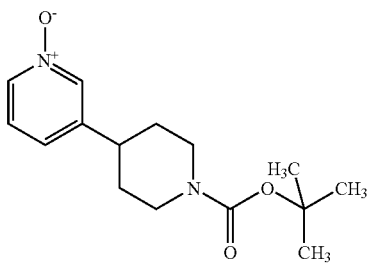

The title compound was obtained as a white solid in 62% yield from the pyridyl compound from preparation 69, according to the procedure descibed in preparation 70.

$^1$Hnmr (CDCl$_3$, 400 MHz) δ: 1.46 (s, 9H), 1.58 (m, 2H), 1.82 (m, 2H), 2.63 (m, 1H), 2.78 (m, 2H), 4.26 (m, 2H), 7.14 (d, 1H), 7.23 (d, 1H), 8.11 (m, 2H).

LRMS: m/z (TSP$^+$) 279.1 [MH$^+$]

Preparation 72

4-(4-Piperidinyl)pyridine 1-oxide Hydrochloride

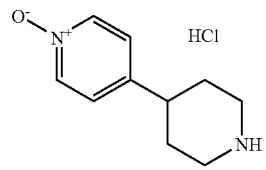

Hydrogen chloride was bubbled through a solution of the pyridyl compound from preparation 70 (978 mg, 3.52 mmol) in dichloromethane (100 ml) for 15 minutes. The reaction mixture was then evaporated under reduced pressure to afford the title compound as a white solid, 1.01 g.

$^1$Hnmr (CD$_3$OD, 400 MHz) δ: 2.00 (m, 2H), 2.18 (m, 2H), 3.18 (m, 2H), 3.28 (m, 1H), 3.54 (m, 2H), 8.00 (d, 2H), 8.84 (d, 2H).

LRMS: m/z (TSP$^+$) 179.2 [MH$^+$]

Preparation 73

3-(4-Piperidinyl)pyridine 1-oxide hydrochloride

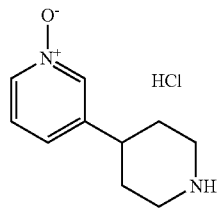

The title compound was obtained as a white solid in quantitative yield, from the pyridyl compound from preparation 71, following the procedure described in preparation 72.

¹Hnmr (CD₃OD, 400 MHz) δ: 2.00 (m, 2H), 2.18 (m, 2H), 3.18 (m, 2H), 3.24 (m, 1H), 3.54 (m, 2H), 7.98 (dd, 1H), 8.32 (d, 1H), 8.78 (d, 1H), 8.90 (s, 1H).
LRMS: m/z (TSP⁺) 179.2 [MH⁺]

Preparation 74

1-(1-Oxido-2-pyridinyl)piperazine dihydrochloride

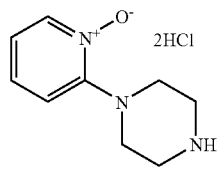

A mixture of 2-chloropyridine 1-oxide (1 g, 6.06 mmol) and piperazine hexahydrate (6 g, 30.9 mmol) were heated at 160–180° C. for 4 hours, using a Dean and Stark apparatus. The cooled mixture was diluted with methanol (15 ml) and dichloromethane (100 ml), silica gel (12 g) added, and the mixture evaporated under reduced pressure. This was purified by column chromatography on silica gel using dichloromethane:methanol:0.88 ammonia (94:12:2) as eluant to give a yellow oil. This was suspended in ethereal hydrochloric acid, and the mixture evaporated under reduced pressure to afford the title compound as a white powder, 0.94 g.

¹Hnmr (DMSOd₆, 400 MHz) δ: 3.20 (m, 4H), 3.58 (m, 4H), 7.02 (dd, 1H), 7.16 (d, 1H), 7.37 (dd, 1H), 8.18 (d, 1H), 9.42 (bs, 2H).

Preparation 75 tert-Butyl 4-(3-cyano-2-pyridinyl)-1-piperazinecarboxylate

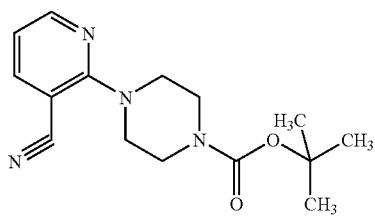

A mixture of 2-chloro-3-cyanopyridine (15.2 g, 0.11 mol), tert-butyl 1-piperazinecarboxylate (25 g, 0.13 mol) and triethylamine (18 ml, 0.13 mol) in toluene (200 ml), was heated under reflux for 24 hours. The cooled mixture was concentrated under reduced pressure and the residue suspended in ethyl acetate (250 ml), and washed with water (3×). The organic solution was dried (MgSO₄), and concentrated under reduced pressure. The residue was triturated with pentane, filtered and dried in vacuo, at 60° C., to afford the title compound as a cream coloured solid, 24.2 g.

¹Hnmr (CDCl₃, 400 MHz) δ: 1.47 (s, 9H), 3.59 (m, 4H), 3.66 (m, 4H), 6.78 (dd, 1H), 7.78 (d, 1H), 8.35 (d, 1H).
LRMS: m/z (TSP⁺) 289.2 [MH⁺]

Preparation 76 tert-butyl 4-[3-(aminomethyl)-2-pyridinyl]-1-piperazinecarboxylate

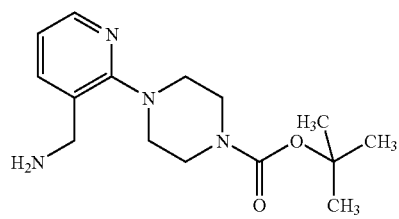

A mixture of the nitrile from preparation 75 (708 mg, 2.45 mmol) and Raney Nickel® (170 mg) in ethanolic ammonia (20 ml) was hydrogenated at 60 psi for 16 hours. The mixture was filtered through Arbocel®, and the filtrate evaporated under reduced pressure to give the title compound as an oil.

¹Hnmr (CDCl₃, 400 MHz) δ: 1.43 (s, 9H), 3.07 (m, 4H), 3.53 (m, 4H), 3.85 (bs, 2H), 6.95 (dd, 1H), 7.63 (d, 1H), 8.19 (s, 1H).
LRMS: m/z (TSP⁺) 292.43 [MH⁺]

Preparation 77 tert-Butyl 4-[3-[(dimethylamino)methyl]-2-pyridinyl]-1-piperazinecarboxylate

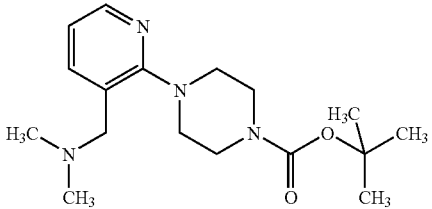

Formaldehyde (2 ml, 33% aqueous solution) and sodium triacetoxyborohydride (525.6 mg, 2.48 mmol) were added to a solution of the amine from preparation 76 (362.1 mg, 1.24 mmol) in dichloromethane (10 ml), and the solution stirred at room temperature for 45 minutes. The mixture was washed with saturated aqueous sodium bicarbonate solution, brine, dried (MgSO₄) and evaporated under reduced pressure to afford the title compound as a yellow oil, 375 mg.

¹Hnmr (CDCl₃, 300 MHz) δ: 1.52 (s, 9H), 2.28 (s, 6H), 3.15 (m, 4H), 3.41 (s, 2H), 3.59 (m, 4H), 6.97 (dd, 1H), 7.72 (d, 1H), 8.22 (d, 1H).
LRMS: m/z (TSP⁺) 321.3 [MH⁺]

Preparation 78 tert-Butyl 4-(3-{[(methylsulfonyl)amino]methyl}-2-pyridinyl)-1-piperazinecarboxylate

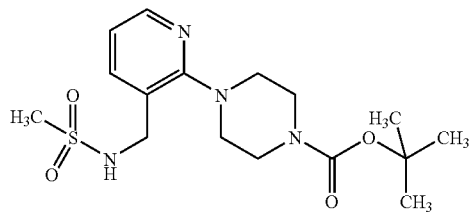

Triethylamine (0.2 ml, 1.43 mmol), followed by methanesulfonyl chloride (0.1 ml, 1.29 mmol) were added to an ice-cooled solution of the amine from preparation 76 (362.1 mg, 1.24 mmol) in dichloromethane (10 ml), and the solution stirred for 30 minutes. The mixture was washed with 10% aqueous citric acid solution, then brine, dried (MgSO$_4$) and evaporated under reduced pressure to afford the title compound as a yellow oil, 306 mg.

$^1$Hnmr (CDCl$_3$, 300 MHz) δ: 1.49 (s, 9H), 2.93 (s, 3H), 3.12 (s, 4H), 3.61 (m, 4H), 4.39 (s, 2H), 5.51 (bs, 1H), 7.06 (dd, 1H), 7.69 (d, 1H), 8.32 (s, 1H).

LRMS: m/z (TSP$^+$) 371.2 [MH$^+$]

Preparation 79

N,N-Dimethyl[2-(1-piperazinyl)-3-pyridinyl]methanamine trihydrochloride

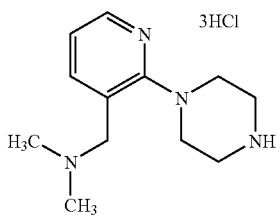

Hydrogen chloride was bubbled through a solution of the protected amine from preparation 77 (375.8 mg, 1.17 mmol) in dichloromethane (50 ml), and the solution stirred for 30 minutes. The mixture was evaporated under reduced pressure and the residue dried in vacuo, to afford the title compound, 371 mg.

$^1$Hnmr (CD$_3$OD, 300 MHz) δ: 2.94 (s, 6H), 3.41–3.58 (m, 10H), 7.42 (dd, 1H), 8.17 (d, 1H), 8.52 (d, 1H).

LRMS: m/z (TSP$^+$) 221.2 [MH$^+$]

Preparation 80

N-Methyl-N-{[2-(1-piperazinyl)-3-pyridinyl]methyl}methanesulfonamide dihydrochloride

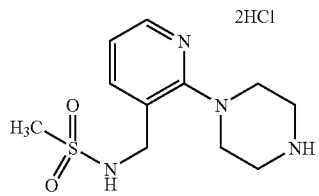

The title compound was obtained as a white solid in 97% yield from the protected amine from preparation 78, according to the procedure described in preparation 79.

$^1$Hnmr (DMSOd$_6$, 300 MHz) δ: 2.94 (s, 3H), 3.18 (m, 4H), 3.31 (m, 4H), 4.12 (s, 2H), 7.17 (dd, 1H), 7.59 (bs, 1H), 7.87 (d, 1H), 8.19 (d, 1H), 9.33 (bs, 2H).

LRMS: m/z (TSP$^+$) 271.2 [MH$^+$]

Preparation 81 tert-Butyl 4-(methylsulfonyl)-1,4-diazepane-1-carboxylate

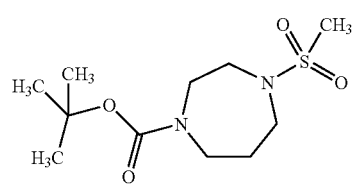

Methanesulfonyl chloride (0.64 ml, 8.24 mmol) was added to a solution of tert-butyl 1,4-diazepane-1-carboxylate (1.5 g, 7.49 mmol) and triethylamine (1.6 ml, 11 mmol) in dichloromethane (20 ml), and the reaction stirred at room temperature for 18 hours. The solution was washed with sodium bicarbonate solution, then brine, dried (MgSO$_4$) and evaporated under reduced pressure to give the title compound, 2.01 g.

$^1$Hnmr (CDCl$_3$, 300 MHz) δ: 1.45 (s, 9H), 1.95 (m, 2H), 2.83 (s, 3H), 3.38 (m, 4H), 3.52 (m, 4H).

Preparation 82

1-(Methylsulfonyl)-1,4-diazepane hydrochloride

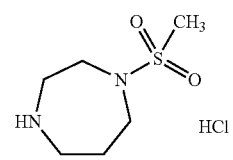

Hydrogen chloride was bubbled through an ice-cooled solution of the compound from preparation 81 (2.0 g, 7.2 mmol) in dichloromethane (50 ml), for 15 minutes. The solution was allowed to warm to room temperature and concentrated under reduced pressure. The residue was azeotroped with dichloromethane and triturated with diethyl ether to afford the title compound as a solid, 1.45 g.

$^1$Hnmr (DMSOd$_6$, 300 MHz) δ: 2.00 (m, 2H), 2.98 (s, 3H), 3.17 (m, 4H), 3.35 (t, 2H), 3.54 (t, 2H), 9.35 (bs, 2H).

LRMS: m/z (TSP$^+$) 179.2 [MH$^+$]

143

Preparation 83

N-(1-{2-[(3S)-3-(3,4-Dichlorophenyl)-6-oxopiperidinyl]ethyl}-4-piperidinyl)-N-methylacetamide

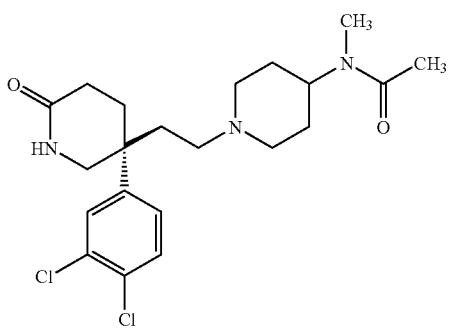

Triethylamine (4.2 ml, 30 mmol) was added to a suspension of [(3S)-3-(3,4-dichlorophenyl)-6-oxopiperidinyl]acetaldehyde (WO 9605193) (5 g, 17.5 mmol) and the amine from preparation 60 (5 g, 26.2 mmol) in dichloromethane (400 ml) and the mixture stirred at room temperature, until all solids had dissolved. Acetic acid, was added (ca. 5 ml) to the reaction to give pH 4, the solution stirred for 30 minutes, then sodium triacetoxyborohydride (7.4 g, 35 mmol) added, and the reaction stirred for 3 hours. The mixture was diluted with dichloromethane (300 ml), and washed with sodium hydroxide solution (400 ml, 1N). The aqueous phase was extracted with further dichloromethane (×2), the combined organic solutions washed with brine, dried (Na$_2$SO$_4$) and evaporated under reduced pressure. The crude product was purified by column chromatography on silica gel using an elution gradient of dichloromethane:methanol:0.88 ammonia (99:1:0.1 to 85:15:1.5) to give the title compound, 4.5 g.

$^1$Hnmr (CD$_3$OD, 400 MHz) δ: 1.35–2.17 (m, 15H), 2.17–2.41 (m, 3H), 2.75 (m, 1H), 2.78–2.93 (m, 4H), 3.40 (dd, 1H), 3.75 (dd, 1H), 3.56, 4.25 (m, 1H), 7.33 (m, 1H), 7.49 (d, 1H), 7.56 (s, 1H).

LRMS: m/z (ES$^+$) 448, 450 [MNa$^+$]

Preparation 84 tert-Butyl 1-(1-{2-[(3S)-3-(3,4-dichlorophenyl)-6-oxo-1-(2-pyridinyl)piperidinyl]ethyl}-3-azetidinyl)-4-piperidinylcarbamate

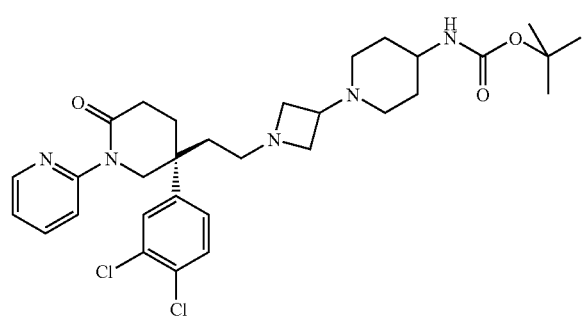

A mixture of the aldehyde from preparation 11a (250 mg, 0.62 mmol), tert-butyl-1-(3-azetidinyl)-4-piperidinylcarbamate trifluoroacetate (WO 9605193) (450 mg, 0.93 mmol), triethylamine (1 ml) and acetic acid (1.1 ml) and sodium triacetoxyborohydride (250 mg, 1.24 mmol) in dichloromethane (50 ml) was stirred at room temperature for 90 minutes. The reaction mixture was washed with water, dried (MgSO$_4$) and evaporated under reduced pressure. The crude product was purified by column chromatography on silica gel using an elution gradient of dichloromethane:methanol (100:0 to 95:5) to afford the title compound, 252 mg.

$^1$Hnmr (CDCl$_3$, 400 MHz) δ: 1.44 (s, 9H), 1.82–2.70 (m, 16H), 2.80–3.05 (m, 3H), 3.48 (m, 1H), 3.62 (m, 2H), 3.92 (d, 1H), 4.40 (d, 1H), 4.58 (d, 1H), 7.18 (m, 1H), 7.22 (d, 1H), 7.42 (s, 1H), 7.44 (d, 1H), 7.74 (d, 2H), 8.54 (d, 1H).

LRMS: m/z (TSP$^+$) 502.1, 503.1 [MH$^+$]

Preparation 85 tert-Butyl 1-(1-{2-[(3S)-3-(3,4-dichlorophenyl)-1-(6-methyl-2-pyridinyl)-6-oxopiperidinyl]ethyl}-3-azetidinyl)-4-piperidinylcarbamate

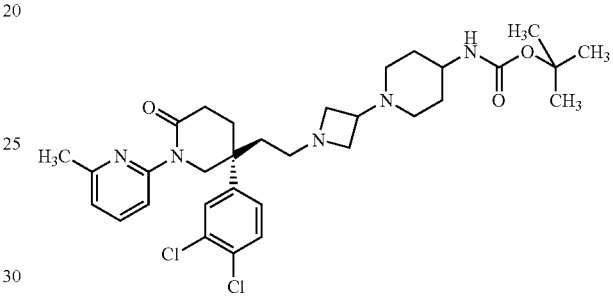

A mixture of the aldehyde from preparation 12a (260 mg, 0.71 mmol), tert-butyl-1-(3-azetidinyl)-4-piperidinylcarbamate trifluoroacetate (WO 9605193) (350 mg, 0.78 mmol), triethylamine (0.26 ml, 1.86 mmol) and titanium isopropoxide (2.3 ml, 0.78 mmol) in ethanol (3 ml), was stirred at room temperature for 18 hours. Sodium borohydride (50 mg, 1.35 mmol) in ethanol (5 ml) was then added and the reaction stirred for 30 minutes. Sodium hydroxide was added, the resulting precipitate filtered off, and washed with ethyl acetate. The filtrate was washed with water (2×) and brine (2×), dried (MgSO$_4$) and evaporated under reduced pressure. The residual gum was purified by column chromatography on silica gel using an elution gradient of dichloromethane:methanol (100:0 to 99:1) to afford the title compound as a yellow/white solid, 59 mg.

$^1$Hnmr (CDCl$_3$, 400 MHz) δ: 1.35 (m, 3H), 1.40 (s, 9H), 1.64–1.95 (m, 8H), 2.08 (m, 2H), 2.22 (m, 2H), 2.55 (m, 7H), 2.80 (t, 1H), 3.40 (m, 2H), 3.80 (d, 1H), 4.36 (m, 1H), 4.44 (d, 1H), 6.96 (d, 1H), 7.16 (d, 1H), 7.38 (dd, 2H), 7.50 (d, 1H), 7.58 (dd, 1H).

LRMS: m/z (TSP$^+$) 617.2 [MH$^+$]

What is claimed is:
1. A compound of formula (I)

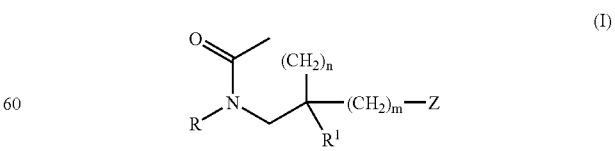

or a pharmaceutically acceptable salt, prodrug, solvate or polymorph thereof, wherein:
R is het$^a$;
R$^1$ is phenyl optionally substituted by one or more substituents independently selected from halogen, C$_{1-6}$ alkoxy optionally substituted by one or more halogen, and $C_{1-6}$ alkyl optionally substituted by one or more halogen;

m is 1–4;

Z is selected from:
a) $N(R^3)(R^4X)$
wherein X is $NR^3R^5$, $OR^3$, $Oaryl^1$, $Ohet^b$, $Ohet^c$, $aryl^1$, $het^b$ or $het^c$;
b) $N(R^3)Y$
wherein Y is $aryl^1$, $het^b$ or $het^c$; and
c) a 4–7 membered N containing saturated or partially saturated heterocycle said heterocycle attached to the alkylene link via said nitrogen atom, said heterocycle optionally containing an additional 1–3 groups, each independently selected from C=O, NH, $S(O)_p$ and O; optionally, said heterocycle is:
(i) spirofused with $het^b$, such that both rings share 1 atom; or
(ii) substituted by 1–3 groups each independently selected from $het^b$, $het^c$, $aryl^1$, $R^3$, $R^4OR^3$, $R^4C(O)R^3$, $OR^3$, $OR^7OR^3$, $OR^4OC(O)R^3$, $OR^4OC(O)NR^3R^6$, $S(O)_pR^4$, $C(O)R^3$, $C(O)NR^3R^6$, $C(O)OR^3$, $R^7C(O)OR^3$, $C(O)R^7OR^3$, $C(O)OR^7OR^3$, $CF_3$, $NR^3R^6$, $R^4NR^3R^5$, $OC(O)NR^3R^4$ and $NR^3R^5$;

wherein $R^3$ and $R^6$ are both independently selected from H and $C_{1-6}$ alkyl;

wherein $R^4$ and $R^7$ are both independently selected from $C_{1-6}$ alkylene;

wherein $R^5$ is selected from $C(O)OR^3$, $S(O)_pR^3$, $S(O)_p aryl^1$, $C(O)R^3$, and $C(O)NR^3R^6$;

$het^b$ is a 4–7 membered heterocycle containing 1–3 heteroatoms, each independently selected from N, O and S, said N being optionally substituted with O, said ring optionally containing 1–2 C=O groups, said ring being saturated or partially saturated, said ring being optionally benzofused, said ring being optionally substituted by 1–3 substituents selected from halo, $R^3$, $OR^3$, $C(O)NR^3R^6$, $R^7NR^3R^6$, $NR^3R^5$, $NHS(O)_pR^4$, $S(O)_pNR^3R^6$, $S(O)_pR^4$, CN, $NR^3R^6$ and $aryl^1$;

$het^a$ and $het^c$ independently represent a 5–7 membered aromatic heterocycle containing 1–3 heteroatoms each independently selected from N, O and S, said ring being optionally benzofused, said ring system as a whole being optionally substituted by 1–3 substituents, each independently selected from: halo, $R^3$, $OR^3$, $C(O)NR^3R^6$, $R^4NR^3R^6$, $NR^3R^5$, $NHS(O)_pR^4$, $S(O)_pNR^3R^6$, $S(O)_pR^4$, CN, $NR^3R^6$ and $R^4NR^3S(O)_pR^3$; $aryl^1$ is phenyl or naphthyl, each optionally substituted by 1–3 substituents, each independently selected from: halo, $R^3$, $OR^3$, $C(O)NR^3R^6$, $R^7NR^3R^6$, $NR^3R^5$, $NHS(O)_pR^4$, $S(O)_pNR^3R^6$, $S(O)_pR^4$, CN;

p is 0, 1 or 2; and n is 2.

2. A compound according to claim 1 having the following stereochemistry:

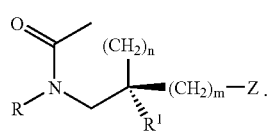

(I)

3. A compound according to claim 1, wherein R is pyridyl, optionally substituted by $NR^3R^6$, $R^3$ or $OR^3$.

4. A compound according to claim 1, wherein $R^1$ is phenyl optionally substituted by 1 or 2 halo substituents.

5. A compound according to claim 1, wherein m is 2–3.

6. A compound according to claim 1, wherein $R^3$ is H or $C_{1-4}$ alkyl.

7. A compound according to claim 1, wherein $R^4$ is $C_{1-4}$ alkylene.

8. compound according to claim 1, wherein $R^5$ is $C(O)OR^3$, $C(O)R^3$, $C(O)NR^3R^6$.

9. A compound according to claim 1, wherein Z is a piperidine or azetidine group optionally substituted by one or more of $het^b$, $het^c$, $aryl^1$, $OR^3$, $R^3$ and $NR^3R^5$, wherein;
$het^b$ is a 5–6 membered saturated or partially saturated nitrogen containing heterocycle, said heterocycle optionally incorporating 1–2 groups each independently selected from O, C=O and N, said heterocycle being optionally benzofused, said heterocycle being optionally substituted by 1–2 substituents, each independently selected from $OR^3$, $R^3$, $NR^3R^6$, $NR^3R^5$, $aryl^1$, $SO_2R^4$ and $SO_2NR^3R^6$;
$het^c$ is pyridyl, optionally substituted by 1 or 2 substituents each independently selected from halo and $OR^3$;
$aryl^1$ is phenyl, optionally substituted by 1 or 2 substituents each independently selected from halo and $OR^3$; and
$R^3$, $R^4$, $R^5$ and $R^6$ are as defined in claim 1.

10. A compound according to claim 1, wherein Z is a piperidine or azetidine group, optionally substituted by $het^b$, $aryl^1$ and $NR^3R^5$; wherein $het^b$ is a morpholine or piperidine, optionally substituted at the 4 position by OH and or methyl; wherein; $aryl^1$ is phenyl optionally substituted by OH; and $R^3$ is H or methyl and $R^5$ is $C(O)CH^3$.

11. A compound according to claim 1, wherein Z is

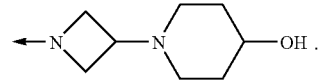

12. A compound according to claim 1 selected from:
(5S)-5-(3,4-Dichlorophenyl)-1-(6methyl-2pyridinyl)-5-{2- [3-(4morpholinyl)-1-azetidinyl]ethyl}-2-piperidinone;
(5S)-5-(3,4-Dichlorophenyl)-1-(6methyl-2-pyridinyl) 5-{2- [3-(4-hydroxypiperidinyl)-1-azetidinyl]ethyl}-2-piperidinone;
(5S)-5-(3,4-Dichlorophenyl)-5- [2-(4methoxy-1-piperidinyl)ethyl]-1-(2-pyridinyl)-2-piperidinone;
(5S)-5-(3,4-Dichlorophenyl)-1-(6-methyl-2-pyridinyl)-5- {{2-[4-hydroxy-4-phenyl]-1-piperidinyl}ethyl}-2-piperidinone;
(5S)-5-(3,4-Dichlorophenyl)-5-{2-[4-hydroxy-4-(2-pyridyl)-1-piperidinyl]ethyl}-1-(2-pyridinyl)-2-piperidinone;
N-(1-{2-[(3S)-3-(3,4-Dichlorophenyl)-6oxo1 (2-pyridinyl)piperidinyl]ethyl}-4-phenyl-4-piperidinyl)-acetamide;
(5S)-5-(3,4-Dichlorophenyl)-1-(6-methoxy-2-pyridinyl)-5-{2-[3-(4morpholinyl)-1-azetidinyl]ethyl}-2-piperidinone;
5-(3,4-Dichlorophenyl)-1-(6-methyl-2-pyridinyl)-5-{2-[3-(4-oxo-1-piperidinyl)-1-azetidinyl] ethyl}2piperidinone;
(5S)-5-(3,4-Dichlorophenyl)-5-{2-[3-(4-hydroxy-1-piperidinyl)-1-azetidinyl]ethyl}-1-(2-pyridinyl)-2-piperidinone; and N-(1-{2[(3S)-3-(3,4-Dichlorophenyl)-6-oxo-1-(2-pyridinyl)piperidinyl]ethyl}-4-piperidinyl)-N-methylacetamide.

13. A process of preparing a compound according to claim 1 comprising subjecting a compound of formula (II) to a reductive amination to give a compound of formula (I):

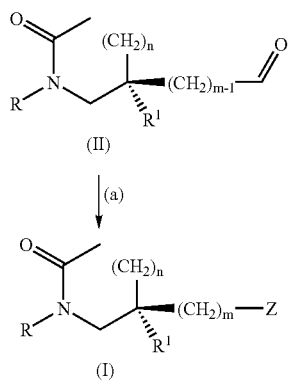

wherein R, R¹, m, n and Z are as defined in claim 1.

14. A process for preparing a compound according to claim 1, comprising subjecting a compound (VIII) to an alkylation reaction to give a compound of formula (I):

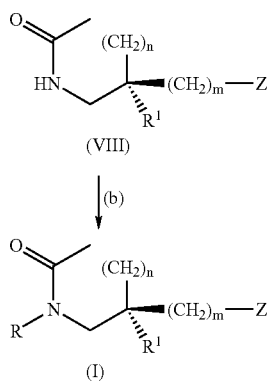

wherein R, R¹, m, n and Z are as defined in claim 1.

15. A method of treating or preventing a condition for which an NK₂ antagonist is efficacious which comprises administering a therapeutically effective amount of a compound according to claim 1 to a patient in need of treatment.

16. A composition comprising a compound according to claim 1 and a pharmaceutically acceptable diluent or carrier.

17. A composition comprising a compound according to claim 1 and an agent selected from: Muscarinic antagonists; alpha-adrenoceptor antagonists; serotonin/noradrenalin reuptake inhibitors (SNRI); reuptake inhibitors; $NK_1$ antagonists; $5-HT_{1A}$ agonists/antagonists; $PDE_5$ inhibitors; $COX_2$ inhibitors; nonselective COX inhibitors; vanilloid receptor agonists; HMG-CoA reductase inhibitors; estrogenic modulators and selective estrogen receptor modulators, and a pharmaceutically acceptable diluent or carrier.

18. A composition comprising a compound according to claim 1 and an agent selected from: NSAIDs, opioids, muscarinic antagonists; cholinergic analgesics; alpha-adrenoceptor antagonists; serotonin/noradrenalin reuptake inhibitors (SNRI); $COX_2$ inhibitors; non-selective COX inhibitors; tricyclic antidepressants, anticonvulsants, serotonin reuptake inhibitors,serotonin receptor agonists and antagonists, sedatives,skeletal muscle relaxant and NMDA receptor antagonists, and a pharmaceutically acceptable diluent or carrier.

19. A method of treating a condition selected from: inflammatory disease, a central nervous system (CNS) disorder, a gastrointestinal (GI) disorder, a disease caused by *Helicobacter pylon* or other disease positive Gram negative bacteria, urological conditions, a pulmonary disorder, an allergy, a hypersensitivity disorder, a vasospastic disease, a proliferative disorder, a fibrosing or collagen disease, reflux sympathetic dystrophy, an addiction disorder, a stress-related somatic disorder, a peripheral neuropathy, a neuropathological disorder, a disorder related to immune enhancement or suppression, a rheumatic disease, an opthalmic disease, acute and chronic pain or viral disease, which comprises administering a therapeutically effective amount of a compound of claim 1 to a patient in need of treatment.

20. A method according to claim 19, wherein said condition is selected from urological conditions or acute and chronic pain.

21. A method according to claim 20, wherein said urological condition is overactive bladder.

22. A method according to claim 20, wherein said pain is neuropathic pain.

* * * * *